United States Patent
Labkovsky et al.

(10) Patent No.: US 9,550,826 B2
(45) Date of Patent: Jan. 24, 2017

(54) GLYCOENGINEERED BINDING PROTEIN COMPOSITIONS

(71) Applicant: AbbVie Inc., North Chicago, IL (US)

(72) Inventors: Boris Labkovsky, Marlborough, MA (US); Tariq Ghayur, Holliston, MA (US); Georgeen Gaza-Bulseco, Princeton, MA (US); Pratibha Mishra, Shrewsbury, MA (US); Subramanya Hegde, Shrewsbury, MA (US); Sudha Krishnan, Acton, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/198,696

(22) Filed: Jun. 30, 2016

(65) Prior Publication Data

US 2016/0319010 A1   Nov. 3, 2016

Related U.S. Application Data

(63) Continuation of application No. 14/542,281, filed on Nov. 14, 2014.

(60) Provisional application No. 62/051,669, filed on Sep. 17, 2014, provisional application No. 61/904,487, filed on Nov. 15, 2013.

(51) Int. Cl.
*C07K 16/24* (2006.01)
*A61K 39/00* (2006.01)

(52) U.S. Cl.
CPC ....... *C07K 16/241* (2013.01); *A61K 2039/505* (2013.01); *C07K 2317/14* (2013.01); *C07K 2317/21* (2013.01); *C07K 2317/41* (2013.01); *C07K 2317/52* (2013.01)

(58) Field of Classification Search
CPC ............. C07K 16/241; C07K 2317/14; C07K 2317/21; C07K 2317/52; C07K 2317/41; A61K 2039/505
See application file for complete search history.

(56) References Cited

U.S. PATENT DOCUMENTS

| | | |
|---|---|---|
| 3,887,430 A | 6/1975 | Torney et al. |
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,925,796 A | 5/1990 | Bergh et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,047,335 A | 9/1991 | Paulson et al. |
| 5,096,816 A | 3/1992 | Maiorella |
| 5,110,913 A | 5/1992 | Coan et al. |
| 5,112,469 A | 5/1992 | Kempf et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,169,936 A | 12/1992 | Staples et al. |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,605,923 A | 2/1997 | Christensen, IV et al. |
| 5,616,487 A | 4/1997 | Palsson et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |

(Continued)

FOREIGN PATENT DOCUMENTS

| | | |
|---|---|---|
| CN | 1563090 A | 1/2005 |
| CN | 105777895 A | 7/2016 |

(Continued)

OTHER PUBLICATIONS

U.S. Appl. No. 15/149,898.
U.S. Appl. No. 14/077,576.
U.S. Appl. No. 14/923,966.
U.S. Appl. No. 14/195,588.
U.S. Appl. No. 15/175,752.
U.S. Appl. No. 15/029,947.
U.S. Appl. No. 15/096,043.
U.S. Appl. No. 14/989,491.
U.S. Appl. No. 14/883,195.
U.S. Appl. No. 62/020,764.

(Continued)

*Primary Examiner* — Ruixiang Li
(74) *Attorney, Agent, or Firm* — McCarter & English, LLP; Maria Laccotripe Zacharakis; Kevin A. Fiala

(57) ABSTRACT

Provided are glycoengineered populations of Fc domain-containing binding proteins with a reduced anti-drug immune response (ADA). Also provided are methods of treating disease using such compositions, and methods and host for making such compositions.

30 Claims, 20 Drawing Sheets

(56) References Cited

U.S. PATENT DOCUMENTS

| | | |
|---|---|---|
| 5,721,121 A | 2/1998 | Etcheverry et al. |
| 5,730,975 A | 3/1998 | Hotamisligil et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,945,311 A | 8/1999 | Lindhofer et al. |
| 5,976,833 A | 11/1999 | Furukawa et al. |
| 5,989,830 A | 11/1999 | Davis et al. |
| 5,994,510 A | 11/1999 | Adair et al. |
| 6,005,082 A | 12/1999 | Smeds |
| 6,015,558 A | 1/2000 | Hotamisligil et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,093,324 A | 7/2000 | Bertolini et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,171,825 B1 | 1/2001 | Chan et al. |
| 6,235,281 B1 | 5/2001 | Stenzel et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,303,626 B1 | 10/2001 | Abramovici et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,506,598 B1 | 1/2003 | Andersen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,656,466 B1 | 12/2003 | Etcheverry et al. |
| 6,673,575 B1 | 1/2004 | Franze et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,936,441 B2 | 8/2005 | Reiter et al. |
| 6,974,681 B1 | 12/2005 | McGrew |
| 7,029,872 B2 | 4/2006 | Gerngross |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,229,432 B2 | 6/2007 | Marshall et al. |
| 7,250,165 B2 | 7/2007 | Heavner et al. |
| 7,276,239 B2 | 10/2007 | Le et al. |
| 7,297,680 B2 | 11/2007 | Opstelten et al. |
| 7,323,553 B2 | 1/2008 | Fahrner et al. |
| 7,326,681 B2 | 2/2008 | Gerngross |
| 7,332,303 B2 | 2/2008 | Schilling et al. |
| 7,390,660 B2 | 6/2008 | Behrendt et al. |
| 7,427,659 B2 | 9/2008 | Shukla et al. |
| 7,429,491 B2 | 9/2008 | Luan et al. |
| 7,449,308 B2 | 11/2008 | Gerngross et al. |
| 7,473,680 B2 | 1/2009 | DeFrees et al. |
| 7,504,485 B2 | 3/2009 | Salfeld et al. |
| 7,517,670 B2 | 4/2009 | Umana et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,612,181 B2 | 11/2009 | Wu et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,906,329 B2 | 3/2011 | Umana et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,034,906 B2 | 10/2011 | Borhani et al. |
| 8,043,863 B2 | 10/2011 | Bosques et al. |
| 8,053,236 B2 | 11/2011 | Morris et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,216,583 B2 | 7/2012 | Kruase et al. |
| 8,216,851 B2 | 7/2012 | Parsons et al. |
| 8,231,876 B2 | 7/2012 | Wan et al. |
| 8,304,250 B2 | 11/2012 | Parsons et al. |
| 8,313,925 B2 | 11/2012 | Gregory et al. |
| 8,338,088 B2 | 12/2012 | Collins et al. |
| 8,361,705 B2 | 1/2013 | Parsons et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,388,965 B2 | 3/2013 | Rao et al. |
| 8,399,627 B2 | 3/2013 | Votsmeier et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,318 B2 | 6/2013 | Ravetch et al. |
| 8,470,552 B2 | 6/2013 | Croughan et al. |
| 8,512,983 B2 | 8/2013 | Gawlitzek et al. |
| 8,530,192 B2 | 9/2013 | Knudsen |
| 8,586,356 B2 | 11/2013 | Bosques et al. |
| 8,623,644 B2 | 1/2014 | Umana et al. |
| 8,629,248 B2 | 1/2014 | Umana et al. |
| 8,632,773 B2 | 1/2014 | Kasermann et al. |
| 8,652,487 B2 | 2/2014 | Maldonado |
| 8,663,945 B2 | 3/2014 | Pla et al. |
| 8,663,999 B2 | 3/2014 | Parsons et al. |
| 8,703,498 B2 | 4/2014 | Parsons et al. |
| 8,729,241 B2 | 5/2014 | Liu et al. |
| 8,753,633 B2 | 6/2014 | Salfeld et al. |
| 8,821,865 B2 | 9/2014 | Neu et al. |
| 8,852,889 B2 | 10/2014 | Prentice |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 8,969,024 B2 | 3/2015 | Kaymakcalan et al. |
| 9,017,687 B1 | 4/2015 | Wang et al. |
| 9,018,361 B2 | 4/2015 | Hickman et al. |
| 9,023,992 B2 | 5/2015 | Rasmussen et al. |
| 9,035,027 B2 | 5/2015 | Ghayur et al. |
| 9,062,106 B2 | 6/2015 | Bengea et al. |
| 9,067,990 B2 | 6/2015 | Wang et al. |
| 9,073,988 B2 | 7/2015 | Pla et al. |

(56) References Cited

U.S. PATENT DOCUMENTS

| | | |
|---|---|---|
| 9,085,618 B2 | 7/2015 | Ramasubramanyan et al. |
| 9,085,619 B2 | 7/2015 | Fraunhofer et al. |
| 9,090,688 B2 | 7/2015 | Bengea et al. |
| 9,090,867 B2 | 7/2015 | Pla et al. |
| 9,096,666 B2 | 8/2015 | Wan et al. |
| 9,096,879 B2 | 8/2015 | Khetan et al. |
| 9,102,723 B2 | 8/2015 | Wan et al. |
| 9,103,821 B2 | 8/2015 | Bosques et al. |
| 9,109,010 B2 | 8/2015 | Hickman et al. |
| 9,144,755 B2 | 9/2015 | Brown et al. |
| 9,145,546 B2 | 9/2015 | Nurcombe et al. |
| 9,150,645 B2 | 10/2015 | Subramanian et al. |
| 9,181,337 B2 | 11/2015 | Subramanian et al. |
| 9,181,572 B2 | 11/2015 | Subramanian et al. |
| 9,182,467 B2 | 11/2015 | Parsons et al. |
| 9,200,069 B2 | 12/2015 | Ramasubramanyan et al. |
| 9,200,070 B2 | 12/2015 | Ramasubramanyan et al. |
| 9,206,390 B2 | 12/2015 | Rives et al. |
| 9,234,032 B2 | 1/2016 | Pla et al. |
| 9,234,033 B2 | 1/2016 | Rives et al. |
| 9,249,182 B2 | 2/2016 | Herigstad et al. |
| 9,255,143 B2 | 2/2016 | Bengea et al. |
| 9,265,815 B2 | 2/2016 | Fraser et al. |
| 9,266,949 B2 | 2/2016 | Ramasubramanyan et al. |
| 9,273,132 B2 | 3/2016 | Wan et al. |
| 9,284,371 B2 | 3/2016 | Pla et al. |
| 9,290,568 B2 | 3/2016 | Rives et al. |
| 9,315,574 B2 | 4/2016 | Ramasubramanyan et al. |
| 9,328,165 B2 | 5/2016 | Wan et al. |
| 9,334,319 B2 | 5/2016 | Ramasubramanyan et al. |
| 9,346,879 B2 | 5/2016 | Ramasubramanyan et al. |
| 9,359,434 B2 | 6/2016 | Subramanian et al. |
| 9,365,645 B1 | 6/2016 | Bengea et al. |
| 2001/0021525 A1 | 9/2001 | Hirai et al. |
| 2002/0045207 A1 | 4/2002 | Krummen et al. |
| 2002/0119530 A1 | 8/2002 | Maiorella et al. |
| 2002/0132299 A1 | 9/2002 | Field |
| 2002/0137673 A1 | 9/2002 | Pingel et al. |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0170813 A1 | 9/2003 | Suga et al. |
| 2003/0175884 A1 | 9/2003 | Umana et al. |
| 2003/0178368 A1 | 9/2003 | van Reis |
| 2003/0203448 A1 | 10/2003 | Reiter et al. |
| 2003/0206898 A1 | 11/2003 | Fischkoff et al. |
| 2003/0211573 A1 | 11/2003 | Ryll |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0043446 A1 | 3/2004 | DeFrees et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136986 A1 | 7/2004 | Raju |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0191256 A1 | 9/2004 | Raju |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0084969 A1 | 4/2005 | Schorgendorfer et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0057638 A1 | 3/2006 | Bosques et al. |
| 2006/0083741 A1 | 4/2006 | Hoffman et al. |
| 2006/0127950 A1 | 6/2006 | Bosques et al. |
| 2006/0149042 A1 | 7/2006 | Konstantinov et al. |
| 2006/0223147 A1 | 10/2006 | Nishiya et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0275867 A1 | 12/2006 | Chotteau et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0015239 A1 | 1/2007 | Bihoreau et al. |
| 2007/0020260 A1 | 1/2007 | Presta |
| 2007/0041905 A1 | 2/2007 | Hoffman et al. |
| 2007/0054390 A1 | 3/2007 | Kelley et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0134256 A1 | 6/2007 | Lai et al. |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0212770 A1 | 9/2007 | Grillberger et al. |
| 2007/0248600 A1 | 10/2007 | Hansen et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0009040 A1 | 1/2008 | Grillberger et al. |
| 2008/0025976 A1 | 1/2008 | Le et al. |
| 2008/0058507 A1 | 3/2008 | Liu et al. |
| 2008/0095762 A1 | 4/2008 | Presta |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0206246 A1 | 8/2008 | Ravetch et al. |
| 2008/0219952 A1 | 9/2008 | Fischer et al. |
| 2008/0226635 A1 | 9/2008 | Koll et al. |
| 2008/0227136 A1 | 9/2008 | Pla et al. |
| 2008/0254514 A1 | 10/2008 | Knudsen |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |

(56) References Cited

U.S. PATENT DOCUMENTS

| | | |
|---|---|---|
| 2009/0069232 A1 | 3/2009 | Callewaert et al. |
| 2009/0110679 A1 | 4/2009 | Li et al. |
| 2009/0123378 A1 | 5/2009 | Wong et al. |
| 2009/0136525 A1 | 5/2009 | Gerngross et al. |
| 2009/0142828 A1 | 6/2009 | Bucciarelli et al. |
| 2009/0148513 A1 | 6/2009 | Fraunhofer et al. |
| 2009/0151023 A1 | 6/2009 | Kuvshinov et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0253174 A1 | 10/2009 | Serber et al. |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0004907 A1 | 1/2010 | Kidal et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0069617 A1 | 3/2010 | Gagnon |
| 2010/0113294 A1 | 5/2010 | Venkataraman et al. |
| 2010/0120094 A1 | 5/2010 | Johnsen et al. |
| 2010/0135987 A1 | 6/2010 | Hickman et al. |
| 2010/0136025 A1 | 6/2010 | Hickman et al. |
| 2010/0145029 A1 | 6/2010 | Gagnon |
| 2010/0151499 A1 | 6/2010 | Collins et al. |
| 2010/0160894 A1 | 6/2010 | Julian et al. |
| 2010/0167313 A1 | 7/2010 | Essig et al. |
| 2010/0172911 A1 | 7/2010 | Naso et al. |
| 2010/0189717 A1 | 7/2010 | Kim et al. |
| 2010/0221823 A1 | 9/2010 | McCoy et al. |
| 2010/0255013 A1 | 10/2010 | Presta |
| 2010/0256336 A1 | 10/2010 | Yuk et al. |
| 2010/0278808 A1 | 11/2010 | Ravetch et al. |
| 2010/0278822 A1 | 11/2010 | Fraunhofer et al. |
| 2010/0279306 A1 | 11/2010 | Bosques et al. |
| 2010/0291624 A1 | 11/2010 | Zhang et al. |
| 2010/0292443 A1 | 11/2010 | Sabbadini et al. |
| 2010/0297609 A1 | 11/2010 | Wells et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0039300 A1 | 2/2011 | Bayer et al. |
| 2011/0039729 A1 | 2/2011 | Delisa et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086050 A1 | 4/2011 | Presta |
| 2011/0086798 A1 | 4/2011 | Sethuraman et al. |
| 2011/0097336 A1 | 4/2011 | Wu et al. |
| 2011/0117601 A1 | 5/2011 | Haberger et al. |
| 2011/0123544 A1 | 5/2011 | Salfeld et al. |
| 2011/0124024 A1 | 5/2011 | Raju et al. |
| 2011/0129468 A1 | 6/2011 | Mccue et al. |
| 2011/0130544 A1 | 6/2011 | Ram et al. |
| 2011/0136682 A1 | 6/2011 | Bosques et al. |
| 2011/0171227 A1 | 7/2011 | Okun et al. |
| 2011/0207676 A1 | 8/2011 | Callewaert et al. |
| 2011/0213137 A1 | 9/2011 | Bosques et al. |
| 2011/0263828 A1 | 10/2011 | Wong et al. |
| 2011/0300151 A1 | 12/2011 | Okun et al. |
| 2011/0318340 A1 | 12/2011 | Collin et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0093810 A1 | 4/2012 | Takada et al. |
| 2012/0107783 A1 | 5/2012 | Julian et al. |
| 2012/0107874 A1 | 5/2012 | Liu et al. |
| 2012/0122076 A1 | 5/2012 | Lau et al. |
| 2012/0122759 A1 | 5/2012 | Brown et al. |
| 2012/0123688 A1 | 5/2012 | Ramasubramanyan et al. |
| 2012/0129185 A1 | 5/2012 | Maksymowych et al. |
| 2012/0134988 A1 | 5/2012 | Ravetch et al. |
| 2012/0171123 A1 | 7/2012 | Medich et al. |
| 2012/0177596 A1 | 7/2012 | Fischkoff et al. |
| 2012/0177640 A1 | 7/2012 | Burg et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0195885 A1 | 8/2012 | Correia et al. |
| 2012/0201831 A1 | 8/2012 | Salfeld et al. |
| 2012/0202974 A1 | 8/2012 | Eon-Duval et al. |
| 2012/0213792 A1 | 8/2012 | Salfeld et al. |
| 2012/0219564 A1 | 8/2012 | Salfeld et al. |
| 2012/0230913 A1 | 9/2012 | Johnston et al. |
| 2012/0238730 A1 | 9/2012 | Dong et al. |
| 2012/0244168 A1 | 9/2012 | Salfeld et al. |
| 2012/0251541 A1 | 10/2012 | Baurin et al. |
| 2012/0251550 A1 | 10/2012 | Borhani et al. |
| 2012/0258114 A1 | 10/2012 | Salfeld et al. |
| 2012/0258496 A1 | 10/2012 | Ellwanger et al. |
| 2012/0263731 A1 | 10/2012 | Fraunhofer et al. |
| 2012/0264920 A1 | 10/2012 | Wang et al. |
| 2012/0264927 A1 | 10/2012 | Parsons et al. |
| 2012/0271041 A1 | 10/2012 | Ficko Trcek |
| 2012/0276109 A1 | 11/2012 | Fraser et al. |
| 2012/0276134 A1 | 11/2012 | Fraser et al. |
| 2012/0276155 A1 | 11/2012 | Kishimoto et al. |
| 2012/0276157 A1 | 11/2012 | Fraser et al. |
| 2012/0276158 A1 | 11/2012 | Fraser et al. |
| 2012/0276160 A1 | 11/2012 | Maldonado |
| 2012/0276631 A1 | 11/2012 | Bengea et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2012/0308514 A1 | 12/2012 | Salfeld et al. |
| 2012/0309056 A1 | 12/2012 | Leon et al. |
| 2012/0329709 A1 | 12/2012 | Collins et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0149300 A1 | 6/2013 | Hiatt et al. |
| 2013/0156760 A1 | 6/2013 | Fraunhofer et al. |
| 2013/0189737 A1 | 7/2013 | Kang et al. |
| 2013/0195888 A1 | 8/2013 | Wang et al. |
| 2013/0205604 A1 | 8/2013 | Esenwein et al. |
| 2013/0231255 A1 | 9/2013 | Collins et al. |
| 2013/0243786 A1 | 9/2013 | Banerjee et al. |
| 2013/0244280 A1 | 9/2013 | Parikh et al. |
| 2013/0245139 A1 | 9/2013 | Kozlov et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |

(56) References Cited

U.S. PATENT DOCUMENTS

| | | |
|---|---|---|
| 2014/0010820 A1 | 1/2014 | Wang et al. |
| 2014/0045212 A1 | 2/2014 | Bosques et al. |
| 2014/0046032 A1 | 2/2014 | Blanche et al. |
| 2014/0065710 A1 | 3/2014 | Rives et al. |
| 2014/0072585 A1 | 3/2014 | Herigstad et al. |
| 2014/0087423 A1 | 3/2014 | Koncilja et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0199340 A1 | 7/2014 | Maldonado |
| 2014/0199729 A1 | 7/2014 | Srivastava et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271622 A1 | 9/2014 | Prentice |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0273057 A1 | 9/2014 | Prentice et al. |
| 2014/0274911 A1 | 9/2014 | Collins et al. |
| 2014/0274912 A1 | 9/2014 | Prentice |
| 2014/0275494 A1 | 9/2014 | Wang et al. |
| 2014/0288272 A1 | 9/2014 | Allison et al. |
| 2014/0288278 A1 | 9/2014 | Nti-gyabaah et al. |
| 2014/0296490 A1 | 10/2014 | Faid et al. |
| 2014/0301977 A1 | 10/2014 | Nadarajah et al. |
| 2014/0314745 A1 | 10/2014 | Rives et al. |
| 2014/0363845 A1 | 12/2014 | Sinacore et al. |
| 2014/0377275 A1 | 12/2014 | Neu et al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |
| 2015/0125905 A1 | 5/2015 | Pla et al. |
| 2015/0132320 A1 | 5/2015 | Chumsae et al. |
| 2015/0132801 A1 | 5/2015 | Ramasubramanyan et al. |
| 2015/0133639 A1 | 5/2015 | Wentz et al. |
| 2015/0139988 A1 | 5/2015 | Labkovsky et al. |
| 2015/0140006 A1 | 5/2015 | Ramasubramanyan et al. |
| 2015/0141632 A1 | 5/2015 | Markosyan |
| 2015/0158944 A1 | 6/2015 | Bengea et al. |
| 2015/0166650 A1 | 6/2015 | Ramasubramanyan et al. |
| 2015/0166653 A1 | 6/2015 | Wang et al. |
| 2015/0183865 A1 | 7/2015 | Rives et al. |
| 2015/0183866 A1 | 7/2015 | Rives et al. |
| 2015/0197579 A1 | 7/2015 | Stefan et al. |
| 2015/0210735 A1 | 7/2015 | Hickman et al. |
| 2015/0259410 A1 | 9/2015 | Ramasubramanyan et al. |
| 2015/0299249 A1 | 10/2015 | Herigstad et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328333 A1 | 11/2015 | Fraser et al. |
| 2015/0329588 A1 | 11/2015 | Wang et al. |
| 2015/0335762 A1 | 11/2015 | Fraser et al. |
| 2015/0344564 A1 | 12/2015 | Hickman et al. |
| 2015/0361169 A1 | 12/2015 | Wan et al. |
| 2015/0361170 A1 | 12/2015 | Fraunhofer et al. |
| 2016/0017030 A1 | 1/2016 | Neu et al. |
| 2016/0017281 A1 | 1/2016 | Sunstrom |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0039924 A1 | 2/2016 | Zeng |
| 2016/0039925 A1 | 2/2016 | Subramanian et al. |
| 2016/0046708 A1 | 2/2016 | Subramanian et al. |
| 2016/0068881 A1 | 3/2016 | Prentice |
| 2016/0083452 A1 | 3/2016 | Hickman et al. |
| 2016/0115193 A1 | 4/2016 | Herigstad et al. |
| 2016/0115195 A1 | 4/2016 | Mendiratta et al. |
| 2016/0122384 A1 | 5/2016 | Kim et al. |
| 2016/0138064 A1 | 5/2016 | Rives et al. |
| 2016/0145331 A1 | 5/2016 | Subramanian et al. |
| 2016/0159897 A1 | 6/2016 | Zeng |
| 2016/0185848 A1 | 6/2016 | Hossler et al. |
| 2016/0186130 A1 | 6/2016 | Pla et al. |
| 2016/0194390 A1 | 7/2016 | Ramasubramanyan et al. |
| 2016/0201028 A1 | 7/2016 | Trcek |
| 2016/0207922 A1 | 7/2016 | Tang et al. |
| 2016/0207992 A1 | 7/2016 | Bengea et al. |
| 2016/0215319 A1 | 7/2016 | Mendiratta et al. |
| 2016/0222101 A1 | 8/2016 | Fraunhofer et al. |
| 2016/0227381 A1 | 8/2016 | Bargetzi et al. |
| 2016/0237149 A1 | 8/2016 | Flikweert et al. |
| 2016/0237150 A1 | 8/2016 | Subramanian et al. |

FOREIGN PATENT DOCUMENTS

| | | |
|---|---|---|
| CN | 105777896 A | 7/2016 |
| CN | 105777904 A | 7/2016 |
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 230584 A1 | 8/1987 |
| EP | 0351789 A2 | 1/1990 |
| EP | 0366043 A1 | 5/1990 |
| EP | 374510 A1 | 6/1990 |
| EP | 453898 A2 | 10/1991 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 585705 A1 | 3/1994 |
| EP | 0612251 A1 | 8/1994 |
| EP | 0614984 A2 | 9/1994 |
| EP | 0659766 A1 | 6/1995 |
| EP | 0764719 A2 | 3/1997 |
| EP | 0956873 A2 | 11/1999 |
| EP | 0956875 A2 | 11/1999 |
| EP | 1174148 A1 | 1/2002 |
| EP | 1176195 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1568388 A1 | 8/2005 |
| EP | 1849862 A2 | 10/2007 |
| EP | 2080809 A1 | 7/2009 |
| EP | 2213726 A1 | 8/2010 |
| EP | 2305712 A1 | 4/2011 |
| EP | 2357250 A2 | 8/2011 |
| EP | 2495307 A1 | 9/2012 |
| EP | 2500414 A1 | 9/2012 |
| EP | 2528002 A2 | 11/2012 |
| EP | 2574677 A1 | 4/2013 |
| EP | 3036254 A1 | 6/2016 |
| EP | 3036320 A1 | 6/2016 |
| GB | 2160530 A | 12/1985 |
| GB | 2279077 A | 12/1994 |
| IN | 2285/MUM/2013 A1 | 1/2015 |
| JP | 6-292592 | 10/1994 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/04054 A1 | 4/1991 |
| WO | WO-91/09967 A1 | 7/1991 |
| WO | WO-92/01047 A1 | 1/1992 |
| WO | WO-92/11383 A1 | 7/1992 |
| WO | WO-92/16221 A1 | 10/1992 |
| WO | WO-92/16553 A1 | 10/1992 |
| WO | WO-92/17583 A1 | 10/1992 |
| WO | WO-93/06213 A1 | 4/1993 |
| WO | WO-93/11793 A1 | 6/1993 |
| WO | WO-94/02602 A1 | 2/1994 |

(56) References Cited

FOREIGN PATENT DOCUMENTS

| | | |
|---|---|---|
| WO | WO-94/08619 A1 | 4/1994 |
| WO | WO-94/20139 A1 | 9/1994 |
| WO | WO-94/25585 A1 | 11/1994 |
| WO | WO-94/26910 A1 | 11/1994 |
| WO | WO-94/29347 A1 | 12/1994 |
| WO | WO-95/11317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-97/04801 A1 | 2/1997 |
| WO | WO-97/13852 A1 | 4/1997 |
| WO | WO-97/29131 A1 | 8/1997 |
| WO | WO-98-08934 A1 | 3/1998 |
| WO | WO-98/23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-98/50433 A2 | 11/1998 |
| WO | WO-98/56418 A1 | 12/1998 |
| WO | WO-98/58964 A1 | 12/1998 |
| WO | WO-99/22764 A1 | 5/1999 |
| WO | WO-99/32605 A1 | 7/1999 |
| WO | WO-99/54342 A1 | 10/1999 |
| WO | WO-99/57134 A1 | 11/1999 |
| WO | WO-99/57246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-02/076578 A1 | 10/2002 |
| WO | WO-02/094192 A2 | 11/2002 |
| WO | WO-02/101019 A2 | 12/2002 |
| WO | WO-03/046162 | 6/2003 |
| WO | WO-03045995 A2 | 6/2003 |
| WO | WO-03/059935 A2 | 7/2003 |
| WO | WO-03/066662 A2 | 8/2003 |
| WO | WO-03/102132 A2 | 12/2003 |
| WO | WO-2004008100 A2 | 1/2004 |
| WO | WO-2004009776 A2 | 1/2004 |
| WO | WO-2004/026891 A2 | 4/2004 |
| WO | WO-2004/058944 A2 | 7/2004 |
| WO | WO-2004058800 A2 | 7/2004 |
| WO | WO-2004/076485 A1 | 9/2004 |
| WO | WO-2004/097006 A1 | 11/2004 |
| WO | WO-2005042569 A1 | 5/2005 |
| WO | WO-2005/062967 A2 | 7/2005 |
| WO | WO-2005/063813 A2 | 7/2005 |
| WO | WO-2005/082483 A1 | 9/2005 |
| WO | WO-2005100584 A2 | 10/2005 |
| WO | WO-2006/014683 A2 | 2/2006 |
| WO | WO-2006/026445 A1 | 3/2006 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007-005786 A2 | 1/2007 |
| WO | WO-2007/024743 A2 | 3/2007 |
| WO | WO-2007/055916 A2 | 5/2007 |
| WO | WO-2007/070315 A2 | 6/2007 |
| WO | WO-2007-077217 A2 | 7/2007 |
| WO | WO-2007/087384 A2 | 8/2007 |
| WO | WO-2007/117490 A2 | 10/2007 |
| WO | WO-2007/117505 A2 | 10/2007 |
| WO | WO-2008/008360 A1 | 1/2008 |
| WO | WO-2008/028686 A2 | 3/2008 |
| WO | WO-2008/033517 A2 | 3/2008 |
| WO | WO-2008-057240 A2 | 5/2008 |
| WO | WO-2008-057634 A2 | 5/2008 |
| WO | WO-2008068879 A1 | 6/2008 |
| WO | WO-2008/077545 A1 | 7/2008 |
| WO | WO-2008087184 A2 | 7/2008 |
| WO | WO-2008/128230 A1 | 10/2008 |
| WO | WO-2008121616 A2 | 10/2008 |
| WO | WO-2008135498 A2 | 11/2008 |
| WO | WO-2009/027041 A1 | 1/2009 |
| WO | WO-2009/017491 A1 | 2/2009 |
| WO | WO-2009023562 A2 | 2/2009 |
| WO | WO-2009058769 A1 | 5/2009 |
| WO | WO-2009/073569 A2 | 6/2009 |
| WO | WO-2009/079382 A1 | 6/2009 |
| WO | WO-2009135656 A1 | 11/2009 |
| WO | WO-2010/036443 A1 | 4/2010 |
| WO | WO-2010-048183 A1 | 4/2010 |
| WO | WO-2010043703 A1 | 4/2010 |
| WO | WO-2010/080062 A1 | 7/2010 |
| WO | WO-2010/102114 A1 | 9/2010 |
| WO | WO-2010/111633 A2 | 9/2010 |
| WO | WO-2010122460 A1 | 10/2010 |
| WO | WO-2010/129469 A1 | 11/2010 |
| WO | WO-2010127069 A1 | 11/2010 |
| WO | WO-2010/136209 A1 | 12/2010 |
| WO | WO-2010/138502 A2 | 12/2010 |
| WO | WO-2010/141039 A1 | 12/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011133902 A2 | 10/2011 |
| WO | WO-2011134919 A2 | 11/2011 |
| WO | WO-2011134920 A1 | 11/2011 |
| WO | WO-2012/014183 A1 | 2/2012 |
| WO | WO-2012019160 A2 | 2/2012 |
| WO | WO-2012030512 A1 | 3/2012 |
| WO | WO-2012/046255 A2 | 4/2012 |
| WO | WO-2012050175 A1 | 4/2012 |
| WO | WO-2012051147 A1 | 4/2012 |
| WO | WO-2012/065072 A2 | 5/2012 |
| WO | WO-2012/068134 A1 | 5/2012 |
| WO | WO-2012062810 A2 | 5/2012 |
| WO | WO-2012/078376 A1 | 6/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A2 | 11/2012 |
| WO | WO-2012158551 A1 | 11/2012 |
| WO | WO-2013-009648 A2 | 1/2013 |
| WO | WO-2013-011076 A2 | 1/2013 |
| WO | WO-2013006461 A1 | 1/2013 |
| WO | WO-2013006479 A2 | 1/2013 |
| WO | WO-2013013013 A2 | 1/2013 |
| WO | WO-2013/021279 A2 | 2/2013 |
| WO | WO-2013-066707 A1 | 5/2013 |
| WO | WO-2013/067301 A2 | 5/2013 |
| WO | WO-2013/095966 A1 | 6/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-164837 A1 | 11/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013/181585 A2 | 12/2013 |
| WO | WO-2013-186230 A1 | 12/2013 |
| WO | WO-2014/018747 A2 | 1/2014 |
| WO | WO-2014/039903 A2 | 3/2014 |
| WO | WO-2014/052360 A2 | 4/2014 |
| WO | WO-2014/096672 A1 | 6/2014 |
| WO | WO-2014/099636 A1 | 6/2014 |
| WO | WO-2014/125374 A2 | 8/2014 |
| WO | WO-2014-149935 A1 | 9/2014 |

(56) References Cited

FOREIGN PATENT DOCUMENTS

| | | |
|---|---|---|
| WO | WO-2014/150655 A1 | 9/2014 |
| WO | WO-2014/151878 A2 | 9/2014 |
| WO | WO-2014/158231 A1 | 10/2014 |
| WO | WO-2014/159488 A1 | 10/2014 |
| WO | WO-2014/159494 A1 | 10/2014 |
| WO | WO-2014/159499 A1 | 10/2014 |
| WO | WO-2014/179601 A2 | 11/2014 |
| WO | WO-2014-196780 A1 | 12/2014 |
| WO | WO-2014/207763 A1 | 12/2014 |
| WO | WO-2015/004679 A1 | 1/2015 |
| WO | WO-2015/007912 A1 | 1/2015 |
| WO | WO-2015/051293 A2 | 4/2015 |
| WO | WO-2015/073884 A2 | 5/2015 |
| WO | WO-2015/115849 A1 | 8/2015 |
| WO | WO-2016/007764 A1 | 1/2016 |
| WO | WO-2016/102383 A1 | 6/2016 |

OTHER PUBLICATIONS

"Genentech unveils production capacity hikes," in-Pharma Technologist.com Jun. 28, 2005, pp. 1-2.

"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS, 28 pages.

"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS, 22 pages.

"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS, 21 pages.

"Memorandum in Support of Centocor's Motion No. 3 for Summary Judgment that the 394 and 031 Patents Are Invalid for Under 35 U.S.C. §102(f) for Failing to Name the Proper Inventors", dated Aug. 1, 2013 and submitted by defendant in Civil Action No. 09-40089-FDS, 13 pages.

"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.

"Plaintiffs' Memorandum in Support of Their Motion for Partial Summary Judgment", dated Aug. 1, 2013 and submitted by plaintiff in Civil Action No. 09-40089-FDS, 49 pages.

"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.

Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.

Abraham, E., et al., "Efficacy and Safety of Monoclonal Antibody to Human Tumor Necrosis Factor α in Patients with Sepsis Syndrome," *JAMA*, vol. 273(12):934-941 (1995).

Adams. et al., "Aggressive cutaneous T-cell lymphomas after TNFα blockade," J. Am. Acad. Dermatol 2004;51 :660-2.

Ahmed, M. U.et al.; N-(Carboxyethyl)lysine, a product of the chemical modification of proteins by methylglyoxal, increases with age in human lens proteins; Biochem. J. 1997, 324, 565-570.

Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.

Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.

Ahmed, N.; Thornalley, P. J.; Advanced glycation endproducts: what is their relevance to diabetic complications?; Diabetes, Obes. Metab. 2007, 9, 233-245.

Alessandri, L. et al., "Increased serum clearance of *oligomannose* species present on a human IgG1 molecule." *mAbs*, (2012), 4(4); 509-520.

Alfaro, J. F.; Chemo-Enzymatic Detection of Protein Isoaspartate Using Protein Isoaspartate Methyltransferase and Hydrazine Trapping; Anal. Chem. 2008, 80, 3882-3889.

Alfaro, J. F.; Synthesis of LuxS Inhibitors Targeting Bacterial Cell-Cell Communication; Org. Lett. 2004, 6, 3043-3046.

Altamirano, C., et al., "Strategies for fed batch cultivation of t-PA producing CHO cells: substitution of glucose and glutamine and rational design of culture medium", *J. Biotechn*. 110:171-179, 2004.

An, Zhiqiang editor, "Therapeutic Monoclonal Antibodies: From Bench to Clinic," 2009 edition, John Wiley & Sons, Hoboken, NJ, US, pp. 73-76, section 3.4.3.

Andersen DC, The effect of cell-culture conditions on the oligosaccharide structures of secreted glycoproteins. Curr Opin Biotechnol. Oct. 1994;5(5):546-9.

Anonymous, "SACHEM Displacement Chromatography," Aug. 29, 2012, Retrieved from the internet: displacementchromatography.com. Last accessed on Jul. 30, 2014, 12 pages.

Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.

Anumula et al., "Quantitative glycan profiling of normal human plasma derived immunoglobulin and its fragments Fab and FcO" (2012) J. Immunol. Methods, 382:167-176.

Arend et al., "Inhibition of the production and effects of interleukins-1 and tumor necrosis factor α in rheumatoid arthritis" (1995) Arth. Rheum., 38(2):151-160.

Ashkenazi et al., "Immunoadhesins: An alternative to human monoclonal antibodies" (1995) Methods, 8(2): 104-115.

Averginos, Gab '04 Abstracts—GE Healthcare Life Sciences, "HUMIRA manufacturing: challenges and the path taken", France, Oct. 3-5, 2004, published 2005, pp. 14-16.

Avgerinos et al. (GAb '04 Abstracts—GE Healthcare Life Sciences, France Oct. 3-5, 2004, pp. 15-16 published 2005).

Awdeh, Z.L., A.R. Williamson, and B.A. Askonas, One cell-one immunoglobulin. Origin of limited heterogeneity of myeloma proteins. Biochem J, 1970. 116(2): p. 241-8.

Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.

Babcock, James et al., "Partial Replacement of Chemically Defined Media with Plant-Derived Protein Hydrolysates," *BioPharm International*, vol. 23: Jun. 6, 2010, 6 pages.

Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.

Bandyopadhyay S., et al. Physicochemical and functional characterization of a biosimilar adalimumab ZRC-3197, Biosimilars, 2015;5, pp. 1-18.

Barb et al., "Branch-specific sialylation of IgG-Fc glycans by ST6Gal-I" Biochemistry, (2009) 48:9705-9707.

Barbuto, J. et al. "Production of Neutralizing Antibodies to Tumor Necrosis Factor by Human Tumor-Infiltrating B Lymphocytes" *Proc. Am. Assoc. Cancer Res,*. 34:487, Abstr. 2904 (1993).

Barnes et al., "Stability of Protein Production from Recombinant Mammalian Cells," Biotechnology and Bioengineering, 81:6, Mar. 20, 2003, pp. 631-639.

Bartelds et al., "Development of antidrug antibodies against adalimumab and association with disease activity and treatment failure during long-term follow-up" (2011) JAMA, 305(14):1 460-1468.

BD Bioscience Product Description for BBL Phytone Peptone (Advanced Processing, Third Edition) (Sep. 23, 2010) Retrieved

(56) References Cited

OTHER PUBLICATIONS from the internet: bdbiosciences.com/external_files/Doc_Recon_2.0/ab/others/Phytone_Soytone.pdf. Last accessed on Jan. 8, 2015, 4 pages.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Bertolini et al., Stimulation of bone resorption and inhibition of bone formation in vitro by human tumour necrosis factors, (1986) Nature 319:516-518.
Biblia, T.A. et al., "In Pursuit of the Optimal Fed-Batch Process for Monoclonal Antibody Production", Biotechnol. Prog 11(1):1-13, Jan.-Feb. 1995.
Birch, Jr. et al., "Antibody production", Adv. Drug Delivery Reviews 58:671-685, 2006.
Bird et al. "Single-chain antigen-binding proteins." Science. (1988) 242:423-426.
Blaker, GJ, et al., "The Glucose, Insulin and Glutamine Requirements of Suspension Cultures of HeLa Cells in a Defined Culture Medium", J. Cell Sci. 9:529-537, 1971.
Biastoff, S.; et al.; Colorimetric Activity Measurement of a Recombinant Putrescine N-Methyltransferase from *Datura stramonium*; Planta Med. 2006, 72, 1136.
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-248.
Boswell et al. "Effects of Charge on Antibody Tissue Distribution and Pharmacokinetics" Bioconjugate Chem.(21) 2153-2163 (2010).
Boyle, P. et al. "A Novel Monoclonal Human IgM Autoantibody which Binds Recombinant Human and Mouse Tumor Necrosis Factor-α" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).
Brock, Jonathan et al., "Detection and identification of arginine modifications on methylglyoxal-modified ribonuclease by mass spectrometric analysis," Journal of Mass Spectrometry, 2007; 42:89-100.
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice," Cur. Op. Biotechnol. vol. 8;455-458 (1997).
Bruggemann, M., Neuberger, M.S., "Strategies for expressing human antibody repertoires in transgenic mice," *Immunol. Today* 17:391-397 (1996).
Burteau et al. "Fortification of a Protein-Free Cell Culture Medium With Plant Peptones Improves Cultivation and Productivity of an Interferon-γ-Producing CHO Cell Line," In Vitro Cell Dev Biol—Animal, Jul. / Aug. 2003. 39-291-296.
Byun, et al. Archives of Biochemistry and Biophysics, "Transport of anti-IL-6 binding fragments into cartilage and the effects of injury," 532 (2013), pp. 15-22.
Cai B, et al. "C-Terminal Lysine Processing of Human Immunoglobulin G2 Heavy Chain In Vivo" Biotechnol. Bioeng. 2011;108: 404-412.

Cambridge Antibody Technology, advertisement of phage display services, Science vol. 253, No. 5018 (1991).
Carter et al., "Humanization of an anti-p185HER2 antibody for human cancer therapy," *Proc. Nat. Acad. Sci*89:4285-4289 (1992).
Chang KH, et al., "N-Acetylcysteine Increases the Biosynthesis of Recombinant EPO in Apoptotic Chinese Hamster Ovary Cells", Free Radic Res. 30(2):85-91, 1999.
Chang, T. & Wu, L., Methylglyoxal, oxidative street, and hypertension, Can. J. Physiol.Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.
Chaplen, F.W.R., Incidence and potential implications of the toxic metabolite methylglyoxal in cell culture: A review, Cytotechnology 26: 173-183, 1998.
Chaplen, FWR; A dissertation entitled Analysis of Methylglyoxal Metabolism in Mammalian Cell Culture; Univ. of Wisconsin—Madison 1996, 218 pages.
Charter, Edward A., "A New Process for the Separation and Purification of Egg Yolk; Antibodies," BASc., The University of British Columbia; A Thesis; Apr. 1993, 163 pages.
Chelius, D. et al.; Identification and Characterization of Deamidation Sites in the Conserved Regions of Human Immunoglobulin Gamma Antibodies, Anal. Chem. 2005, 77,6004-6011.
Choo et al. "High-level production of a monoclonal antibody in murine myeloma cells by perfusion culture using a gravity settler" Biotechnology Progress, vol. 23, No. 1, Jan. 1, 2007, 225-231.
Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).
Chua, FKF et al., "Hyper-stimulation of monoclonal antibody production by high osmolarity stress in eRDF medium", J. Biotechnology 37(3):265-275, Nov. 15, 1994.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009. 81(15): p. 6449-57.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013(Dec. 3, 2013), pp. 11401-11409.
Chung et al., "Utilization of Lysozyme Charge Ladders to Examine the Effects of Protein Surface; Charqe Distribution on Bindinq Affinity in Ion Exchanqe Systems," Lanqmuir 26(2): 759-768 (2010).
Chung et al. "Cetuximab-induced anaphylaxis and IgE specific for galactose-a-1,3-galactose" NEJM 358:11, 1109-1117 (2008).
Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).
Clincke et al. "Effect of iron sources on the glycosylation macroheterogeneity of human recombinant IFN-γ produced by CHO cells during batch processes," BMC Proceedings (Nov. 22, 2011) 5(Suppl 8):PI14, pp. 1-2.
Clincke et al. "Characterization of metalloprotease and serine protease activities in batch CHO cell cultures: control of human recombinant IFN-γ proteolysis by addition of iron citrate," BMC Proceedings (Nov. 22, 2011) 5(Suppl 8):P115, pp. 1-3.
Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.
Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).

(56) References Cited

OTHER PUBLICATIONS

Cordoba, A.J., et al., Non-enzymatic hinge region fragmentation of antibodies in solution. Journal of Chromatography B, 2005. 818(2): p. 115-121.
Cox, J. et al. "A directory of human germ-line Vκ segments reveals a strong bias in their usage" *Eur. J. Immunol.*, 24(2):827-36 (1994).
Cromwell, "Avastin: highlights from development," GAB'04 Abstracts—GE Healthcare Life Sciences, Franc Oct. 3-5, 2004, pp. 17-18 published 2005.
Crowell, C.K., et al., Amino acid and manganese supplementation modulates the glycosylation state of erythropoietin in a CHO culture system. Biotechnology and bioengineering, Feb. 15, 2007; 96(3):538-549.
Cygnus Technologies, Anti-CHO HCP. Retrieved from the internet: cygnustechnologies.com/product_detail/host-cell-protein-antibodies/anti-cho-h . . . Last accessed on Apr. 18, 2012, 1 page.
Dai, S.; An Integrated Proteomic Analysis of Major Isoaspartyl-Containing Proteins in the Urine of Wild Type and Protein LIsoaspartate O-Methyltransferase-Deficient Mice; Anal. Chem. 2013, 85, 2423-2430.
Das et al., "Delivery of rapamycin-loaded nanoparticle down regulates ICAM-1 expression and maintains an immunosuppressive profile in human CD34+ progenitor-derived dendritic cells" (2008) J Biomed Mater Res A., 85(4):983-92.
Daugherty, et al. Formulation and Delivery Issues for Monoclonal Antibody Therapeutics. Advanced Drug Delivery Reviews, 2006. vol. 58, pp. 686-706.
Davies et al., "Antibody VH domains as small recognition units." *Biotechnology*, 13:475-479 (1995).
Department of Surgery, University of Toronto, Annual Report (1998-1999)(326 pages).
DePhillips et al., "Determinants of protein retention characteristics on cation-exchange adsorbents,"; Journal of Chromatograph A, 933:57-72 (2001).
DeZongotita et al., "Phosphate feeding improves high-cell-concentration NS0 myeloma cell culture performance for monoclonal antibody production" Biotechnology and Bioengineering. 2000, 69: 566-576.
Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.
Dionex Application Note 125 Monitoring Protein Deamidation by Cation-Exchange Chromatography. 2009; pp. 1-7.
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).
Doring, E., "Identification and Characterization of a TNFa Antagonist Derived from a Monoclonal Antibody" (1994) *Mol. Immunol* .31(14): 1059-1067.
Drew, Berry et al., "The Effects of Media Formulations on the Biochemical Profile of IgG Expressed in Sp2/0 Cells as Measured by Cation Exchange HPLC," European Society of Animal Cell Technology Meeting Jan. 2007, Poster #1115, 1 page.
Du et al., "Chromatographic analysis of the acidic and basic species of recombinant monoclonal antibodies" MAbs, Sep.-Oct. 2012; 4(5):578-85.
Eason et al., "Inhibition of the effects of Tnf in renal allograft recipients using recombinant human dimeric tumor necrosis factor receptors" (1995) Transplantation, 59(2):300-305.
Ebersbach et al., "Affilin-novel binding molecules based on human gamma-B-crystallin, an all beta-sheet protein" (2007) J. Mol. Biol., 372 (1): 172-85.

Elliot et al., "Randomised double-blind comparison of chimeric monoclonal antibody to tumour necrosis factor alpha (cA2) versus placebo in rheumatoid arthritis" (1994) Lancet, 344(8930):1105-1110.
Elliot et al., "Repeated therapy with monoclonal antibody to tumour necrosis factor α (cA2) in patients with rheumatoid arthritis" (1994) *Lancet*, 344:1125-1127.
Elliot, "Treatment of rheumatoid arthritis with chimeric monoclonal antibodies to tumor necrosis factor α" (1993) *Arthritis & Rheumatism*, 36(12):1681-1690.
Ellison, Jay W. et al., "The Nucleotide Sequence of a Human Immunoglobulin Cγ1 Gene," Nucleic Acids Research, vol. 10, No. 13 (1982), pp. 4071-4079.
Emery, P. "Adalimumab therapy: Clinical findings and implications for integration into clinical guidelines for rheumatoid arthritis." *Drugs of Today*, 41(3): p. 155-163. (2005).
ERBITUX (cetuximab) label, *Revised* Aug. 2013, 8 pages.
European Medicines Agency (EMA Europe), "2004 Report on Scientific Discussion for the Approval of Humira™ (adalimumab)," Retrieved from the internet: ema.europa.eu/docs/en_GB/document_library/EPAR_Scientific_Discussion/human/000481/ WC500050867.pdf <http://www.ema.europa.eu/docs/en_GB/document_library/EPAR_Scientific_Discussion/human/000481/ WC500050867.pdf>. Last accessed on Nov. 12, 2014, 25 pages.
Ewert et al., "Biophysical Properties of Human Antibody Variable Domains," J. Mol. Biol. 324: 531-553 (2003).
Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*, 50 pages.
Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.N.Y., 90 pages.
Exhibit dated Aug. 1, 2013 and cited by plaintiff in Civil Action No. 09-40089-FDS providing excerpts from the File History of U.S. Appl. No. 12/578,487, 5 pages.
Exhibit dated Aug. 1, 2013 and cited by defendant in Civil Action No. 09-40089-FDS providing the Jun. 24, 2009 trial transcript of the AM session in the matter of *Centocor, et al.* v. *Abbott Laboratories*, E.D. TX., 42 pages.
Exhibit dated Aug. 1, 2013 and cited by defendant in Civil Action No. 09-40089-FDS providing the Sep. 20, 2012 Day 8 trial transcript in the matter of *Abbott* v. *Centocor Ortho Biotech Inc*., D. MA., 71 pages.
Exhibit dated Aug. 1, 2013 and cited by plaintiff in Civil Action No. 09-40089-FDS providing Declaration by Jochen Salfeld, dated Jan. 17, 2013, 40 pages.
Extended European Search Report for Application No. 13877986.3. Dated Aug. 4, 2014, 11 pages.
Fahrner et al., "Industrial purification of pharmaceutical antibodies: development, operation, and validation of chromatography processes" Biotechnology and Genetic Engineering Reviews, 18, 2001, pp. 301-327.
Fava et al., "Critical role of peripheral blood phagocytes and the involvement of complement in tumour necrosis factor enhancement of passive collagen-arthritis" (1993) Clin. Exp. Immunol., 94(2):261-266.
FDA Package insert for Adalimumab, Sep. 26, 2003, pp. 1-16.
Feldmann, "Anti-TNF-alpha Therapy of Rheumatoid Arthritis: What Have We Learned?" (2001) *Annu. Rev. Immunol*., 19:163-196.
Felver et al., "Plasma tumor necrosis factor α predicts decreased long-term survival in severe alcoholic hepatitis" (1990) Alcohol. Clin. Exp. Res. 14(2):255-259.
Fernandes, "Demonstrating Comparability of Antibody Glycosylation during Biomanufacturing," European Biopharmaceutical Review. (2005) pp. 106-110.
Fietze et al., "Cytomegalovirus infection in transplant recipients the role of tumor necrosis factor" (1994) Transplantation, 58(6):675-680.
Figini, "In Vitro assembly of Repertoires of Antibody Chains on the Surface of Phage by Renaturation" (1994) *J. Mol. Biol*., 239:68-78.

(56) References Cited

OTHER PUBLICATIONS

Fishwild et al., "High-avidity human IgG kappa monoclonal antibodies from a novel strain of minilocus transgenic mice" (1996) *Nature Biotechnology*, 14:845-851.

Fleisher B., Mechanism of glycosylation in the Golgi apparatus. J Histochem Cytochem, Aug. 1983; 31 (8):1033-1040.

Folk et al., "Carboxypeptidase B, Purification and Characterization of the Porcine Enzyme," J. Biological Chem, 1960, 235:2272-2277.

Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.

Foote, J., "Antibody framework residues affecting the conformation of the hypervariable loops" (1992) *J. Mol .Biol.*, 224(2):487-499.

Freitag et al., "Displacement chromatography in biotechnological downstream processing," J. Chromatography, (1995) 691(1):101-112.

Gagnon et al., "A Systematic Approach to the Purification of Monoclonal Antibodies," *LC-GC* 11 (1):26-34 (1993).

Gagnon, P., "Polishing methods for monoclonal IgG purification" Chapter 17, Taylor & Francis Group, LLC, pp. 491-505, 2007.

Gao et al. "Site-selective modifications of arginine residues in human hemoglobin induced by methylglyoxal." Biochemistry, 2006; pp. 15654-15660.

Gatto, B. "Biologics targeted at TNF: design, production and challenges", Reumatismo 58(2):94-103, 2006.

Gauthier, M. A.& Klok, H.-A. Arginine-Specific Modification of Proteins with Polyethylene Glycol Biomacromolecules; 2011, 12, 482-493.

Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.

Genbank Entry for CHO Cathepsin L., EGW13555, Aug. 25, 2011, pp. 1-2.

Ghaderi, et al., "Implications of the Presence of N-glycolylneuraminic acid in Recombinant Therapeutic Glycoproteins", *Nature Biotechnology*, 28(8):863-868 (2010).

Ghaderi, et al., "Production platforms for biotherapeutic glycoproteins. Occurrence, impact, and challenges of non-human sialylation", *Biotechnology and Genetic Engineering Reviews*, 28:147-176 (2012).

Gilar et al., "Characterization of glycoprotein digests with hydrophilic interaction chromatography and mass spectrometry" (2011) Analytical Biochem., 417:80-88.

Giroir et al., "Inhibition of tumor necrosis factor prevents myocardial dysfunction during burn shock" (1994) Am. J. Physiol., 267(1 Pt 2):H118-24.

Goetze, A. et al., "High-mannose glycans on the Fc region of therapeutic IgG antibodies increase serum clearance in humans." *Glycobiology* (2011), 21(7); 949-959.

Gonzalez et al. "Purification of Lactic Acid from Fermentation Broths by Ion-Exchange Resins" Ind. Eng. Chem. Res. 45:3243-3247 (2006).

Goochee CF the Oligosaccharides of Glycoproteins: Bioprocess Factors Affecting Oligosaccharide Structure and their Effect on Glycoprotein Properties. Nature Biotechnology Dec. 1991, vol. 9. 1346-1355.

Goochee, C.F. "Bioprocess Factors Affecting Glycoprotein Oligosaccharide Structure." *Develop. Biol. Standard*, vol. 76 (1992). 95-104.

Goswami et al., "Developments and Challenges for mAb-Based Therapeutics," *Antibodies*, 2:452-500, 2013.

Grabulovski et al., "A Novel, Non-immunogenic Fyn SH3-derived Binding Protein with Tumor Vascular Targeting Properties" (2007) J Biol Chem 282, (5): 3196-3204.

Graf et al., "Ion exchange resins for the purification of monoclonal antibodies from animal cell culture" Bioseparation 4 (1) :7-20 (Feb. 1994).

Gram et al., "In vitro selection and affinity maturation of antibodies from a naive combinatorial immunoglobulin library" (1992) *PNAS*, 89:3576-3580.

Gramer et al. "Modulation of antibody galactosylation through feeding of uridine, manganese chloride, and galactose," Biotechnology and Bioengineering. (Jul. 1, 2011) 108(7):1591-1602.

Gramer et al., "Glycosidase Activities of the 293 and NS0 Cell Lines, and of an Antibody-Producing Hybridoma Cell Line", *Biotechnology and Bioengineering*, 43:423-428 (1994).

Gramer, M.J., et al., "Manipulation of Antibody Glycoforms in a High-Yield GS-CHO Process to Meet Comparability Requirements", *GenMab*, 1 page.

Green et al., "Antigen-specific human monoclonal antibodies from mice engineered with human Ig heavy and light chain YACs" (1994) *Nature Genetics*, 7:13-21.

Griffiths et al., "Isolation of high affinity human antibodies directly from large synthetic repertoires" (1994) *EMBO J.*, 13:3245-3260.

Griffiths, "Human anti-self antibodies with high specificity from phage display libraries" (1993) *The EMBO J.* 12(2):725-34.

Gross et al. "Involvement of various organs in the initial plasma clearance of differently glycosylated rat liver secretory proteins," Eur. J. Biochem. (1988) 173(3):653-659.

Grosvenor, Sally, "A New Era in Cell Culture Media Development," *BioPharm International*, Jul. 2012 vol. 25: 7, pp. 1-7.

Grunberg, J. et al., "High-Yield Production of Recombinant Antibody Fragments in HEK-293 Cells Using Sodium Butyrate", BioTechniques 34(5):968-972, May 2003.

Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.

Guile et al., "A rapid high-resolution high-performance liquid chromatographic method for separating glycan mixtures and analyzing oligosaccharide profiles" (1996) Anal Biochem., 240(2):210-26.

Haddadi et al., "Delivery of rapamycin by PLGA nanoparticles enhances its suppressive activity on dendritic cells" (2008) J Biomed Mater Res A., 84A(4):885-98.

Hansen et al., "The role of tumor necrosis factor-alpha in acute endotoxin-induced hepatotoxicity in ethanol-fed rats" (1994) Hepatology, 20(2):461-474.

Harding et al., "Class switching in human immunoglobulin transgenic mice" (1995) Ann. NY Acad. Sci., 764:536-546.

Harlow and Lane, Antibodies A Laboratory Manual, Purification of Antibodies by using a; Deae-matrix (Batch), Storing and Purifying Antibodies; Chapter 8: 302-303 (1988).

Harlow et al., Eds "Antibodies: A Laboratory Manual" 1988. Cold Spring Harbor Laboratory Press, Chapter 7, pp. 245, 247,and 253.

Harris, "Processing of C-terminal lysine and arginine residues of proteins isolated from mammalian cell culture" Journal of Chromatography, (1995) 705; 129-134.

Harris, R.J., et al., Identification of multiple sources of charge heterogeneity in a recombinant antibody. Journal of Chromatography B: Biomedical Sciences and Applications, 2001. 752(2): p. 233-245.

Harris, Reed J. et al., "Structural Characterization of a Recombinant CD4-IgG Hybrid Molecule," Eur. J. Biochem. 194:611-620 (1990).

Harrison et al., "Protein N-Glycosylation in the Baculovirus—Insect Cell Expression System and; Engineering of Insect Cells to Produce "Mammalianized" Recombinant Glycoproteins," Advances in; Virus Research, 68:159-191 (2006).

Hawkins, "Selection of Phage Antibodies by Binding Affinity Mimicking Affinity Maturation" (1992) *J. MoL Biol.*, 226:889-896.

Heidemann, R. et al., "The use of peptones as medium additives for the production of a recombinant therapeutic protein in high density perfusion cultures of mammalian cells", Cytotechnology 32:157-167, 2000.

Helms et al., "Destabilizing loop swaps in the CDRs of an immunoglobulin VL domain," Protein; Science 4:2073-2081 (1995).

Hiatt et al., "Characterization and Applications of Antibodies Produced in Plants", *Intern. Rev. Immunol.*, 10:139-152 (1993).

Hiatt et al., "Production of Antibodies in Transgenic Plants", *Nature*, 342:76-78 (1989).

(56) References Cited

OTHER PUBLICATIONS

Hillgren, A. et al., "Protection mechanism of Tween 80 during freeze-thawing of a model protein LDH," *International Journal of Pharmaceutics*, vol. 237:57-69 (2002).

Hills, A.E. et al., Metabolic control of recombinant monoclonal antibody N-glycosylation in GS-NS0 cells, Biotechnology and Bioengineering, Oct. 20, 2001; 75(2):239-251.

Hipkiss, A.; Can the beneficial effects of methionine restriction in rats be explained in part by decreased methylglyoxal generation resulting from suppressed carbohydrate metabolism?; Biogerontology 2012, 13, 633-636.

Hober, et al. "Protein A chromatography for antibody purification", J. Chromatography B, vol. 848 (2007) pp. 40-47.

Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).

Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.

Holt, L. et al., "Domain antibodies: proteins for therapy," Trends in Biotechnology, vol. 21(11):484-490 (2003).

Hoogenboom et al., "By-passing immunisation: Human antibodies from synthetic repertoires of germline VH gene segments rearranged in vitro" (1992) *J. Mol. Biol.*, 227:381-388.

Hoogenboom, "Converting rodent into human antibodies by guided selection" (1996) *Antibody Engineering*, Oxford University Press, pp. 169-185.

Horvath et al: "Characterization of a Monoclonal Antibody Cell Culture Production Process Using a Quality by; Design Approach", Molecular Biotechnology, vol. 45, No. 3, Jul. 1, 2010, pp. 203-206.

Hossler et al., "Optimal and consistent protein glycosylation in mammalian cell culture", Glycobiology; (2009), 19(9):936-949.

Hossler et al.; "Improvement of mammalian cell culture performance through surfactant enabled concentrated feed media"; Biotechnology Progress; 29(4):1023-1033 (2013).

Hossler, Patrick et al., "Targeted Shifting of Protein Glycosylation Profiles in Mammalian Cell Culture through Media Supplementation of Cobalt." *J. Glycobiol* vol. 3; 1.(2014). 9 pages.

Huang et al. "Effects of anti-TNF monoclonal antibody infusion in patients with hairy cell leukaemia" (1992) *Br. J. Haematol.*, 81(2):231-234.

Huang, L., et al., In Vivo Deamidation Characterization of Monoclonal Antibody by LC/MS/MS. Analytical Chemistry, 2005. 77(5): p. 1432-1439.

HUMIRA (adalimumab) label, *Revised* Sep. 2013, 87 pages.

HUMIRA (adalimumab) prescribing information, Dec. 20, 2002, pp. 1-16.

Huse, "Generation of a large combinatorial library of the immunoglobulin repertoire in phage lambda" (1989) *Science*, 246:1275-81.

Hussain et al., "Hepatic expression of tumour necrosis factor-alpha in chronic hepatitis B virus infection" (1994) J. Clin. Pathol., 47:1112-1115.

Huston et al. "Protein engineering of antibody binding sites: recovery of specific activity in an anti-digoxin single-chain Fv analogue produced in *Escherichia coli*," Proc. Natl. Acad. Sci. USA(1988) 85:5879-5883.

HyClone™ CDM4CHO Catalog listing (last accessed Nov. 17, 2014).

ICH Topic Q6B "Specifications: Test Procedures and Acceptance Criteria for Biotechnological/Biological Products," Sep. 1999, pp. 1-17.

Indian Patent Office—IPAIRS application status for 2285/MUM/2013—Application not yet published. Document found on internet at ipindiaonline.gov/in/patentsearch/search/index.aspx. Last accessed Apr. 13, 2015.

International Preliminary Report on Patentability for Application No. PCT/US07/08359, dated Dec. 12, 2011, 5 pages.

International Preliminary Report on Patentability for Application No. PCT/US2011/060388, dated May 30, 2012, 9 pages.

International Preliminary Report on Patentability for Application No. PCT/US2013/031352 dated Nov. 25, 2014, pp. 1-10.

International Preliminary Report on Patentability for Application No. PCT/US2013/031365, dated Mar. 3, 2015, 9 pages.

International Preliminary Report on Patentability for Application No. PCT/US2013/031380, dated Sep. 15, 2015, 13 pages.

International Preliminary Report on Patentability for Application No. PCT/US2013/031389, dated Oct. 21, 2014, pp. 1-10.

International Preliminary Report on Patentability for Application No. PCT/US2013/031485, dated Oct. 21, 2014, pp. 1-8.

International Preliminary Report on Patentability for Application No. PCT/US2013/031681, dated Oct. 21, 2014, pp. 1-8.

International Preliminary Report on Patentability for Application No. PCT/US2013/041954, dated Nov. 25, 2014, pp. 1-14.

International Preliminary Report on Patentability for Application No. PCT/US2013/041958, dated Dec. 4, 2014, pp. 1-2.

International Preliminary Report on Patentability for Application No. PCT/US2013/065720, dated Sep. 24, 2015, 8 pages.

International Preliminary Report on Patentability for Application No. PCT/US2013/065749 dated Sep. 15, 2015, 10 pages.

International Preliminary Report on Patentability for Application No. PCT/US2013/065797, dated Sep. 24, 2015, 8 pages.

International Preliminary Report on Patentability for Application No. PCT/US2013/069702, dated Sep. 15, 2015, 8 pages.

International Preliminary Report on Patentability for Application No. PCT/US2014/024151, dated Sep. 15, 2015, 9 pages.

International Preliminary Report on Patentability for Application No. PCT/US2014/024256, dated Sep. 15, 2015, pp. 1-9.

International Preliminary Report on Patentability for Application No. PCT/US2014/026606, dated Sep. 15, 2015, 13 pages.

International Preliminary Report on Patentability for Application No. PCT/US2014/026636, dated Sep. 15, 2015, 9 pages.

International Preliminary Report on Patentability for Application No. PCT/US2014/059127, dated Apr. 14, 2016, 15 pages.

International Preliminary Report on Patentability for Application No. PCT/US2014/065793, dated May 17, 2016, 13 pages.

International Search Report and Written Opinion for Application No. PCT/US2008/085066, dated May 12, 2009, 5 pages.

International Search Report and Written Opinion for Application No. PCT/US2010/033387, dated Aug. 7, 2012, 10 pages.

International Search Report and Written Opinion for Application No. PCT/US2013/031380, dated Feb. 5, 2014, 162 pages.

International Search Report and Written Opinion for Application No. PCT/US2013/041954, dated Dec. 17, 2013, 21 pages.

International Search Report and Written Opinion for Application No. PCT/US2013/041958, dated Dec. 17, 2013, 21 pages.

International Search Report and Written Opinion for Application No. PCT/US2013/065720, dated Dec. 16, 2013, 14 pages.

International Search Report and Written Opinion for Application No. PCT/US2013/065797, dated Nov. 26, 2013, 14 pages.

International Search Report and Written Opinion for Application No. PCT/US2014/058991, completed Dec. 18, 2014, 15 pages.

International Search Report and Written Opinion for Application No. PCT/US2014/065793, dated Jul. 27,2015, 20 pages.

International Search Report and Written Opinion for PCT/US2012/035266, dated Feb. 7, 2013, 4 pages.

International Search Report and Written Opinion from PCT/US2013/065749 dated Mar. 18, 2014, 18 pages.

International Search Report and Written Opinion from PCT/US2014/024151 dated Aug. 7, 2014, pp. 1-16.

International Search Report and Written Opinion from PCT/US2015/039773 dated Sep. 25, 2015, pp. 1-14.

International Search Report and Written Opinion from PCT/US2015/042846 dated Feb. 2, 2016, pp. 1-22.

International Search Report for Application No. PCT/IB03/04502, dated May 26, 2004, 6 pages.

International Search Report for Application No. PCT/US2011/060388 dated May 30, 2012, 6 pages.

(56) References Cited

OTHER PUBLICATIONS

International Search Report for Application No. PCT/US2013/031352, Dated Apr. 25, 2013, 6 pages.
International Search Report for Application No. PCT/US2013/031389, Dated Jun. 3, 2013, 4 pages.
International Search Report for Application No. PCT/US2013/031485, Dated Jun. 25, 2013, 4 pages.
International Search Report for Application No. PCT/US2013/031681, Dated Jun. 14, 2013, 6 pages.
International Search Report for Application No. PCT/US2014/026606, Dated Dec. 8, 2014, 8 pages.
International Search Report for Application No. PCT/US2014/026636, Dated Jul. 29, 2014, 5 pages.
International Search Report for Application No. PCT/US2015/038819 Dated Sep. 2, 2015, 12 pages.
International Search Report from PCT/US2014/024256 dated Jul. 30, 2014, pp. 1-15.
International Search Report with Written Opinion corresponding to International Patent Application No. PCT/US2014/059127, mailed May 7, 2015, 21 pages.
Invitation to Pay Additional Fees for International Application No. PCT/US2013/031380, Dated Nov. 28, 2013, 5 pages.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Invitation to Pay Additional Fees for International Application No. PCT/US2014/058991, mailed Jan. 15, 2015, 6 pages.
Invitation to Pay Additional Fees for International Application No. PCT/US2014/059127, dated Jan. 15, 2015, 6 pages.
Invitation to Pay Additional Fees for International Application No. PCT/US2014/065793, dated May 4, 2015, 15 pages.
Jack, M.; Wright, D.; The Role of Advanced Glycation Endproducts and Glyoxalase I in Diabetic Peripheral Sensory Neuropathy; Transl. Res. 2012, 159, 355-365.
Jakobovits, A., "Production of fully human antibodies by transgenic mice" (1995) Curr. Op. Biotechnol., 6:561-566.
Jakubowski, H., Protein N-homocysteinylation: implications for atherosclerosis. Biomedicine; Pharmacotherapy, 2001. 55(8): p. 443-447.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Jefferis, R., Glycosylation of Recombinant Antibody Therapeutics. Biotechnology Progress, 2005.21(1): p. 11-16.
Jespers, "Guiding the Selection of Human Antibodies from Phage Display Repertoires to a Single Epitope of an Antigen" (1994) Bio/Technology, 12:899-903.
Johnson et al., "Characterization of cathepsin L secreted by Sf21 insect cells", Archives of Biochemistry and Biophysics (2005), 444:7-14.
Johnson, K.A., et al., Cation exchange HPLC and mass spectrometry reveal C-terminal amidation of an IqG1 heavy chain. Analytical Biochemistry, 2007. 360(1): p. 75-83.
Kalyanpur, M., "Downstream Processing in the Biotechnology Industry" Molecular Biotechnology, vol. 22:87-98 (2002).
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Karampetsou et al., "TNF-α antagonists beyond approved indications: stories of success and prospects for the future", Q J Med (2010) 103:917-928.

Kaschak et al: "Characterization of the basic charge variants of a human IgGI: Effect of copper concentration in cell culture media", MABS, vol. 3, No. 6, Nov. 1, 2011, pp. 577-583.
Kaufman et al., "Amplification and expression of sequences cotransfected with a modular dihydrofolate reductase complementary dna gene" (1982) Mol. Biol., 159(4):601-621.
Kazuaki F et al "Enhancment of productivity of recombinant a-amidating enzyme by low temperature culture" Cytotechnology 31:85-94, 1999.
Kempeni, "Update on D2E7: a fully human anti-tumour necrosis factor—alpha monoclonal antibody" (2000) Ann. Rheum. Dis., 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." Transfusion 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Kim, Sung Hyun et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009 (Mar. 6, 2009), pp. 639-648.
Kingkeohoi, S., Analysis of methylglyoxal metabolism in CHO celis grown in culture, Cytotechnology (2005) 48:1-13.
Kipriyanov et al. "Recombinant single-chain Fv fragments carrying C-terminal cysteine residues: production of bivalent and biotinylated miniantibodies," Molecular Immunology, (1994) 31(14):1047-1058 F.
Kipriyanov et al., "Single-chain antibody streptavidin fusions: tetrameric bifunctional scFv-complexes with biotin binding activity and enhanced affinity to antigen," Human Antibodies and Hybridomas. (1995) 6(3):93-101.
Knight et al., "Construction and initial characterization of a mouse-human chimeric anti-TNF antibody" (1993) Mol. Immunol., 30(16):1443-1453.
Koide et al., "Monobodies: antibody mimics based on the scaffold of the fibronectin type III domain" (2007), Methods Mol. Biol., 352: 95-109.
Konig et al., "Tumor necrosis factor α and interleukin-1 stimulate bone resorption in vivo as measured by urinary [3H] tetracycline excretion from prelabeled mice" (1988) J. Bone Miner. Res., 3(6):621-627.
Kopaciewicz et al., "Retention Model for High-Performance Ion-Exchange Chromatography,"; Journal of Chromatography, 266:3-21 (1983).
Krehenbrink et al., "Artificial Binding Proteins (Affitins) as Probes for Conformational Changes in Secretin PuID" (2008) J. Mol. Biol., 383 (5): 1058-68.
Kunkel et al., "Comparisons of the Glycosylation of a Monoclonal Antibody Produced under Nominally Identical Cell Culture Conditions in Two Different Bioreactors" (2000) Biotechnol. Prog., 16(3): 462-470.
Kunkel, Jeremy P., et al., "Dissolved oxygen concentration in serum-free continuous culture affects N-linked glycosylation of a monoclonal antibody," Journal of Biotechnology, 62 (1998), 55-71.
Kwon et al., "Production of lactic acid by Lactobacillus rhamnosus with vitamin-supplemented soybean hydrolysate", Enzyme Microb Technol. (2000), 26:209-215.
Leavitt et al. "Impaired Intracellular Migration and Altered Solubility of Nonglycosylated Glycoproteins of Vesicular Stomatitis Virus and Sindbis Virus," J. Biol. Chem. (1977) 252(24):9018-9023.
Lerner et al., "Tumor necrosis factors α and β can stimulate bone resorption in cultured mouse calvariae by a Prostaglandin-independent mechanism" (1993) J. Bone Miner. Res., 8(2):147-155.
Lerner, "Antibodies without immunization" (1992) Science, 258:1313-1314.

(56) References Cited

OTHER PUBLICATIONS

Leusch, "Failure to demonstrate TNFα-specific autoantibodies in human sera by ELISA and Western blot" (1991) *J. Immunol. Methods*, 139:145-47.

Lewis, "Use of alanine scanning mutagenesis to improve the affinity of an anti gp120 (HIV) antibody" (1994) *J. Cell. Biochem.*, 18D:215.

Li, F. et al., "Current Therapeutic Antibody Production and Process Optimization" BioProcessing Journal, vol. 4(5), 2005, pp. 1-8.

Li, Feng, et al., "Cell Culture Processes for Monoclonal Antibody Production," mAbs 2:5, 466-479 (Sep.-Oct. 2010).

Lifely et al., "Glycosylation and Biological Activity of CAMPATH-1H Expressed in Different Cell Lines and Grown Under Different Culture Conditions", *Glycobiology*, 5(8):813-822 (1995).

Liu et al. "Recovery and purificaiton process development for monoclonal antibody production" MABS, 2(5), pp. 480-499 (2010).

Liu et al., "The significance of changes in serum tumour necrosis factor (TNF) activity in severely burned patients" (1994) Burns, 20(1):40-44.

Liu, H., Assessment of antibody fragmentation by reversed-phase liquid chromatography and mass spectrometry. J Chromatogr B Analyt Technol Biomed Life Sci, 2008. 876(1): p. 13-23.

Liu, H., et al., Heterogeneity of monoclonal antibodies. Journal of Pharmaceutical Sciences, 2008. 97(7): p. 2426-2447.

Liu, M, et al.; Discovery of Undefined Protein Cross-Linking Chemistry: A Comprehensive Methodology Utilizing 18O-Labeling and Mass Spectrometry; Anal. Chem. 2013, 5900-5908.

Liu, M.et al.; Protein Isoaspartate Methyltransferase-Mediated 18O-Labeling of Isoaspartic Acid for Mass Spectrometry Analysis; Anal. Chem. 2011, 84, 1056-1062.

Lo, T.W. et al., Binding and modification of proteins by methylglyoxal under physiological conditions. A kinetic and mechanistic study with N alpha-acetylarginine, N alpha-acetyilysine, and N alpha-acetyllysine, and bovine serum albumin, Dec. 23, 1994, The Journal of Biological Chemistrv, 269, 32299-32305.

Logan, John S. "Transgenic Animals: Beyond 'Funny Milk'", *Current Opinion in Biotechnology*, 4:591-595 (1993).

Lonberg et al., "Antigen-specific human antibodies from mice comprising four distinct genetic modifications" (1994) *Nature*, 368:856-859.

Lonberg et al., "Human Antibodies from Transgenic Mice" (1995) *Int. Rev. Immunol.*, 13:65-93.

Low et al., "Mimicking Somatic Hypermutation: Affinity Maturation of Antibodies Displayed on Bacteriophage Using a Bacterial Mutator Strain" (1996) *J. Mol. Biol.*, 260:359-368.

Low, Nigel: thesis extract (1996) *Cambridge University*, 2 pages.

Lowe et al. "A Genetic Approach to Mammalian Glycan Function," Annu. Rev. Biochem. (2003) 72:643-691.

Lu C. et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.

Luo et al., "Understanding of C-terminal lysine variants in antibody production using mammalian cells" Abstract of papers, ACS, Anaheim, CA, US, Mar. 2011, 1 page.

Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.

Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012 (Jul. 2012), pp. 1061-1068.

Ma, et al., "Generation and Assembly of Secretory Antibodies in Plants", *Science*, 268:716-719 (1995).

MacDonald et al., "Tumour necrosis factor-alpha and interferon-gamma production measured at the single cell level in normal and inflamed human intestine" (1990) Clin. Exp. Immunol, 81(2):301-305.

Maeda, et al., "Analysis of Nonhuman N-Glycans as the Minor Constituents in Recombinant Monoclonal Antibody Pharmaceuticals", *Anal. Chem.*, 84:2373-2379 (2012).

Mahler, et al. Induction and analysis of aggregates in a liquid IgG1-antibody formulation. Eur J Pharm Biopharm. 2005, 59(3):407-17; p. 408; col. 1-2; p. 409.

Manning, M., et al., *Stability of Protein Pharmaceuticals: An Update*. Pharmaceutical Research, 2010.27(4): p. 544-575.

Marks et al., "Human antibody fragments specific for human blood group antigens from a phage display library" (1993) Bio/Technology, 11:1145-1149.

Marks et al., "Molecular evolution of proteins on filamentous phage. Mimicking the strategy of the immune system" (1992) *J. Biol. Chem.* 267:16007-16010.

Marks, "By-passing immunization: Human antibodies from V-gene libraries displayed on phage" (1991) *J. Mol. Biol.*, 222:581-597.

Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.

Marks, JD., "By-Passing Immunization: Building High Affinity Human Antibodies by Chain Shuffling" (1992) *Biotechnology*, 10:779-783.

Martin, A.C.R. "Accessing the Kabat antibody sequence database by computer" (1996)*Proteins: Structure, Function and Genetics*, 25:130-133.

Martinelle, K. et al., "Effect of different cell culture medium surfactants on cell growth and viability", Cells and Culture, Proceedings of the 20th ESACT Meeting v4 819-822, Jun. 17-20, 2007.

Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.

McAtee et al., "Isolation of monoclonal antibody charge variants by displacement chromatography," Current Protocols in Protein Science, 8.10.8-8.10.13,2012.

McCauley et al., "Altered cytokine production in black patients with keloids" (1992) J. Clin. Immunol., 12(4):300-308.

McClain et al., "Increased tumor necrosis factor production by monocytes in alcoholic hepatitis" (1989) Hepatology, 9(3):349-351.

Medynski, "Phage Display: All Dressed Up and Ready to Role" (1994) *Bio/Technology*, 12:1134-1136.

Mehta, et al. "Purifying therapeutic monoclonal antibodies," Chemical Engineering Progress; May 2008, 104, 5; pp. S14-20.

Mendez et al., "Functional transplant of megabase human immunoglobulin loci recapitulates human antibody response in mice" (1997) *Nature Genetics*, 15:146-156.

Meuwly, F. et al., "Conversion of a CHO cell culture process from perfusion to fed-batch technology without altering product quality", J.Biotechn. 123:106-116, 2006.

Miller et al., "Characterization of site-specific glycation during process development of a human therapeutic monoclonal antibody" Journal of Pharmaceutical Sciences, vol. 100, No. 7, Jul. 2011, 2543-2550.

Millipore, "Pellicon 2 Filters and Holders," 2003, pp. 1-8.

Millward et al. "Effect of constant and variable domain glycosylation on pharmacokinetics of therapeutic antibodies in mice," Biologicals.(2008) 36(1):41-47.

Mizuochi, T., et al., Structural and numerical variations of the carbohydrate moiety of immunoglobulin G. J Immunol, 1982. 129(5): p. 2016-20.

Moller et al., "Monoclonal antibodies to human tumor necrosis factor α: In vitro and in vivo application" (1990) Cytokine 2(3):162-169.

Moore, A., et al., "Effects of temperature shift on cell cycle, apoptosis and nucleotide pools in CHO cell batch cultures", Cytotechnology, 23:47-54, 1997.

Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.

Morgan et al. "Designing Biobetter Monoclonal Antibody Therapeutics by Glycoengineering," International Pharmaceutical Industry. (2011) pp. 38-44.

(56) References Cited

OTHER PUBLICATIONS

Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.

Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.

Möller, Monoclonal antibodies to human tumor necrosis factor α: in vitro and vivo application (1990) *Cytokine*, 2(3):162-69.

Neuberger M. et al., "Mice perform a human repertoire" (1997) *Nature*, 386:25-26.

Ngo et al., "Kosmotropes enhance the yield of antibody purified by affinity chromatography using immobilized bacterial immunoglobulin binding proteins," Journal of Immunoassay & Immunochemistry, (2008) 29(1):105-115.

Ni, W.; Analysis of Isoaspartic Acid by Selective Proteolysis with Asp-N and Electron Transfer Dissociation Mass Spectrometry; Anal. Chem. 2010, 82,7485-7491.

Nilsson, "Antibody engineering" (1995) *Current Opinion in Structural Biology*, 5:450-456.

Nixon et al., "Engineered protein inhibitors of proteases" (2006) Curr Opin Drug Discov Devel, 9(2): 261-8.

Nogal, B., Chhiba, K. And Emery, J. C. (2012), Select host cell proteins coelute with monoclonal antibodies in protein a chromatography. Biotechnol Progress, 28: 454-458.

Noguchi et al., "Failure of Human Immunoresponse to N-Glycolylneuraminic Acid Epitope Contained in Recombinant Human Erythropoietin", *Nephron*, 72:599-603 (1996).

Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).

Nygren et al., "Alternative binding proteins: affibody binding proteins developed from a small three-helix bundle scaffold" (2008) FEBS J., 275 (11): 2668-76.

Oh, D-K. et al., "Increased erythritol production in fed-batch cultures of *Torula* sp. By controlling glucose concentration", J. Industrial Microb. & Biotechn. 26(4): 248-252, 2001.

Oh, et al., "Effect of N-Acetylcystein on Butyrate-Treated Chinese Hamster Ovary Cells to Improve the Production of Recombinant Human Interferon-β-1a", Biotechnol. Prog. 21 (4):1154-1164, 2005.

Oh, SKW, et al., "Substantial Overproduction of Antibodies by Applying Osmotic Pressure and Sodium Butyrate", Biotechn. Bioengin. 42(5):601-610, 1993.

Osbourn, "From rodent reagents to human therapeutics using antibody guided selection" (2005) *Methods*, 36(1):61-68.

Ouellette, D.; Studies in serum support rapid formation of disulfide bond between unpaired cysteine residues in the VH domain of an immunoglobulin G1 molecule; Anal. Biochem. 2010, 397, 37.

Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-18502.

Pacis, et al.: "Effects of cell culture conditions on antibody N-linked glycosylation—what affect high mannose 5 glycoform", Biotechnology and Bioengineering vol. 108, No. 10 Oct. 2011, pp. 2348-2358.

Packer et al., "A general approach to desalting oligosaccharides released from glycoproteins" (1998) Glycoconj J., 15(8):737-47.

Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.

Parekh RB N-glycosylation and the production of recombinant glycoproteins vol. 7, Issue 5, p. 117-122, May 1989 Trends in Biotechnology.

Parekh, R.B., et al., Association of rheumatoid arthritis and primary osteoarthritis with changes in the glycosylation pattern of total serum IgG. Nature, 1985. 316(6027): p. 452-7.

Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.

PCT/US2013/069702 International Search Report & Written Opinion mailed Jan. 31, 2014, 13 pages.

Perchiacca, J.M., et al., "Engineering Aggregation-Resistant Antibodies," Annual Review of Chemical and Biomolecular Engineering 3:263-286 (2012).

Perkins, M.; et. al. Determination of the Origin of Charge Heterogeneity in a Murine Monoclonal Antibody; M. Pharm. Res. 2000, 17, 1110-1117.

Pietersz et al., "In vitro and in vivo Antitumor Activity of a Chimeric anti-CD19 Antibody", *Cancer Immunol. Immunother.*, 41:53-60 (1995).

Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.

Potter et al., "Antibody Production in the Baculovirus Expression System", *Intern. Rev. Immunol.*, 10:103-112 (1993).

Poul et al., "Design of Cassette Baculovirus Vectors for the Production of Therapeutic Antibodies in Insect Cells", *Immunotechnology*, 1:189-196 (1995).

Proteus, "Protein A Antibody Purification Handbook," Pro-Chem Inc., 2005, pp. 1-52.

Quan, C., et al., A study in glycation of a therapeutic recombinant humanized monoclonal antibody: Where it is, how it got there, and how it affects charge-based behavior. Analytical Biochemistry, 2008.373(2): p. 179-191.

Queen, C., "A humanized antibody that binds to the interleukin 2 receptor" (1989) *Proc. Natl. Acad. Sci. USA*, 86(24):10029-10033.

Rabbani, N.; Thornalley, P. J.; Glyoxalase in diabetes, obesity and related disorders; Semin. Cell Dev. Biol. 2011, 22, 309-317.

Rader et al. "A phage display approach to rapid antibody humanization: Designed combinatorial V gene libraries" (1998) *Proc Natl Acad Sci USA*, 95:8910-8915.

Raju et al. "Galactosylation variations in marketed therapeutic antibodies," MABS. (May 1, 2012) 4(3):385-391.

Raju et al., "Glycoengineering of Therapeutic Glycoproteins: In Vitro Galactosylation and Sialylation of Glycoproteins with Terminal N-Acetylglucosamine and Galactose Residues" (2001) Biochemistry, 40(30):8868-8876.

Raju, TS. "Glycosylation Variations with Expression Systems and Their Impact on Biological Activity of Therapeutic Immunoglobulins", *BioProcess International.*, 44-53 (2003).

Rankin et al., "The therapeutic effects of an engineered human anti-tumour necrosis factor alpha antibody(CDP571) in rheumatoid arthritis" (1995) Br. J. Rheumatol., 34:334-342.

Rau "Adalimumab (a fully human anti-tumour necrosis factor alpha monoclonal antibody) in the treatment of active rheumatoid arthritis: the initial results of five trials" Ann Rheum Dis 2002,61 (Suppl II): ii70-ii73.

Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011 (Jan. 25, 2011), pp. 317-323.

Reichert JM., "Monoclonal antibody successes in the clinic", Nature Biotech. 23(9):1073-1078, 2005.

Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.

Remy et al., "Zinc-finger nucleases: A powerful tool for genetic engineering of animals" (2010) Transgenic Res., 19(3): 363-71.

(56) References Cited

OTHER PUBLICATIONS

Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Restelli, Veronica, et al., "The Effect of Dissolved Oxygen on the Production and the Glycosylation Profile of Recombinant Human Erythropoietin Produced From CHO Cells," Biotechnology and Bioengineering, vol. 94, No. 3, (2006) 481-494.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast *Pichia pastoris*", *Biotechnology*, 13:255-260 (1995).
Riechmann, "Phage display and selection of a site-directed randomized single-chain antibody Fv fragment for its affinity improvement" (1993) *Biochemistry*, 32(34):8848-8855.
Roe, S. "Separation Based on Structure" Chapter 4, § 5.2, In, Protein Purification Methods; A Practical Approach, Harries, et al. Sep. 1989, p. 203.
Rouiller et al. "Effiect of hydrocortisone on the production and glycosylation of an Fc-Fusion protein in CHO cell cultures," Biotechnology Progress.(May 2012) 28(3):803-813.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997 (Jan. 1, 1997), pp. 201-207.
Roy, B.M., et al., Toxic concentrations of exogenously supplied methy!glyoxal in hybridoma cell culture, Cytotechnology (2004) 46:97-107.
Roy, Samar N. et al., "Secretion of Biologically Active Recombinant Fibrinogen by Yeast." *The Journal of Biological Chemistry*, vol. 270; 40 (1995). 23761-23767.
Rube et al., "Ewing's sarcoma and peripheral primitive neuroectodermal tumor cells produce large quantities of bioactive tumor necrosis factor-$\alpha$ (TNF-$\alpha$) after radiation exposure", Int. J. Radiation Oncology Biol. Phys., (2003), vol. 56, No. 5, pp. 1414-1425.
Rudd et al. "Glycosylation and the Immune System," Science. (2001) 291(5512):2370-2376.
Rudikoff et al., "Single amino acid substitution altering antigen-binding specificity" (1982) *Proc. NatL Acad. Sci. USA*, 70:1979-1983.
Russell et al., "Targets for sepsis therapies: Tumor necrosis factor versus interleukin-1" (1993) Curr. Opin. Biotech., 4:714-721.
Sakai et al; "Use of nonionic surfactants for effective supply of phosphatidic acid in serum-free culture of Chinese hamster ovary cells"; Journal of Bioscience and Bioengineering; 92(3):256-261 (2001).
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.
Santiago et al., "Targeted gene knockout in mammalian cells by using engineered zinc-finger nucleases" (2008) Proc. Natl. Acad. Sci. USA., 105(15):5809-14.
Santora et al., "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.

Sargent, Retrieved from the Internet Archive on Aug. 28, 2013, cellculturedish.com/2012/01/cho-cells-the-top-expressionsystem-of-best-selling-biologic-drugs. 2 pages.
Sato et al, "Stimulation of monoclonal antibody production by human-human hybridoma cells with an elevated concentration of potassium or sodium phosphate in serum-free medium," Cytotechnology 2:63-67, 1989.
Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006 (Nov. 1, 2006), pp. 1161-1173.
Saxena, R. K. et al.; Microbial production and applications of 1,2-propanediol; Indian J. Microbiol. 2010,50,2-11.
Scales et al., "Hepatic ischemia/reperfusion injury: importance of oxidant/tumor necrosis factor interactions" (1994) Am. J. Physiol., 267 (6 Pt 1):G1122-1127.
Schiestl et al. "Acceptable changes in quality attributes of glycosylated biopharmaceuticals" Nature Biotechnology, 29(4), 310-312 (2011).
Schwieterman, "Immunosuppression in Combination with Monoclonal Antibodies" in Biologic Agents in Autoimmune Disease (Mar. 2-4, 1995), pp. 291-298.
Scientific Discussion. Retrieved from the Internet: ema.europa.eu/dics/en_GB/document_library/EPAR_Sceintific_Discussion/human/00481/WC500050867.pdf, EMEA, 2004. Last accessed on Jun. 29, 2015, 25 pages.
Senczuk et al. "Hydrophobic interaction chromatography in dual salt system increases protein binding capacity" Biotechnology and Bioengineering, 103(5), 930-935 (2009).
Seo, Jin Seok, et al., "Effect of culture pH on recombinant antibody production by a new human cell line, F2N78, grown in suspension at 33.0° C. and 37.0° C.," *Appl. Microbiol Biotechnol.*, vol. 97 (2013). 5283-5291.
Seresht et al., "The impact of phosphate scarcity on pharmaceutical protein production in *S. cerevisiae*: linking transcriptomic insights to phenotypic responses" Microbial Cell Factories. 2011, 10: pp. 1-13.
Serrick et al., "The early release of interleukin-2, tumor necrosis factor-alpha and interferon-gamma after ischemia reperfusion injury in the lung allograft" (1994) Transplantation, 58(11):1158-1162.
Shankar et al., "Evaluation of the role of second messenger systems in tumor necrosis factor-stimulated resorption of fetal rat limb bones" (1993) Bone, 14(6):871-876.
Sheeley et al., "Characterization of Monoclonal Antibody Glycosylation: Comparison of Expression Systems and Identification of Terminal $\alpha$-Linked Galactose", *Anal. Biochem.*, 247(1):102-110 (1997).
Sheikh et al., "Studies of the digestion of bradykinin, lysyl bradykinin, and kinin-degradation products by carboxypeptidases A, B, and N;". Biochemical Pharmacology. 1986, 35: 1957-1963.
Shen, Amy Y. et al., "Recombinant DNA Technology and Cell Line Development," from "Cell Culture Technology for Pharmaceutical and Cell-Based Therapies, " CRC Press, 1995, 15-40.
Sheron et al., "Increased production of tumour necrosis factor alpha in chronic hepatitis B virus infection" (1991) J. Hepatol., 12(2):241-245.
Shibuya et al., "The elderberry (*Sambucus nigra* L.) bark lectin recognizes the Neu5Ac(alpha 2-6)Gal/GalNAc sequence" (1987) J. Biol. Chem., 262(4): 1596-1601.
Shields et al. "Lack of Fucose on Human IgGI N-Linked Oligosaccharide Improves Binding to Human FcyRIII and Antibody-dependent Cellular Toxicity," J. Biol. Chem. (2002) 277(30):26733-26740.
Shih, "Effects of Anions on the Deamidation of Soy Protein". Journal of Food Science. 1991, 56: 452-454.
Shim, H., "One target, different effects: a comparison of distinct therapeutic antibodies against the same targets." Experimental and Molecular Medicine, vol. 43, p. 539-549, Oct. 2011.
Shirato, Ken et al., "Hypoxic regulation of glycosylation via the N-acetylglucosamine cycle." *J. Clin. Biochem. Nutr.* vol. 48; 1 (2011). 20-25.

(56) References Cited

OTHER PUBLICATIONS

Shubert et al. "Comparison of ceramic hydroxy- and fluoroapatite versus Protein A/G-based resins in the isiolation of a recombinant human antibody from cell culture supernatant" J. Chromatography A, 114 (2007) 106-113.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sigma Catalog "RPMI1640" (last accessed Jan. 22, 2015), 3 pages.

Sigma MSDS for RMPI1640 (last accessed Jan. 22, 2015), 6 pages.

Silverman et al., "Multivalent avimer proteins evolved by exon shuffling of a family of human receptor domains" (2005) Nat. Biotechnol., 23 (12): 1556-61.

Sioud et al., "Characterization of naturally occurring autoantibodies against tumour necrosis factor-alpha (TNF-α): in vitro function and precise epitope mapping by phage epitope library" (1994) Clin. Exp. Immunol., 98:520-525.

Skerra et al., "Alternative binding proteins: Anticalins—harnessing the structural plasticity of the lipocalin ligand pocket to engineer novel binding activities kerra" (2008) FEBS J., 275 (11): 2677-83.

Stumpp et al., "DARPins: A new generation of protein therapeutics" (2008) Drug Discov. Today, 13 (15-16): 695-701.

Sun et al., "Bowel necrosis induced by tumor necrosis factor in rats is mediated by platelet-activating factor" (1988) J. Clin. Invest., 81(5):1328-1331.

Sundaram et al., "An innovative approach for the characterization of the isoforms of a monoclonal antibody product," Mabs, 3(6):505-512, 2011.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Suthanthiran et al., "Renal transplantation" (1994) New Engl. J. Med., 331(6):365-376.

Takagi, M. et al., "The effect of osmolarity on metabolism and morphology in adhesion and suspension chinese hamster ovary cells producing tissue plasminogen activator", Cytochnology 32:171-179, 2000.

Takashima et al., "Characterization of Mouse Sialyltransferase Genes: Their Evolution and Diversity" (2008) Biosci. Biotechnol. Biochem., 72(5):1155-1167.

Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.

Tan et al., "Expression and purification of a secreted functional mouse/human chimaeric antibody against bacterial endotoxin in baculovirus-infected insect cells", Biotechnol. Appl. Biochem. (1999), 30:59-64.

Taylor et al. "A transgenic mouse that expresses a diversity of human sequence heavy and light chain immunoglobulins," Nucleic Acids Research,(1992) 20(23):6287-6295.

Taylor et al.,"Human immunoglobulin transgenes undergo rearrangement, somatic mutation and class switching in mice that lack endogenous IgM" (1994) *Int. Immunol.*, 6:579-591.

Tebbey, Paul W., et al., "Consistency of quality for the glycosylated monoclonal antibody Humira (adalimumab)," MAbs, Sep. 3, 2015;7(5); 805-11.

Teichmann, S. Declaration dated Dec. 17, 2010 from opposition proceedings in EP 0929578, 6 pages.

TESS database "HYCLONE" Trademark #76244963. Filing date Apr. 23, 2001. Live mark. Last accessed Jan. 21, 2015.

TESS database "HYCLONE" Trademark #85769283. Filing date Nov. 1, 2012. Live mark. Last accessed Jan. 21, 2015.

Tharmalingam et al.; "Pluronic Enhances the Robustness and Reduces the Cell Attachment of Mammalian Cells"; Molecular Biotechnology; 39(2):167-177 (2008).

The Difference-Between, "Poly vs. Polyalcohol—What's the difference?" pp. 1-2, downloaded from http://the-difference-between.com/polyalcohol/polyol on Apr. 16, 2016.

The Kennedy Institute of Rheumatology, 1995 Annual Scientific Report, "Anti-TNF trials and studies of mechanisms of action," 4 pages.

The MW Calculator available at the Sequence Manipulation Suite. Retrieved from the internet: bioinformatics.org/sms2/index.html), . Last accessed on Feb. 25, 2014, 2 pages.

The pI Calculator available at the Sequence Manipulation Suite. Retrieved from the internet: bioinformatics.org/sms2/index.html, Last accessed on Feb. 25, 2014, p. 1.

The Statement on a Nonproprietary Name Adopted by the USAN Council for Adalimumab. Retrieved from the internet:ama-assn.org/resources/doc/usan/adalimumab.doc. Last accessed on May 19, 2011, 1 page.

Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.

Tomiya et al., "Comparing N-glycan processing in mammalian cell lines to native and engineered; lepidopteran insect cell lines," Glycoconjuqate Journal 21 :343-360 (2004).

Tomlinson, "The repertoire of human germline VH sequences reveals about fifty groups of VH segments with different hypervariable loops" (1992) *J. Mol. Biol.*, 227:776-98.

Tomlinson, "The structural repertoire of the human Vk domain" (1995) *The EMBO J.*, 14(18):4628-38.

Tracey et al., "Shock and tissue injury induced by recombinant human cachectin" (1986) Science, 234(4775):470-474.

Tracey, "Tumor necrosis factor: A pleiotropic cytokine and therapeutic target" (1994) *Annu. Rev. Med.*, 45:491-503.

Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.

United States Food and Drug Administration (FDA) Biological Licensing Application File No. 125057 (Adalimumab) (Dec. 31, 2002). Retrieved from the internet: fda.gov/Drugs/DevelopmentApprovalProcess/HowDrugsareDevelopedandApproved/ApprovalApplications/TherapeuticBiologicApplications/ucm080610.htm. Last Accessed on Mar. 4, 2015, 1 page.

Urlaub et al., "Isolation of Chinese hamster cell mutants deficient in dihydrofolate reductase activity" (1980) Proc. Natl. Acad. Sci. USA, 77:4216-4220.

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).

Van Der Poll et al., "Activation of coagulation after administration of tumor necrosis factor to normal subjects" (1990) N. Engl. J. Med., 322(23):1622-1627.

Van Der Poll et al., "Comparison of the early dynamics of coagulation activation after injection of endotoxin and tumor necrosis factor in healthy humans" (1991) Prog. Clin. Biol. Res., 367:55-60.

Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.

Van Dulleman et al., "Treatment of Crohn's disease with anti-tumor necrosis factor chimeric monoclonal antibody (cA2)" (1995) Gastroenterology, 109(1):129-135.

Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.

(56) References Cited

OTHER PUBLICATIONS

Van Lent PL, et al. "The impact of protein size and charge on its retention in articular cartilage" J Rheumatol. Aug. 1987;14(4):798-805.
Varasteh et al. Optimization of Anti-Rh D Immunoglobulin Stability in the Lyphiliization Process. Iranian Journal of Basic Medical Sciences, Spring 2008, vol. 11, No. 1. pp. 55-61.
Varki et al. Essentials of Glycobiology, 2nd edition, (1999) CSHL, Retrieved from the internet: ncbi.nlm.nih.gov/books/NBK1908/, 4 pages.
Vasilli, P. et al., The Pathophysiology of Tumor Necrosis Factors, Annu. Rev. Immunol. 10:411-452 (1992).
Vaughan, "Human antibodies by design" (1998) Nature Biotechnology, 16:535-539.
Vlasak, J. & Ionescu, R., *Heterogeneity of Monoclonal Antibodies Revealed by Charge-Sensitive Methods*. Current Pharmaceutical Biotechnology, 2008. 9(6): p. 468-481.
Wagner et al., "Antibodies generated from human immunoglobulin miniloci in transgenic mice" (1994) Nucl. Acids Res. 22:1389-1393.
Wagner et al., "The diversity of antigen-specific monoclonal antibodies from transgenic mice bearing human immunoglobulin gene miniloci" (1994) Eur. J. Immunol., 24:2672-2681.
Wallick et al. "Glycosylation of a VH residue of a monoclonal antibody against alpha (1-6) dextran increases its affinity for antigen," J. Exp. Med.(1988) 168(3):1099-1109.
Walsh et al. "Effect of the carbohydrate moiety on the secondary structure of ?2-glycoprotein. I. Implications for the biosynthesis and folding of glycoproteins," Biochemistry. (1990) 29(26):6250-6257.
Walsh, et al.: "Post-translational modifications in the context of therapeutic proteins", Wiley-VCH Verlag GmbH (2009), pp. 1-14.
Wang et al., "The immobilized leukoagglutinin from the seeds of Maackia amurensis binds with high affinity to complex-type Asn-linked oligosaccharides containing terminal sialic acid-linked alpha-2,3 to penultimate galactose residues" (1988) J Biol. Chem., 263(10): 4576-4585.
Wang, Tina et al., "Exploring Post-translational Arginine Modification Using Chemically Synthesized Methylglyoxal Hydroimidazolones," *J. Am. Chem. Soc.*, 2012, 134, pp. 8958-8967.
Wang, Z.; et al. Desulfurization of Cysteine-Containing Peptides Resulting from Sample Preparation for Protein Characterization by MS; Rapid Commun. Mass Spectrom. 2010, 24, 267-275.
Ward, "Binding activities of a repertoire of single immunoglobulin variable domains secreted from *Escherichia coli*" (1989) Nature, 341:544-546.
Warnock et al., "In vitro galactosylation of human IgG at 1 kg scale using recombinant galactosyltransferase" (2005) Biotechnol. Bioeng., 92(7):831-842.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Wedemayer et al., "Structural insights into the evolution of an antibody combining site" (1997) Science, 276:1665-1669.
Weikert et al., "Engineering Chinese hamster ovary cells to maximize sialic acid content of recombinant glycoproteins" (1999) Nature Biotechnology, 17(11): 1116-1121.
Weinstein et al., "Primary structure of beta-galactoside alpha 2,6-sialyltransferase. Conversion of membrane-bound enzyme to soluble forms by cleavage of the NH2-terminal signal anchor" (1987) J. Biol. Chem. 262(36):17735-17743.
Wiendl et al., "Therapeutic Approaches in Multiple Sclerosis. Lessons from failed and interrupted treatment trials", BioDrugs. (2002), 16(3):183-200.
Williams et al., "Kinetic analysis by stopped-flow radiationless energy transfer studies: effect of anions on the activity of carboxypeptidase A". Biochemistry. 1986, 25, 94-100.
Williams, A. et al., Ion-Exchange Chromatography, Oct. 1998, Supplement 44, pp. 10-10-1-10-10-30.
Winter, "Humanized antibodies" (1993) Immunol. Today, 14(6):243-246.
Winter, "Making antibodies by phage display technology" (1994) *Annu. Rev. Immunol.*, 12:433-455.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2,Oct. 1, 2010, pp. 321-336.
Worthington Biochemical Corporation, porcine pancreas carboxypeptidase B, one page, Feb. 25, 2012.
Wurm, FM, "Production of recombinant protein therapeutics in cultivated mammalian cells", Nature Biotechnology 22(11):1393-1398, 2004.
Wyss, et al. "The structural role of sugars in glycoproteins," Curr. Opin. Biotechnol. (1996), 7(4); 409-416.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yao et al., "The potential etiologic role of tumor necrosis factor in mediating multiple organ dysfunction in rats following intestinal ischemia-reperfusion injury" (1995) Resuscitation, 29(2):157-168.
Yigzaw et al., "Exploitation of the adsorptive properties of depth filters for host cell protein removal during monoclonal antibody purification," Biotechnology Progress, (2006) 22(1):288-296.
Yuk, I.H. et al., Controlling Glycation of Recombinant Antibody in Fed Batch Cell Cultures, Nov. 2011 , Biotechnoloqy and Bioenqineerinq, vol. 108, No. 11 pp. 2600-2610.
Yumioka et al., "Screening of effective column rinse solvent for Protein-A chromatography," Protein Expression and Purification, (2010) 70(2): 218-223.
Zang, T.; et al.; Chemical Methods for the Detection of Protein N-Homocysteinylation via Selective Reactions with Aldehydes; Anal. Chem. 2009, 81, 9065-9071.
Zatarain-Rios E and Mannik M, "Charge-charge interactions between articular cartilage and cationic antibodies, antigens, and immune complexes," Arthritis Rheum. Nov. 1987;30(11):1265-73.
Zhang et al. "A novel function for selenium in biological system: Selenite as a highly effective iron carrier for Chinese hamster overary cell growth and monoclonal antibody production," Biotechnology and Bioengineering. (2006) 95(6):1188-1197.
Zhang et al., "CHO glycosylation mutants as potential host cells to produce therapeutic proteins with enhanced efficacy" (2013) Advances in Biochemical Engineering/Biotechnology, 131:63-87.
Zhang et al., "Isolation and characterization of charge variants using cation exchange displacement chromatography," 1218(31): 5079-5086, 2011.
Zhang, B., et al., Unveiling a Glycation Hot Spot in a Recombinant Humanized Monoclonal Antibody. Analytical Chemistry, 2008. 80(7): p. 2379-2390.
Zhang, F. et al., "The Effect of Dissolved Oxygen (DO) Concentration on the Glycosylation of Recombinant Protein Produced by the Insect Cell-Baculovirus Expression System." *Biotechnology and Bioengineering*, (2002), 77(2); 219-224.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhang, Y. et al., "Specificity and Mechanism of Metal Ion Activation in UDP-galactose: β-Galactoside-α-1,3-galactosyltransferase." *J. Biological Chemistry* vol. 276; 15 (2001). 11567-11574.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
Zou et al., "Dominant expression of a 1.3 Mb human Ig kappa locus replacing mouse light chain production" (1996) *FASEB J.*, 10:1227-1232.

(56) References Cited

OTHER PUBLICATIONS

"Preliminary Data From Two Clinical Trials Demonstrate Abbott Laboratories' HUMIRA Improved Symptoms of Psoriatic Arthritis and Ankylosing Spondylitis" *PR Newswire* (2004).
Abbott Laboratories Announces Positive Results of Phase II HUMIRA (R) (adalimumab) Study in Psoriasis, P.R. Newswire. (2004).
Amersham Biosciences, *Antibody Purification Handbook* (2002).
Andersen et al., *Protein Glycosylation: Analysis, Characterization, and Engineering*, Encyclopedia of Industrial Biotechnology (2011).
Arakawa et al., *Biotechnology applications of amino acids in protein purification and formulations*, Amino Acids, vol. 33, pp. 587-605 (2007).
Avgerinos, *HUMIRA manufacturing: challenges and the path taken*, Extended Reports from the 3rd International Symposium on Downstream Processing of Genetically Engineered Antibodies and Related Molecules (Oct. 3-5, 2004).
Babcock et al., *Partial Replacement of Chemically Defined CHO Media with Plant-Derived Protein Hydrolysates*, in Proceedings of the 21st Annual Meeting of the European Society for Animal Cell Technology (ESACT), Dublin, Ireland, Jun. 7-10, 2009, pp. 295-298 (Springer Netherlands).
Baynes et al., *Role of Arginine in the Stabilization of Proteins against Aggregation*, Biochemistry, vol. 44, pp. 4919-4925 (2005).
Bibila & Robinson, *In Pursuit of the Optimal Fed-Batch Process for Monoclonal Antibody Production*, Biotechnol. Prog., 11:1-13 (1995).
Borys et al., *Ammonia Affects the Glycosylation Patterns of Recombinant Mouse Placental Lactogen-I by Chinese Hamster Ovary Cells in a pH-Dependent Manner*, Biotechnology and Bioengineering, 43:505-514 (1994).
Braun (2002), Anti-tumor necrosis factor a therapy for ankylosing spondylitis: international experience, Ann. Rheum. Dis. 61(Suppl. III):iii51-iii60.
Butler, *Animal cell cultures: recent achievements and perspectives in the production of biopharmaceuticals*, Appl. Microbiol. Biotechnol., 68: 283-291 (2005).
Butler, *Optimisation of the Cellular Metabolism of Glycosylation for Recombinant Proteins Produced by Mammalian Cell Systems*, Cytotechnology, 50:57-76 (2006).
Carpenter et al., Rational Design of Stable Protein Formulations: Theory and Practice, 101 pages, (2002).
Champion et al., *Defining Your Product Profile and Maintaining Control Over It, Part 2*, BioProcess Technical, vol. 3, pp. 52-57 (Sep. 2005).
Chen et al., *Effects of Elevated Ammonium on Glycosylation Gene Expression in CHO Cells*, Metabolic Engineering, 8:123-132 (2006).
Chun et al., *Usability of size-excluded fractions of soy protein hydrolysates for growth and viability of Chinese hamster ovary cells in protein-free suspension culture*, Bioresource Technology, 98:1000-1005 (2007).
Clinical trial No. NCT00085644 "Human Anti-tumor Necrosis Factor (TNF) Monoclonal Antibody Adalimumab in Subjects With Active Ankylosing Spondylitis (ATLAS)" (2004).
Clinical trial No. NCT00235105 "Adalimumab in Early Axial Spondyloarthritis (Without Radiological Sacroiliitis): Placebo Controlled Phase Over 3 Months Followed by a 9 Months Open Extension Phase" (2005).
Coffman et al., *High-Throughput Screening of Chromatographic Separations: 1. Method Development and Column Modeling*, Biotechnology & Bioengineering, 100:605-618 (2008).
Commercially Available Humira product, approved by the FDA in Dec. 2002 and available in Jan. 2003.
CPMP Policy Statement on DNA and Host Cell Proteins (HCP) Impurities, Routine Testing versus Validation Studies, EMEA, Jun. 10, 1997.

Cromwell, *Avastin: highlights from development*, Extended Reports from the 3rd International Symposium on Downstream Processing of Genetically Engineered Antibodies and Related Molecules (Oct. 3-5, 2004).
Cruz et al., *Process development of a recombinant antibody/interleukin-2 fusion protein expressed in protein-free medium by BHK cells*, Journal of Biotechnology, 96:169-183 (2002).
Cumming, *Glycosylation of recombinant protein therapeutics: control and functional implications*, Glycobiology, 1(2):115-130 (1991).
Davis et al., Recombinant Human Tumor Necrosis Factor Receptor (Etanercept) for Treating Ankylosing Spondylitis, Arthritis & Rheumatism 48:3230-3236 (2003).
Del Val et al., *Towards the Implementation of Quality by Design to the Production of Therapeutic Monoclonal Antibodies with Desired Glycosylation Patterns*, American Institute of Chemical Engineers, Biotechnol. Prog., 26(6):1505-1527 (2010).
EMEA, *Avastin Scientific Discussion* (2005).
Endres, *Soy Protein Products Characteristics, Nutritional Aspects, and Utilization*, 2001 (AOCS Press, Champaign, Illinois).
Ertani et al., *Biostimulant activity of two protein hydrolyzates in the growth and nitrogen metabolism of maize seedlings*, J. Plant Nutr. Soil Sci., 000:1-8 (2009).
Espinosa-Gonzalez, *Hydrothermal treatment of oleaginous yeast for the recovery of free fatty acids for use in advanced biofuel production*, Journal of Biotechnology, 187:10-15 (2014).
Exposure Factors Handbook, U.S. Environmental Protection Agency (1997).
Falconer et al., *Stabilization of a monoclonal antibody during purification and formulation by addition of basic amino acid excipients*, vol. 86, pp. 942-948 (2011).
Farnan et al., Multiproduct High-Resolution Monoclonal Antibody Charge Variant Separations by pH Gradient Ion-Exchange Chromatography, Analytical Chem., vol. 81, No. 21, pp. 8846-8857 (2009).
Fauchère et al., *Amino acid side chain parameters for correlation studies in biology and pharmacology*, Int. J. Peptide Res., vol. 32, pp. 269-278 (1988).
Follmam et al., Factorial screening of antibody purification processes using three chromatography steps without protein A, J. Chromatography A, vol. 1024, pp. 79-85 (2004).
Foong et al., *Anti-tumor necrosis factor-alpha-loaded microspheres as a prospective novel treatment for Crohn's disease fistulae*, Tissue Engineering, Part C: Methods, 16(5):855-64 (2010).
Franek et al., Plant Protein Hydrolysates: Preparation of Defined Peptide Fractions Promoting Growth and Production in Animal Cells Cultures, Biotech. Progress, 16:688-692 (2000).
FrieslandCampina Domo. *Product Data Sheet: Proyield Pea PCE80B*. Paramus, NJ: Aug. 2011.
FrieslandCampina Domo. *Product Data Sheet: Proyield Soy SE70M-UF*. Paramus, NJ: Apr. 2011.
FrieslandCampina Domo. *Product Data Sheet: Proyield Wheat WGE80M-UF*. Paramus, NJ: Apr. 2011.
FrieslandCampina Domo. *Product Information Sheet: CNE50M-UF*. Zwolfe, NL: Jun. 2010.
Gagnon et al., *Technology trends in antibody purification*, J. Chromatography A., vol. 1221, pp. 57-70 (available online Oct. 2011).
Gawlitzek et al., *Ammonium Alters N-Glycan Structures of Recombinant TNFR-IgG: Degradative Versus Biosynthetic Mechanisms*, Biotechnology and Bioengineering, 68(6):637-646 (2000).
Gawlitzek et al., *Identification of Cell Culture Conditions to Control N-Glycosylation Site-Occupancy of Recombinant Glycoproteins Expressed in CHO cells*, 103:1164-1175 (2009).
Gibbs, *Production and Characterization of Bioactive Peptides from Soy Fermented Foods and Their Hydrolysates*, Dissertation, McGill University, Montreal Quebec (1999).
Gong et al., *Fed-Batch Culture Optimization of a Growth-Associated Hybridoma Cell Line in Chemically Defined Protein-Free Media*, Cytotechnology, 52:25-38 (2006).
Goochee et al., *Environmental Effects on Protein Glycosylation*, Biotechnology, 8:421-427 (1990).
Gorfien et al., *Optimized Nutrient Additives for Fed-Batch Cultures*, BioPharm International, 16:34-40 (2003).

(56) References Cited

OTHER PUBLICATIONS

Gu et al., *Influence of Primatone RL Supplementation on Sialylation of Recombinant Human Interferon-γ Produced by Chinese Hamster Ovary Cell Culture Using Serum-Free Media*, Biotechnology and Bioengineering, 56(4):353-360 (1997).
Guidance for Industry—Q6B Specifications: Test Procedures and Acceptance Criteria for Biotechnological / Biological Products, Aug. 1999.
Guse et al., *Purification and analytical characterization of an anti-CD4 monoclonal antibody for human therapy*, J. of Chromatography A, 661:13-23 (1994).
Haibel (2005) *Arthritis and Rheumatism* 64(Suppl. III):316.
Haibel et al. (2004) *Arthritis and Rheumatism* 50(9):S217-18.
Hansen et al., *Extra- and intracellular amino acid concentrations in continuous Chinese hamster ovary cell culture*, Appl. Microbiol. Biotechnol., 41:560-564 (1994).
Harris et al., *Current Trends in Monoclonal Antibody Development and Manufacturing*, Chapter 12, pp. 193-205 (2010).
Hayter et al, *Chinese hamster ovary cell growth and interferon production kinetics in stirred batch culture*, Applied Microbiol. Biotech., 34:559-564 (1991).
Heeneman et al., *The concentrations of glutamine and ammonia in commercially available cell culture media*, J. Immunological Methods, 166:85-91(1993).
Hong et al., *Substitution of glutamine by glutamate enhances production and galactosylation of recombinant IgG in Chinese hamster ovary cells*, Applied Microbiol. Biotech., 88:869-876 (2010).
Huang et al., *Nitrogen metabolism of asparagine and glutamate in Vero cells studied by 1H/15N NMR spectroscopy*, Applied Microbiol. Biotech., 77:427-436 (2007).
International Conference on Harmonisation of Technical Requirements for Registration of Pharmaceuticals for Human Use, *Specifications: Test Procedures and Acceptance Criteria for Biotechnological / Biological Products Q6B*, Mar. 10, 1999.
Jacob et al., Scale-up of Antibody Purification, Antibodies, vol. 1: Production & Purification, (2004).
Karnoup et al., *O-Linked glycosylation in maize-expressed human IgA1*, Glycobiology, 15(10):965-981 (2005).
Kaufman et al., *Depletion of manganese within the secretory pathway inhibits O-linked glycosylation in mammalian cells*, Biochemistry, 33(33):9813-9 (1994).
Kelley et al., *Downstream Processing of Monoclonal Antibodies: Current Practices and Future Opportunities*, Process Scale Purification of Antibodies (2009).
Kim et al., *Glycosylation pattern of humanized IgG-like bispecific antibody produced by recombinant CHO cells*, Applied Microbiol. Biotech., 85:535-542 (2010).
Kobak, Osteonecrosis and monoarticular rheumatoid arthritis treated with intra-articular adalimumab, S. Mod Rheumatol, 18, 290-292, Feb. 20, 2008.
Kramarczyk et al., *High-Throughput Screening of Chromatographic Separations: II. Hydrophobic Interaction*, 100: 708-720 (2008).
Kurano et al., *Growth behavior of Chinese hamster ovary cells in a compact loop bioreactor. 2. Effects of medium components and waste products*, J. Biotechnol., 15(1-2):113-128 (1990).
Lain et al., *Development of a High-Capacity MAb Capture Step Based on Cation-Exchange Chromatography*, BioProcess Int'l, vol. 7, pp. 26-34 (May 2009).
Lazar et al., *Matrix-assisted laser desorption/ionization mass spectrometry for the evaluation of the C-terminal lysine distributon of a recombinant monoclonal antibody*, Rapid Communications in Mass Spectrometry, vol. 18, pp. 239-244 (2004).
Leader et al., *Agalactosyl IgG in Aggregates from the Rheumatoid Joint*, Br. J. Rheumatol., 35:335-341 (1996).
Lienqueo et al., *Mathematical correlations for predicating protein retention times in hydrophobic interaction chromatography*, 978:71-79 (2002).

Ling et al., *Analysis of Monoclonal Antibody Charge Heterogeneity Using Ion-Exchange Chromatography on a Fully Biocompatible HPLC System*, Dionex (2009).
Lobo-Alfonso et al., *Benefits and Limitations of Protein Hydrolysates as Components of Serum-Free Media for Animal Cell Culture Applications, Protein Hydrolysates in Serum Free Media*, GIBCO Cell Culture, Invitrogen Corporation, Grand Island, New York, Chapter 4:55-78 (2010).
Lu et al., *Recent Advancement in Application of Hydrophobic Interaction Chromatography for Aggregate Removal in Industrial Purification Process*, 10:427-433 (2009).
Lubinieki et al., *Comparability assessments of process and product changes made during development of two different monoclonal antibodies*, Biologicals, vol. 39, pp. 9-22 (2011).
Luksa et al., *Purification of human tumor necrosis factor by membrane chromatography*, J. Chromatography A, 661:161-168 (1994).
Lund et al., *Control of IgG/Fc Glycosylation: A Comparison of Oligosaccharides from Chimeric Human/Mouse and Mouse Subclass Immunoglobulin Gs*, Molecular Immunology, 30(8):741-748 (1993).
Matsumoto et al., *Autoantibody Activity of IgG Rheumatoid Factor Increases with Decreasing Levels of Galactosylation and Sialylation*, J. Biochemistry, 128:621-628 (2000).
McCue et al., *Effect of phenyl sepharose ligand density on protein monomer/aggregate purification and separation using hydrophobic interaction chromatography*, J. of Chromatography A, 1216:209-909 (2009).
McLeod, "Adalimumab, etanercept and infliximab for the treatment of ankylosing spondylitis: a systematic review and economic evaluation," Health Technol. Assess. 11(28):1-158 (2006).
Meert et al., *Characterization of Antibody Charge Heterogeneity Resolved by Preparative Immobilized pH Gradients*, Analytical Chem., vol. 82, pp. 3510-3518 (2010).
Melter et al., *Adsorption of monoclonal antibody variants on analytical cation-exchange resin*, J. Chromatography A, vol. 1154, pp. 121-131 (2007).
Mizrahi, *Primatone RL in mammalian cell culture media*, Biotechnol. Bioeng., 19:1557-1561 (1977).
Moloney and Haltiwanger, *The O-linked fucose glycosylation pathway: indentification and characterization of a uridien diphosphoglucose: fucose-β1,3-glucosyltransferase activity from Chinese hamster ovary cells*, Glycobiology, 9:679-87 (1999).
Nyberg et al., *Metabolic Effects on Recombinant Interferon-γ Glycosylation in Continuous Culture of Chinese Hamster Ovary Cells*, Biotech. Bioeng., 62(3):336-347 (1999).
Onda et al., *Reduction of the Nonspecific Animal Toxicity of Anti-Tac (Fv)-PE38 by Mutations in the Framework Regions of the Fv Which Lower the Isoelectric Point*, J. Immunology, vol. 163, pp. 6072-6077 (1999).
Pacesetter, Beckman Coulter Newsletter, vol. 3, Issue 1 (Apr. 1999).
Raju, *Terminal sugars of Fc glycans influence antibody effector functions of IgGs*, Current Opinion in Immunology, 20:471-478 (2008).
Rao et al., *mAb Heterogeneity Characterization: MabPac Strong Cation-Exchanger Columns Designed to Extend Capabilities of mAb Analysis*, Tutorials (Mar. 15, 2011).
Rao et al., *Separation of Monoclonal Antibodies by Weak Cation-Exchange Chromatography Using ProPac and ProSwift Columns*, Dionex (available online 2010).
Rivinoja et al, *Elevated Golgi pH Impairs Terminal N L Glycosylation by Inducing Mislocalization of Golgi Glycosyltransferases*, J. Cell. Physiol., 220:144-154 (2009).
Robinson et al., *Characterization of a Recombinant Antibody Produced in the Course of a High Yield Fed-Batch Process*, Biotech. Bioeng., 44:727-735 (1994).
Rodriguez et al., *Enhanced Production of Monomeric Interferon-â by CHO Cells through the Control of Culture Conditions*, Biotechnol. Prog., 21:22-30 (2005).
Rosolem et al., *Manganese uptake and redistribution in soybean as affected by glyphosate*, Rev. Bras. Ciênc. Solo, 34:1915-1922 (2010).

(56) References Cited

OTHER PUBLICATIONS

Rudwaleit et al., Adalimumab is effective and well tolerated in treating patients with ankylosing spondylitis who have advanced spinal fusion, *Rhematology*, 48; 551-557 (2009).

Santora et al., *Determination of Recombinant Monoclonal Antibodies and Noncovalent Antigen TNFα Trimer Using Q-TOF Mass Spectrometry*, Spectroscopy, 17(5):50-57 (2002).

Schenerman et al., *CMC Strategy Forum Report*, BioProcess Technical (2004).

Schlaeger E.-J., *The protein hydrolysate, Primatone RL, is a cost-effective multiple growth promoter of mammalian cell culture in serum-containing and serum-free media and displays anti-apoptosis properties*, J. Immunol. Meth., 194:191-199 (1996).

Sheffield Bioscience, Bio-Science Technical Manual: Supplements for cell culture, fermentation, and diagnostic media, 43 pages (2011).

Shen et al., *Characterization of yeastolate fractions that promote insect cell growth and recombinant protein production*, Cytotechnology, 54:25-34 (2007).

Shi et al., *Real Time Quantitative PCR as a Method to Evaluate Xenotropic Murine Leukemia Virus Removal During Pharmaceutical Protein Purification*, Biotechnology & Bioengineering, vol. 87, No. 7, pp. 884-896 (Sep. 2004).

Shukla et al., *Downstream processing of monoclonal antibodies— Application of platform approaches*, J. of Chromatography B, 848:28-39 (2007).

Shukla et al., eds., *Process Scale Bioseparations for the Biopharmaceutical Industry*, (Taylor & Francis Group, Boca Raton FL) (2006).

Shukla et al., *Recent advances in large-scale production of monoclonal antibodies and related proteins*, Trends in Biotechnology, 28(5):253-261 (2010).

Shukla et al., *Strategies to Address Aggregation During Protein a Chromatography*, BioProcess International, 3:36-44 (2005).

Siemensma et al., Towards an Understanding of How Protein Hydrolysates Stimulate More Efficient Biosynthesis in Cultured Cells: *Protein Hydrolysates in Biotechnology,Bio-Science*, 36 pages (2010).

Tang et al., *Conformational characterization of the charge variants of a human IgG1 monoclonal antibody using H/D exchange mass spectrometry*, mAbs, vol. 5, pp. 114-125 (2013).

Thiansilakul et al., *Compositions, functional properties and antioxidative activity of protein hydrolysates prepared from round scad (Decapterus maruadsi)*, Food Chemistry, 103:1385-1394 (2007).

Tian et al., *Spectroscopic evaluation of the stabilization of humanized monoclonal antibodies in amino acid formulations*, Int'l J. of Pharmaceutics, vol. 335, pp. 20-31 (2007).

To, et al., Hydrophobic interaction chromatography of proteins: I. The effects of protein and adsorbent properties on retention and recovery, J. of Chromatography A, 1141:191-205 (2007).

Tritsch et al., *Spontaneous decomposition of glutamine in cell culture media*, Experimental Cell Research, 28:360-364 (1962).

Tsubaki et al., *C-terminal modification of monoclonal antibody drugs: Amidated species as a general product0related substance*, Int'l J. Biological Macromolecules, vol. 52, pp. 139-147 (2013).

Tugcu et al., *Maximizing Productivity of Chromatography Steps for Purification of Monoclonal Antibodies*, vol. 99, No. 3, pp. 599-613 (available online Aug. 2007).

Urech, D.M. et al., Anti-inflammatory and cartilage-protecting effects of an intra-articularly injected anti-TNFa single-chain Fv antibody (ESBA105) designed for local therapeutic use, Ann Rheum Dis, 69, 443-449, Mar. 16, 2009.

Van der Heijde et al., Adalimumab effectively reduces the signs and symptoms of active ankylosing spondylitis in patients with total spinal ankylosis, Arthritis & Rheumatism 67:1218-1221 (2008).

Van der Heijde et al., Efficacy and Safety of Adalimumab in Patients with Ankylosing Spondylitis, Arthritis & Rheumatism 54:2136-46 (2006).

Van der Heijde et al., Efficacy and Safety of Infliximab in Patients with Ankylosing Spondylitis, Arthritis & Rheumatism 52:582-591 (2005).

Wang et al., *Antibody Structure, Instability and Formulation*, J. Pharm. Sci., vol. 96, No. 1, pp. 1-26 (2007).

Wei et al., *Glyco-engineering of human IgG1-Fc through combined yeast expression and in vitro chemoenzymatic glycosylation*, National Institute of Health Public Access Author Manuscript, Biochemistry, 47(39):10294-10304 (2008).

Weitzhandler et al., *Protein variant separations by cation-exchange chromatography on tentacle-type polymeric stationary phases*, Proteomics, vol. 1, pp. 179-185 (2001).

Wong et al., *Impact of Dynamic Online Fed-Batch Strategies on Metabolism, Productivity and N-Glycosylation Quality in CHO Cell Cultures*, Biotechnol. Bioeng., 89(2):164-177 (2005).

Xie et al., *High Cell Density and High Monoclonal Antibody Production Through Medium Design and Rational Control in a Bioreactor*, Biotechnol. Bioeng., 51:725-729 (1996).

Yang et al., *Effect of Ammonia on the Glycosylation of Human Recombinant Erythropoietin in Culture*, Biotech. Progress, 16:751-759 (2000).

Zhang et al., *Mass Spectrometry for Structural Characterization of Therapeutic Antibodies*, Mass Spectrometry Reviews, 28:147-176 (2009).

Zhang, Y. et al., *Effects of peptone on hybridoma growth and monoclonal antibody formation*, Cytotechnology, 16:147-150 (1994).

Zhou, *Implementation of Advanced Technologies in Commercial MonoclonalAntibody Production*, Biotech. J., 3:1185-1200 (2008).

Zhu, *Mammalian cell protein expression for biopharmaceutical production*, Biotech.Adv., 30:1158-1170 (2012).

U.S. Appl. No. 15/187,425.

FIGURE 2B (SEQ ID NO. 4):
(SEQ ID NO. 3):

FIGURE 2C

| Sample | D2E7 | ZFN-B1 | Galtr-11 | Gal88-D2E7 | SA-D2E7 | Gal79-DVD |
|---|---|---|---|---|---|---|
| Sum Man 5-9 | 8% | 4.5% | 5% | 2.6% | 1% | 9% |
| G0F minus GlcNAc | 4% | 1% | - | - | - | - |
| G0F | 68% | 39% | 5% | 1% | 1% | 1% |
| Sum G1F/G2F | 18% | 53% | 80% | 88% | 10% | 79% |
| Sum G2S1F/G2S2F | - | 1% | 2% | - | 70% | - |
| other | 2% | 1.5% | 8% | 8.4% | 18% | 11% |

FIGURE 5C

| Mouse # | $t_{1/2}$ (hr) | $C_{max}$ (ug/mL) | $V_{ss}$ (L/kg) | IV (5 mg/kg) AUC (ug·hr/mL) | $AUC_{0-t}$ (ug·hr/mL) | $CL_B$ (L/hr/kg) | MRT (hr) |
|---|---|---|---|---|---|---|---|
| 3 | 587 | 110 | 0.110 | 35200 | 17500 | 0.000014 | 775.50537 |
| 5 | 262 | 121 | 0.0818 | 20600 | 15800 | 0.000024 | 336.10126 |
| Mean | 363° | 116 | 0.096 | 27900 | 16700 | 0.000019 | 555.80334 |
| SEM | 5.77 | | 0.0143 | 7310 | 833 | 0.000005 | 219.70206 |

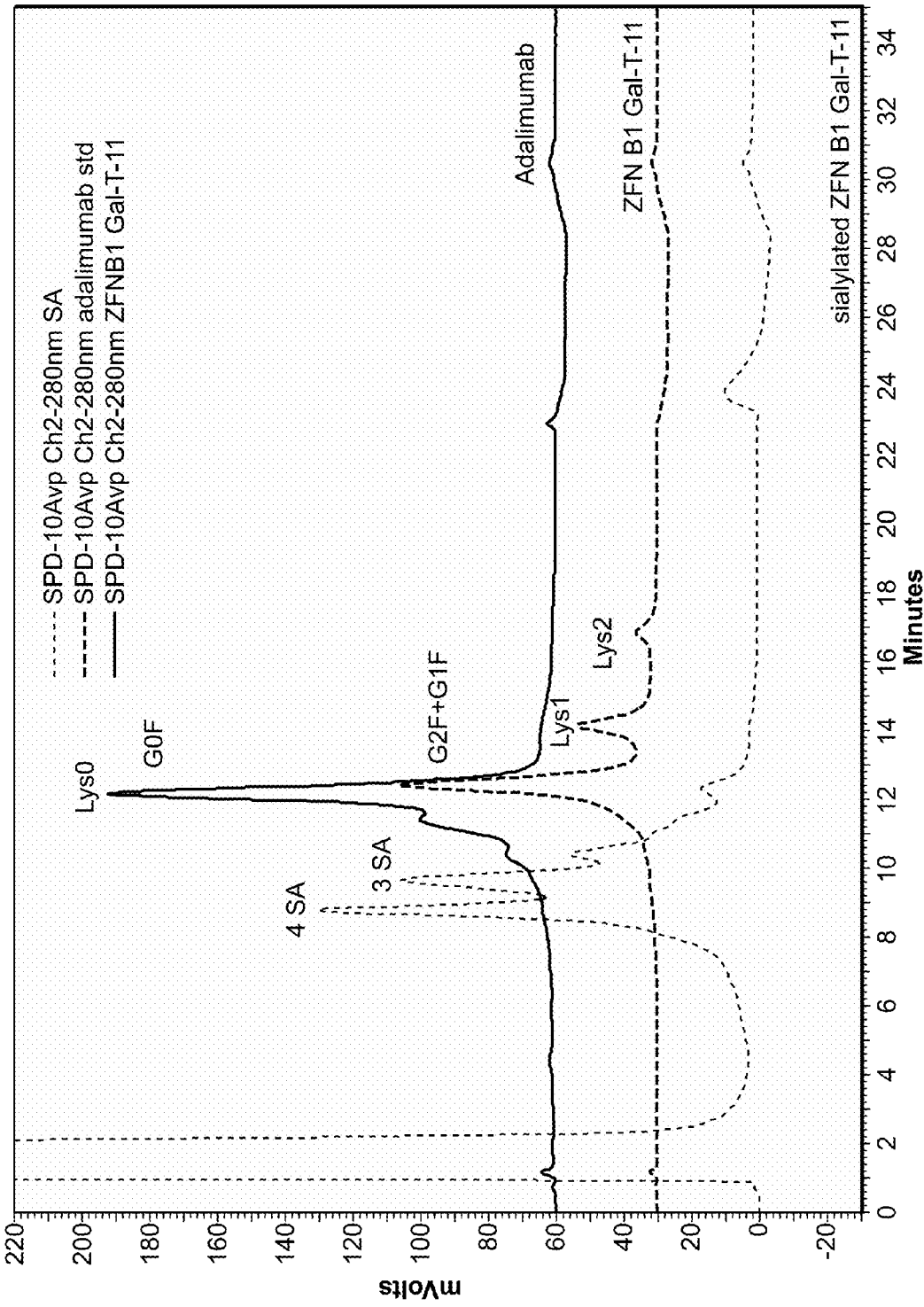

SEQUENCE LISTING

```
<160> NUMBER OF SEQ ID NOS: 4

<210> SEQ ID NO 1
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (451)..(451)
<223> OTHER INFORMATION: May or may not be present

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp His Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                    245                 250                 255
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
        450

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser His Ser Ile Arg Asn Tyr
            20                  25                  30

Leu Ser Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 3
<211> LENGTH: 1200
<212> TYPE: DNA
<213> ORGANISM: Mus sp.
<220> FEATURE:
<221> NAME/KEY: CDS
<222> LOCATION: (1)..(1197)

<400> SEQUENCE: 3 atg agg ttt cgt gag cag ttc ctg ggc ggc agc gcc gcg atg ccg ggc      48
Met Arg Phe Arg Glu Gln Phe Leu Gly Gly Ser Ala Ala Met Pro Gly
1               5                   10                  15 gcg acc ctg cag cgg gcc tgc cgc ctg ctc gtg gcc gtc tgc gcg ctg      96
Ala Thr Leu Gln Arg Ala Cys Arg Leu Leu Val Ala Val Cys Ala Leu
                20                  25                  30 cac ctc ggc gtc acc ctc gtc tat tac ctc tct ggc cgc gat ctg agc     144
His Leu Gly Val Thr Leu Val Tyr Tyr Leu Ser Gly Arg Asp Leu Ser
            35                  40                  45 cgc ctg ccc cag ttg gtc gga gtc tcc tct aca ctg cag ggc ggc acg     192
Arg Leu Pro Gln Leu Val Gly Val Ser Ser Thr Leu Gln Gly Gly Thr
        50                  55                  60 aac ggc gcc gca gcc agc aag cag ccc cca gga gag cag cgg ccg cgg     240
Asn Gly Ala Ala Ala Ser Lys Gln Pro Pro Gly Glu Gln Arg Pro Arg
65                  70                  75                  80 ggt gcg cgg ccg ccg cct cct tta ggc gtc tcc ccg aag cct cgc ccg     288
Gly Ala Arg Pro Pro Pro Pro Leu Gly Val Ser Pro Lys Pro Arg Pro
                85                  90                  95 ggt ctc gac tcc agc cct ggt gca gct tct ggc ccc ggc ttg aag agc     336
Gly Leu Asp Ser Ser Pro Gly Ala Ala Ser Gly Pro Gly Leu Lys Ser
            100                 105                 110 aac ttg tct tcg ttg cca gtg ccc acc acc act gga ctg ttg tcg ctg     384
Asn Leu Ser Ser Leu Pro Val Pro Thr Thr Thr Gly Leu Leu Ser Leu
        115                 120                 125 cca gct tgc cct gag gag tcc ccg ctg ctc gtt ggc ccc atg ctg att     432
Pro Ala Cys Pro Glu Glu Ser Pro Leu Leu Val Gly Pro Met Leu Ile
130                 135                 140 gac ttt aat att gct gtg gat ctg gag ctt ttg gca aag aag aac cca     480
Asp Phe Asn Ile Ala Val Asp Leu Glu Leu Leu Ala Lys Lys Asn Pro
145                 150                 155                 160 gag ata aag acg ggc ggc cgt tac tcc ccc aag gac tgt gtc tct cct     528
Glu Ile Lys Thr Gly Gly Arg Tyr Ser Pro Lys Asp Cys Val Ser Pro
                165                 170                 175 cac aag gtg gcc atc atc atc cca ttc cgt aac cgg cag gag cat ctc     576
His Lys Val Ala Ile Ile Ile Pro Phe Arg Asn Arg Gln Glu His Leu
            180                 185                 190 aaa tac tgg ctg tat tat ttg cat ccc atc ctt cag cgc cag caa ctc     624
Lys Tyr Trp Leu Tyr Tyr Leu His Pro Ile Leu Gln Arg Gln Gln Leu
        195                 200                 205 gac tat ggc atc tac gtc atc aat cag gct gga gac acc atg ttc aat     672
Asp Tyr Gly Ile Tyr Val Ile Asn Gln Ala Gly Asp Thr Met Phe Asn
```

```
Asp Tyr Gly Ile Tyr Val Ile Asn Gln Ala Gly Asp Thr Met Phe Asn
    210                 215                 220 cga gct aag ctg ctc aat att ggc ttt caa gag gcc ttg aag gac tat       720
Arg Ala Lys Leu Leu Asn Ile Gly Phe Gln Glu Ala Leu Lys Asp Tyr
225                 230                 235                 240 gat tac aac tgc ttt gtg ttc agt gat gtg gac ctc att ccg atg gac       768
Asp Tyr Asn Cys Phe Val Phe Ser Asp Val Asp Leu Ile Pro Met Asp
                245                 250                 255 gac cgt aat gcc tac agg tgt ttt tcg cag cca cgg cac att tct gtt       816
Asp Arg Asn Ala Tyr Arg Cys Phe Ser Gln Pro Arg His Ile Ser Val
            260                 265                 270 gca atg gac aag ttc ggg ttt agc ctg cca tat gtt cag tat ttt gga       864
Ala Met Asp Lys Phe Gly Phe Ser Leu Pro Tyr Val Gln Tyr Phe Gly
        275                 280                 285 ggt gtc tct gct ctc agt aaa caa cag ttt ctt gcc atc aat gga ttc       912
Gly Val Ser Ala Leu Ser Lys Gln Gln Phe Leu Ala Ile Asn Gly Phe
    290                 295                 300 cct aat aat tat tgg ggt tgg gga gga gaa gat gac gac att ttt aac       960
Pro Asn Asn Tyr Trp Gly Trp Gly Gly Glu Asp Asp Asp Ile Phe Asn
305                 310                 315                 320 aga tta gtt cat aaa ggc atg tct ata tca cgt cca aat gct gta gta      1008
Arg Leu Val His Lys Gly Met Ser Ile Ser Arg Pro Asn Ala Val Val
                325                 330                 335 ggg agg tgt cga atg atc cgg cat tca aga gac aag aaa aat gag ccc      1056
Gly Arg Cys Arg Met Ile Arg His Ser Arg Asp Lys Lys Asn Glu Pro
            340                 345                 350 aat cct cag agg ttt gac cgg atc gca cat aca aag gaa acg atg cgc      1104
Asn Pro Gln Arg Phe Asp Arg Ile Ala His Thr Lys Glu Thr Met Arg
        355                 360                 365 ttc gat ggt ttg aac tca ctt acc tac aag gtg ttg gat gta cag aga      1152
Phe Asp Gly Leu Asn Ser Leu Thr Tyr Lys Val Leu Asp Val Gln Arg
    370                 375                 380 tac ccg tta tat acc caa atc aca gtg gac atc ggg aca ccg aga tag      1200
Tyr Pro Leu Tyr Thr Gln Ile Thr Val Asp Ile Gly Thr Pro Arg
385                 390                 395

<210> SEQ ID NO 4
<211> LENGTH: 399
<212> TYPE: PRT
<213> ORGANISM: Mus sp.

<400> SEQUENCE: 4

Met Arg Phe Arg Glu Gln Phe Leu Gly Gly Ser Ala Ala Met Pro Gly
1               5                   10                  15

Ala Thr Leu Gln Arg Ala Cys Arg Leu Val Ala Val Cys Ala Leu
            20                  25                  30

His Leu Gly Val Thr Leu Val Tyr Tyr Leu Ser Gly Arg Asp Leu Ser
        35                  40                  45

Arg Leu Pro Gln Leu Val Gly Val Ser Ser Thr Leu Gln Gly Gly Thr
    50                  55                  60

Asn Gly Ala Ala Ala Ser Lys Gln Pro Pro Gly Glu Gln Arg Pro Arg
65                  70                  75                  80

Gly Ala Arg Pro Pro Pro Leu Gly Val Ser Pro Lys Pro Arg Pro
                85                  90                  95

Gly Leu Asp Ser Ser Pro Gly Ala Ala Ser Gly Pro Gly Leu Lys Ser
            100                 105                 110

Asn Leu Ser Ser Leu Pro Val Pro Thr Thr Thr Gly Leu Leu Ser Leu
        115                 120                 125
```

-continued

```
Pro Ala Cys Pro Glu Glu Ser Pro Leu Leu Val Gly Pro Met Leu Ile
    130                 135                 140
Asp Phe Asn Ile Ala Val Asp Leu Glu Leu Leu Ala Lys Lys Asn Pro
145                 150                 155                 160
Glu Ile Lys Thr Gly Gly Arg Tyr Ser Pro Lys Asp Cys Val Ser Pro
                165                 170                 175
His Lys Val Ala Ile Ile Ile Pro Phe Arg Asn Arg Gln Glu His Leu
                180                 185                 190
Lys Tyr Trp Leu Tyr Tyr Leu His Pro Ile Leu Gln Arg Gln Gln Leu
            195                 200                 205
Asp Tyr Gly Ile Tyr Val Ile Asn Gln Ala Gly Asp Thr Met Phe Asn
    210                 215                 220
Arg Ala Lys Leu Leu Asn Ile Gly Phe Gln Glu Ala Leu Lys Asp Tyr
225                 230                 235                 240
Asp Tyr Asn Cys Phe Val Phe Ser Asp Val Asp Leu Ile Pro Met Asp
                245                 250                 255
Asp Arg Asn Ala Tyr Arg Cys Phe Ser Gln Pro Arg His Ile Ser Val
                260                 265                 270
Ala Met Asp Lys Phe Gly Phe Ser Leu Pro Tyr Val Gln Tyr Phe Gly
            275                 280                 285
Gly Val Ser Ala Leu Ser Lys Gln Gln Phe Leu Ala Ile Asn Gly Phe
    290                 295                 300
Pro Asn Asn Tyr Trp Gly Trp Gly Gly Glu Asp Asp Asp Ile Phe Asn
305                 310                 315                 320
Arg Leu Val His Lys Gly Met Ser Ile Ser Arg Pro Asn Ala Val Val
                325                 330                 335
Gly Arg Cys Arg Met Ile Arg His Ser Arg Asp Lys Lys Asn Glu Pro
                340                 345                 350
Asn Pro Gln Arg Phe Asp Arg Ile Ala His Thr Lys Glu Thr Met Arg
            355                 360                 365
Phe Asp Gly Leu Asn Ser Leu Thr Tyr Lys Val Leu Asp Val Gln Arg
    370                 375                 380
Tyr Pro Leu Tyr Thr Gln Ile Thr Val Asp Ile Gly Thr Pro Arg
385                 390                 395
```

GLYCOENGINEERED BINDING PROTEIN COMPOSITIONS

RELATED APPLICATIONS

The present application is a continuation of U.S. patent application Ser. No. 14/542,281, filed on Nov. 14, 2014, which in turn, claims priority to U.S. Provisional Application No. 61/904,487, filed Nov. 15, 2013 and U.S. Provisional Application No. 62/051,669, filed Sep. 17, 2014, the contents of which are hereby incorporated by reference herein in their entireties.

FIELD OF THE INVENTION

The present invention relates to compositions of recombinant Fc binding proteins, e.g., recombinant antibodies, which exhibit improved properties (e.g., a reduced anti-drug immune response) as a result of their optimized glycosylation profile.

SEQUENCE LISTING

The instant application contains a Sequence Listing which has been submitted electronically in ASCII format and is hereby incorporated by reference in its entirety. Said ASCII copy, created on Dec. 23, 2014, is named 5629110BBI-395_SL.txt and is 15,783 bytes in size.

BACKGROUND

The use of therapeutic binding proteins has revolutionized the treatment of many diseases, including cancer, inflammatory bowel disease (IBD), ankylosing spondylitis, multiple sclerosis, psoriasis and rheumatoid arthritis (RA). Despite their success in improving the quality of life of patients, long-term treatment with therapeutic binding proteins is often associated with the emergence of anti-drug antibodies (ADA) against the therapeutic agent. The development of ADA results in progressively lower serum drug levels and a diminished treatment efficacy.

For example, a 2011 study of rheumatoid arthritis patients treated with adalimumab revealed the development of anti-drug antibodies resulted in significantly lower remission rates. Two-thirds of the anti-adalimumab antibody-positive patients developed antibodies to the drug within the first 28 weeks of treatment. The presence of anti-adalimumab antibodies was further shown to substantially reduce serum adalimumab concentrations Similar results have been reported for infliximab, adalimumab, and natalizumab (see Bartelds et al., JAMA. 2011; 305(14):1460-1468). Such ADA immune responses, therefore, decrease the overall efficacy and utility of therapeutic binding proteins.

Accordingly, there is a need in the art for recombinant protein therapeutics compositions that exhibit a reduced ADA response relative to current therapeutic binding proteins.

SUMMARY OF THE INVENTION

The present disclosure provides novel binding protein compositions exhibiting a surprisingly reduced anti-drug antibody (ADA) immune response as a result of their optimized glycoprofile. These compositions generally comprise a population of Fc domain-containing binding proteins that are hypergalactosylated (e.g., enriched for binding proteins with highly galactosylated glycoforms) and/or hypomannosylated (e.g., deficient in binding proteins with highly mannosylated glycoforms) on the Fc glycosylation site of the binding proteins. Thus, the compositions of the invention may be characterized as having glycan structures with a G/M ratio (galactose content/mannose content) of greater than 1:1, e.g., greater than 10:1, 50:1 or 99:1. Also provided are methods of treating a disorder using these compositions, and methods and host cells for making such compositions.

The binding protein compositions disclosed herein are particularly advantageous in that they exhibit a longer serum half-life than non-hypergalactosylated and/or non-hypomannosylated Fc domain-containing binding protein compositions and, therefore, require less frequent dosing to be efficacious.

Accordingly, in one aspect, the instant disclosure provides a hypergalactosylated population of Fc domain-containing binding proteins, wherein the total percent amount of G1 and G2 glycoforms in the population is more than 50% (e.g., more than 80%, more than 90%, more than 95% or more than 99%). In certain embodiments, the total percent amount of G1 and G2 glycoforms in the population is more than 80%. In certain embodiments, the G1 and G2 glycoforms in the population are fucosylated. In certain embodiments, the total percent amount of G1, G2, G1S1, G2S1 and G2S2 glycoforms in the population is more than 50% (e.g., more than 80%, or more than 99%). In certain embodiments, the total percent amount of G1, G2, G1S1, G2S1 and G2S2 glycoforms in the population is more than 80%. In certain embodiments, the G1, G2, G1S1, G2S1 and G2S2 glycoforms in the population are fucosylated.

In other aspects, the binding protein compositions of the invention are also hypomannosylated. For example, the binding protein composition of the inventions may exhibit less than 10% of highly mannosylated glycoforms (oligomannose species, e.g., M3-M9 glycoforms) in population of Fc-domain—containing binding proteins. In certain embodiments, less than 5% (e.g., less than 1% or less than 0.1%) of the Fc domain-containing binding proteins in the population are highly mannosylated.

In certain embodiments, the binding protein compositions of the invention have a G/M ratio of greater than 1:1 (e.g., at least 2:1, 5:1, 10:1, 80:1 or at least 99:1). In certain embodiments, the population of Fc domain-containing binding proteins has a G1/2:M ratio of at least 10:1 (e.g., at least 50:1, at least 80:1, or at least 99:1). In certain embodiments, the population of Fc domain-containing binding proteins has a GS:M ratio of at least 10:1 (e.g., at least 50:1, at least 80:1, or at least 99:1). In certain embodiments, the population of Fc domain-containing binding proteins has a Gtotal:M ratio of at least 10:1 (e.g., at least 50:1, at least 80:1, or at least 99:1).

In certain embodiments, the Fc domain-containing binding proteins in the population comprise an antigen-binding portion of an antibody. In certain embodiments, the antibody is selected from the group consisting of alemtuzumab, bevacizumab, cetuximab, edrecolomab, gemtuzumab ozogamicin, ibritumomab tiuxetan, ofatumumab, panitumumab, rituximab, tositumomab, trastuzumab, arcitumomab, capromab pendetide, nofetumomab, satumomab, basiliximab, daclizumab, muromonab-cd3, infliximab, natalizumab, adalimumab, certolizumab, golimumab, infliximab, tocilizumab, omalizumab, abciximab, bevacizumab, ranibzumab, natalizumab, efalizumab, ustekinumab, palivizumab, ruplizumab, denosumab, eculizumab, alefacept, abatacept, etanercept, romiplostim, rilonacept, aflibercept, belatacept, or rilonacept. In certain embodiments, the Fc domain-containing binding proteins in the population comprise a non-antibody antigen-binding portion. In certain embodiments, the hypergalactosylated population is a hypergalactosylated population of dual variable domain immunoglobulins (DVD-Ig).

In certain aspects, the invention provides compositions wherein the binding proteins in the population bind to tumor necrosis factor alpha (TNFα). In certain embodiments, the binding protein is selected from the group consisting of etanercept, infliximab, adalimumab, or golimumab. In certain exemplary embodiments, the binding protein is the anti-TNF antibody adalimumab or a variant thereof. In certain embodiments, the anti-TNF antibody is an Fc variant of adalimumab (D2E7) comprising the heavy and light chain variable region sequences of adalimumab and a variant Fc region with an amino acid substitution that confers enhanced serum half-life. In certain exemplary embodiments, the variant Fc region is a human IgG1 Fc region comprising the mutations T250Q and M428L relative to a wild-type human IgG1 sequence (wherein amino acid numbering is according to the EU numbering convention as in Kabat). In other embodiments, the anti-TNF antibody is a variant of adalimumab which exhibits pH-sensitive binding to the TNF antigen. In one exemplary embodiment, the pH-sensitive variant of adalimumab is a D2E7SS22 comprising the heavy chain of SEQ ID NO: 1 and the light chain of SEQ ID NO: 2. In another exemplary embodiment, the pH-sensitive variant comprises the heavy and light chain variable regions of D2E7SS2 and a variant Fc region (e.g., a human IgG1 Fc region comprising the mutations T250Q and M428L relative to a wild-type human IgG1 sequence).

In certain embodiments, the binding compositions of the invention are produced in a cultured mammalian host cell line (e.g., a CHO cell line). In certain embodiments, the host cell line has been glycoengineered to produce the hypergalactosylated and/or hypomannosylated binding proteins of the invention. In certain exemplary embodiments, the binding proteins of the invention are obtained from a glycoengineered CHO cell. In one exemplary embodiment, the glycoengineered CHO cell contains a heterologous galactosyltransferase gene (e.g., mouse galactosyltransferase Beta 1,4). In another exemplary embodiment, the glycoengineered CHO cell contains a knockdown of one of the alleles of the Beta galactosidase gene. Exemplary glycoengineered host cells include the GALtr11 CHO cell line and the ZFN-B1 CHO cell line described in Examples 1 and 2 herein, respectively.

In a second aspect, the instant disclosure provides a method of reducing a subject's anti-drug antibody (ADA) response to a population of Fc domain-containing binding proteins, the method comprising glycoengineering (e.g., hypergalactosylating and/or hypomannosylating) a population of Fc domain-containing binding proteins by increasing the G/M ratio of the population of Fc domain-containing binding proteins, such that the glycoengineered population of Fc domain-containing binding proteins has a greater serum half-life than the non-glycoengineered population of Fc domain-containing binding proteins. In certain embodiments, said glycoengineering comprises expressing the Fc domain-containing binding proteins in a glycoengineered host cell (e.g., a CHO cell that has been glycoengineered to express hypergalactosylated and/or hypomannosylated binding proteins), and isolating the hypergalactosylated and/or hypomannosylated binding proteins from the host cell.

In certain embodiments of the second aspect, the population is glycoengineered such that the total percent amount of G1 and G2 glycoforms in the hypergalactosylated population is more than 80%. In certain embodiments of the second aspect, the G1 and G2 glycoforms in the hypergalactosylated population are fucosylated. In certain embodiments of the second aspect, the total percent amount of G1, G2, G1S1, G2S1 and G2S2 glycoforms in the hypergalactosylated population is more than 50% (e.g., more than 80%, or more than 99%). In certain embodiments of the second aspect, the total percent amount of G1, G2, G1S1, G2S1 and G2S2 glycoforms in the hypergalactosylated population is more than 80%. In certain embodiments of the second aspect, the G1, G2, G1S1, G2S1 and G2S2 glycoforms in the hypergalactosylated population are fucosylated.

In certain embodiments of the second aspect, the methods of the invention comprise glycoengineering a population of Fc domain-containing binding proteins such that the population exhibits less than 10% of highly mannosylated glycoforms (oligomannose species, e.g., M3-M9 glycoforms). In certain embodiments of the second aspect, less than 5% of the Fc domain-containing binding proteins in the population comprise M3-M9 glycoforms. In certain embodiments of the second aspect, less than 1% of the Fc domain-containing binding proteins in the population comprise M3-M9 glycoforms. In certain embodiments of the second aspect, less than 0.1% of the Fc domain-containing binding proteins in the population comprise M3-M9 glycoforms.

In certain embodiments of the second aspect, the methods of the invention comprise glycoengineering a population of Fc domain-containing binding proteins such that population of Fc domain-containing binding proteins has a G1/2:M ratio of at least 10:1 (e.g., at least 50:1, at least 80:1, or at least 99:1). In certain embodiments of the second aspect, the population of Fc domain-containing binding proteins has a GS:M ratio of at least 10:1 (e.g., at least 50:1, at least 80:1, or at least 99:1). In certain embodiments of the second aspect, the population of Fc domain-containing binding proteins has a Gtotal:M ratio of at least 10:1 (e.g., at least 50:1, at least 80:1, or at least 99:1).

In certain embodiments of the second aspect, the Fc domain-containing binding proteins in the population comprise an antigen-binding portion of an antibody. In certain embodiments of the second aspect, the Fc domain-containing binding proteins in the population comprise a non-antibody antigen-binding portion. In certain embodiments of the second aspect, the Fc domain-containing binding proteins in the hypergalactosylated population comprise a dual variable domain immunoglobulin (DVD-Ig).

In certain embodiments of the second aspect, the binding proteins of the invention are selected from the group consisting of alemtuzumab, bevacizumab, cetuximab, edrecolomab, gemtuzumab ozogamicin, ibritumomab tiuxetan, ofatumumab, panitumumab, rituximab, tositumomab, trastuzumab, arcitumomab, capromab pendetide, nofetumomab, satumomab, basiliximab, daclizumab, muromonab-cd3, infliximab, natalizumab, adalimumab, certolizumab, golimumab, infliximab, tocilizumab, omalizumab, abciximab, bevacizumab, ranibzumab, natalizumab, efalizumab, ustekinumab, palivizumab, ruplizumab, denosumab, eculizumab, alefacept, abatacept, etanercept, romiplostim, rilonacept, aflibercept, belatacept, or rilonacept.

In certain embodiments of the second aspect, the binding proteins of the invention comprise an antigen-binding portion that binds to tumor necrosis factor alpha (TNFα). In certain embodiments, the binding portion is selected from the group consisting etanercept, infliximab, adalimumab, or golimumab. In certain exemplary embodiments, the binding protein is adalimumab. In other exemplary embodiments, the binding protein is an Fc variant of adalimumab. In other embodiments, the binding protein is D2E7SS22 or an Fc variant thereof.

In certain embodiments, the compositions of the invention do not exhibit an increased level of antibody-dependent cellular cytotoxicity (ADCC) activity and/or an increased level of complement-dependent cellular cytotoxicity (CDC) activity as compared to a composition that is not glycoengineered according to the methods of the invention (e.g., a composition that is not hypergalactosylated and/or hypomannosylated).

In a third aspect, the instant disclosure provides a glycoengineered host cell (e.g., a CHO cell) that produces a glycoengineered population of Fc domain-containing binding proteins having an enhanced G/M ratio of greater than 10:1 (e.g., greater than 50:1, 90:1 or 99:1). In certain embodiments, the glycoengineered population of Fc domain-containing binding proteins has one or more of the following properties: the total percent amount of G1 and G2 glycoforms in the population is more than 50% (e.g., more than 80%, or more than 99%); the total percent amount of G1, G2, G1S1, G2S1 or G2S2 glycoforms in the population is more than 50% (e.g., more than 80%, or more than 99%); less than 10% (e.g., less than 1%, or less than 0.1%) of the Fc domain-containing binding proteins in the population comprise highly mannosylated (e.g., M3-M9) glycoforms; a G1/2:M ratio of at least 10:1 (e.g., at least 50:1, at least 80:1, or at least 99:1): a GS:M ratio of at least 10:1 (e.g., at least 50:1, at least 80:1, or at least 99:1); or a Gtotal:M ratio of at least 10:1 (e.g., at least 50:1, at least 80:1, or at least 99:1). In certain embodiments of the third aspect, the G1, G2, G1S1, G2S1 or G2S2 glycoforms in the hypergalactosylated population are fucosylated.

In a fourth aspect, the instant disclosure provides a method of treating a disorder in a subject in need thereof, comprising administering to the subject an effective amount of the hypergalactosylated population of Fc domain-containing binding proteins described herein. In certain embodiments of the fourth aspect, the disorder is a TNFα associated disorder.

BRIEF DESCRIPTION OF THE DRAWINGS

The skilled artisan will understand that the drawings, described below, are for illustration purposes only. The figures are not intended to limit the scope of the teachings in any way.

FIG. 2B shows the DNA sequence (SEQ ID NO: 3) and corresponding amino acid sequence (SEQ ID NO: 4) of the mouse beta1-4 galactosyltransferase.

FIG. 2C shows the percentage of individual glycoforms of anti-human TNFα expressed in standard and High-Gal CHO cell lines. D2E7 is adalimumab (Humira®) expressed in a standard CHO production cell line, ZFN-B1 is adalimumab expressed in a CHO cell line with a knockout in one of the alleles of the beta galactosidase gene; Galtr-11 and Gal88-D2E7 are glycoengineered adalimumab preparations obtained from CHO cell lines overexpressing β-1, 4 galactosyltransferase; SA-D2E7 is a glycoengineered adalimumab preparation obtained from a CHO cell line with a knockout in one of the alleles of the beta galactosidase gene and overexpressing β-1, 4 galactosyltransferase (ZFN B1 Gal-T-11) and further subjected to in vitro sialyltransferase treatment and ion-exchange purification; and Gal79 DVD-Ig is a glycoengineered IL17×TNF DVD-Ig (ABT-122) obtained from a CHO cell line overexpressing β-1, 4 galactosyltransferase.

FIG. 5C shows the pharmacokinetic (PK) parameters of the glycoengineered anti-TNFα High Galactose mAb ZFN-B-1 (lot 2168407) after 5 mg/kg IV Dosing in CD-1 Mice.

FIG. 7C depicts an exemplary ion exchange chromatogram (WCX-10 HPLC) of the Galtr-11 (blue trace, second from top) and SA-D2E7 (bottom green trace) glycoengineered binding compositions of the invention, as compared to a non-glycoengineered form of adalimumab (Humira®; top red trace). The addition of sialic acid imparts a charge to the glycan resulting in earlier elution from the ion-exchange column.

DETAILED DESCRIPTION OF THE INVENTION

Figure 1A:
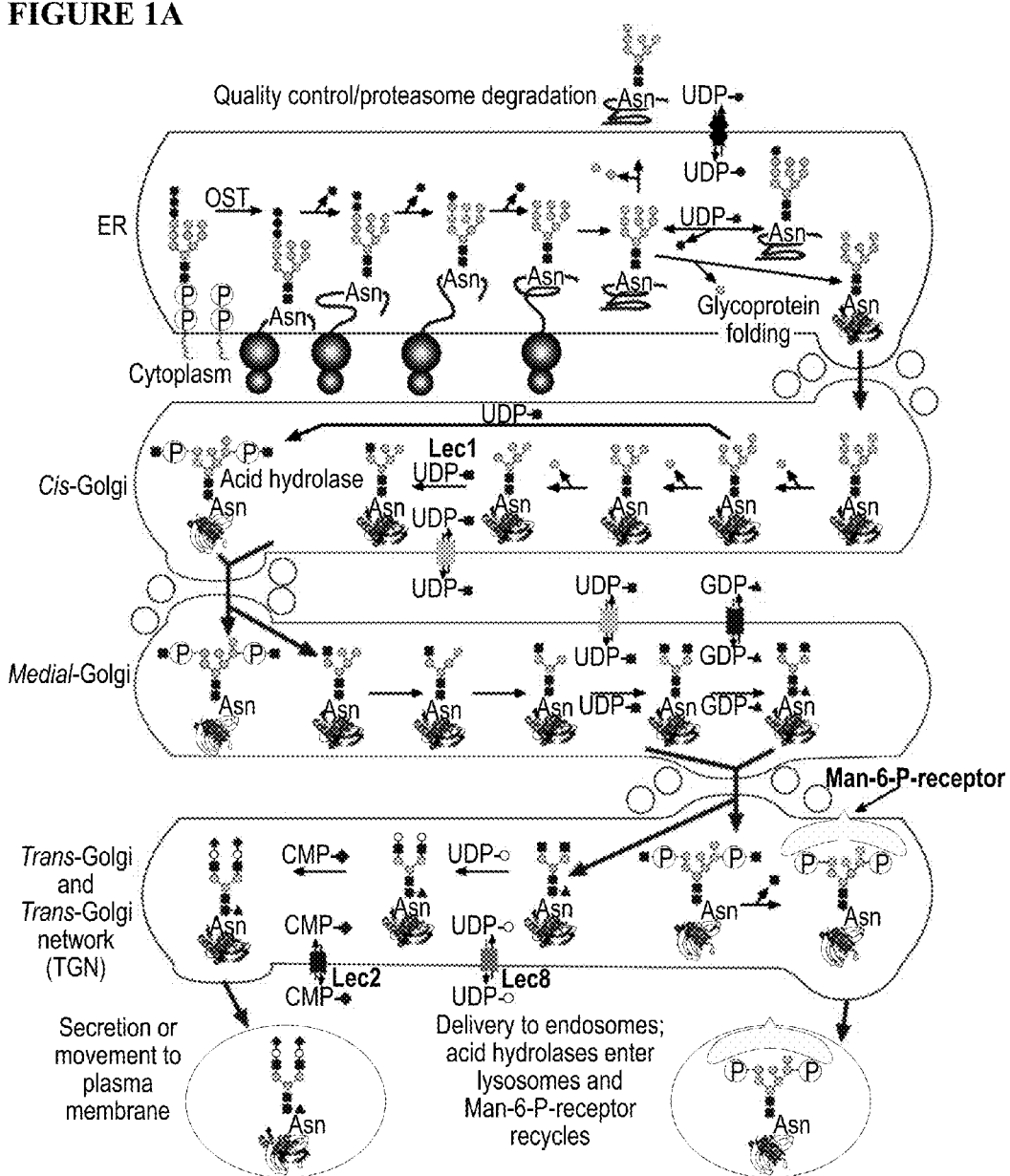
FIG. 1A is a schematic of the processing and maturation of an N-glycan. The mature Dol-P-P-glycan is transferred to Asn-X-Ser/Thr sequons during protein synthesis as proteins are being translocated into the ER. Following transfer of the 14-sugar $Glc_3Man_9GlcNAc_2$ glycan to protein, glucosidases in the ER remove the three glucose residues, and ER mannosidase removes a mannose residue. These reactions are intimately associated with the folding of the glycoprotein assisted by the lectins calnexin and calreticulin, and they determine whether the glycoprotein continues to the Golgi or is degraded. Another lectin, termed EDEM (ER degradation-enhancing α-mannosidase I-like protein), binds to mannose residues on misfolded glycoproteins and escorts them via retrotranslocation into the cytoplasm for degradation. For most glycoproteins, additional mannose residues are removed in the cis compartment of the Golgi until $Man_5GlcNAc_2Asn$ is generated. The action of G1cNAcT-1 on $Man_5GlcNAc_2Asn$ in the medial-Golgi initiates the first branch of an N-glycan. The action of α-mannosidase II generates the substrate for G1cNAcT-II. The resulting biantennary N-glycan is extended by the addition of fucose, galactose, and sialic acid to generate a complex N-glycan with two branches (reviewed in Annual Review of Biochemistry, from R. Kornfeld and S. Kornfeld. 1985. Annu. Rev. Biochem. 54: 631-634).
Figure 1B:
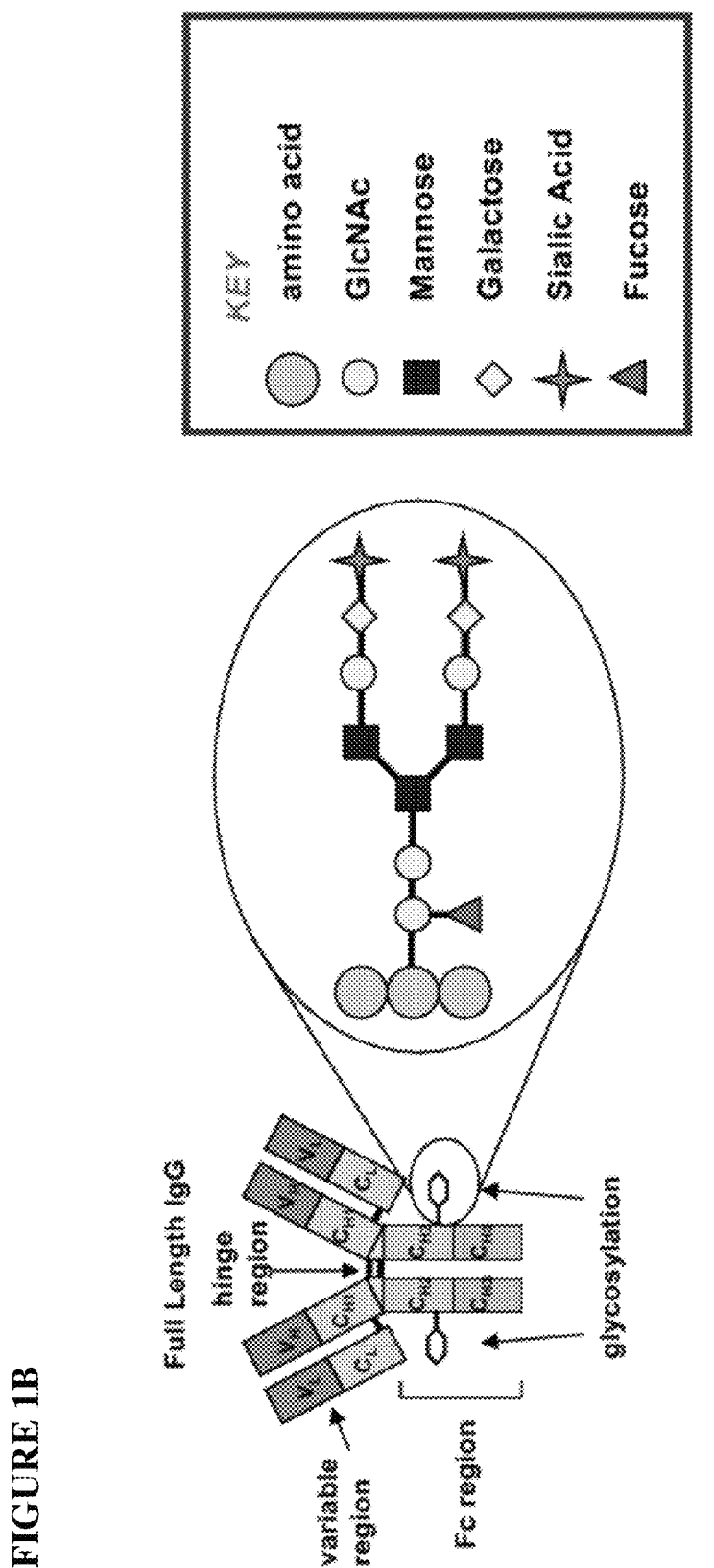
FIG. 1B is a schematic of an exemplary N-Glycan structure of an Fc region of an antibody.

The present disclosure provides novel glycoengineered binding protein compositions exhibiting a surprisingly reduced anti-drug antibody (ADA) immune response as a result of their optimized glycoprofile. These compositions generally comprise a population of Fc domain-containing binding proteins that are hypergalactosylated (e.g., enriched for binding proteins with highly galactosylated glycoforms) and/or hypomannosylated (e.g., deficient in binding proteins with highly mannosylated glycoforms) on the Fc glycosylation site of the binding proteins. Thus, the compositions of the invention may be characterized as having glycan structures with a G/M ratio (galactose content/mannose content) of greater than 1:1, e.g., greater than 10:1, 50:1 or 99:1. Also provided are methods of treating a disorder using these compositions, and methods and host cells for making such compositions.

The glycoengineered binding protein compositions disclosed herein are particularly advantageous in that they exhibit a longer serum half-life than non-glycoengineered Fc domain-containing binding protein compositions and, therefore, require less frequent dosing to be efficacious.

I. Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art.

In order that the present invention may be more readily understood, certain terms are first defined.

As used herein the term "Fc domain-containing binding protein" refers to a protein that specifically binds to an antigen, wherein the protein comprises an Fc domain, or an Fc-receptor binding fragment thereof, comprising an N-glycan. In certain embodiments, the N-glycan is an N-linked biantennary glycans present in the CH2 domain of an immunoglobulin constant (Fc) region (e.g., at EU position 297). "N-glycans" are attached at an amide nitrogen of an asparagine or an arginine residue in a protein via an N-acetylglucosamine residue. These "N-linked glycosylation sites" occur in the peptide primary structure containing, for example, the amino acid sequence asparagine-X-serine/threonine, where X is any amino acid residue except proline and aspartic acid. Such N-Glycans are fully described in, for example, Drickamer K, Taylor M E (2006). Introduction to Glycobiology, 2nd ed., which is incorporated herein by reference in its entirety.

In one embodiment, "N glycan" refers to the Asn-297 N-linked biantennary glycans present in the CH2 domain of an immunoglobulin constant (Fc) region. These oligosaccharides may contain terminal mannose, N-acetyl-glucosamine, Galactose or Sialic acid (see FIGS. 1C and 1D).

As used herein, the term "glycoengineering" refers to any art-recognized method for altering the glycoform profile of a binding protein composition. Such methods include expressing a binding protein composition in a genetically engineered host cell (e.g., a CHO cell) that has been genetically engineered to express a heterologous glycosyltransferase or glycosidase. In other embodiments, the glycoengineering methods comprise culturing a host cell under conditions that bias for particular glycoform profiles.

As used herein the term "hypergalactosylated population" refers to a population of Fc domain-containing binding proteins in which the galactose content of the N glycan is increased as compared to a reference population of Fc domain-containing binding proteins having the same amino acid sequence. A hypergalactosylated population can be expressed as having an increased number of G1 and G2 glycoforms as compared to the reference population of Fc domain-containing binding proteins.

As used herein, the term "hypomannosylated population" refers to a population of Fc domain-containing binding proteins in which the mannose content of the N glycan is decreased as compared to a reference population of Fc domain-containing binding proteins having the same amino acid sequence. A hypomannosylated population can be expressed as having a decreased number of oligomannose glycoforms (e.g., M3-M9 glycoforms) as compared to the reference population of Fc domain-containing binding proteins. In some embodiments, the mannose content is determined by measuring the content of one or more of oligomannose glycoforms selected from the group consisting of Man3, Man4, Man5, Man6, Man7, Man 8 and Man 9. In other embodiments, the oligomannose content is determined by measuring at least Man 5, Man 6, and Man 7. In certain embodiments, the oligomannose content is determined by measuring all M3-M9 glycoforms.

Figure 1C:
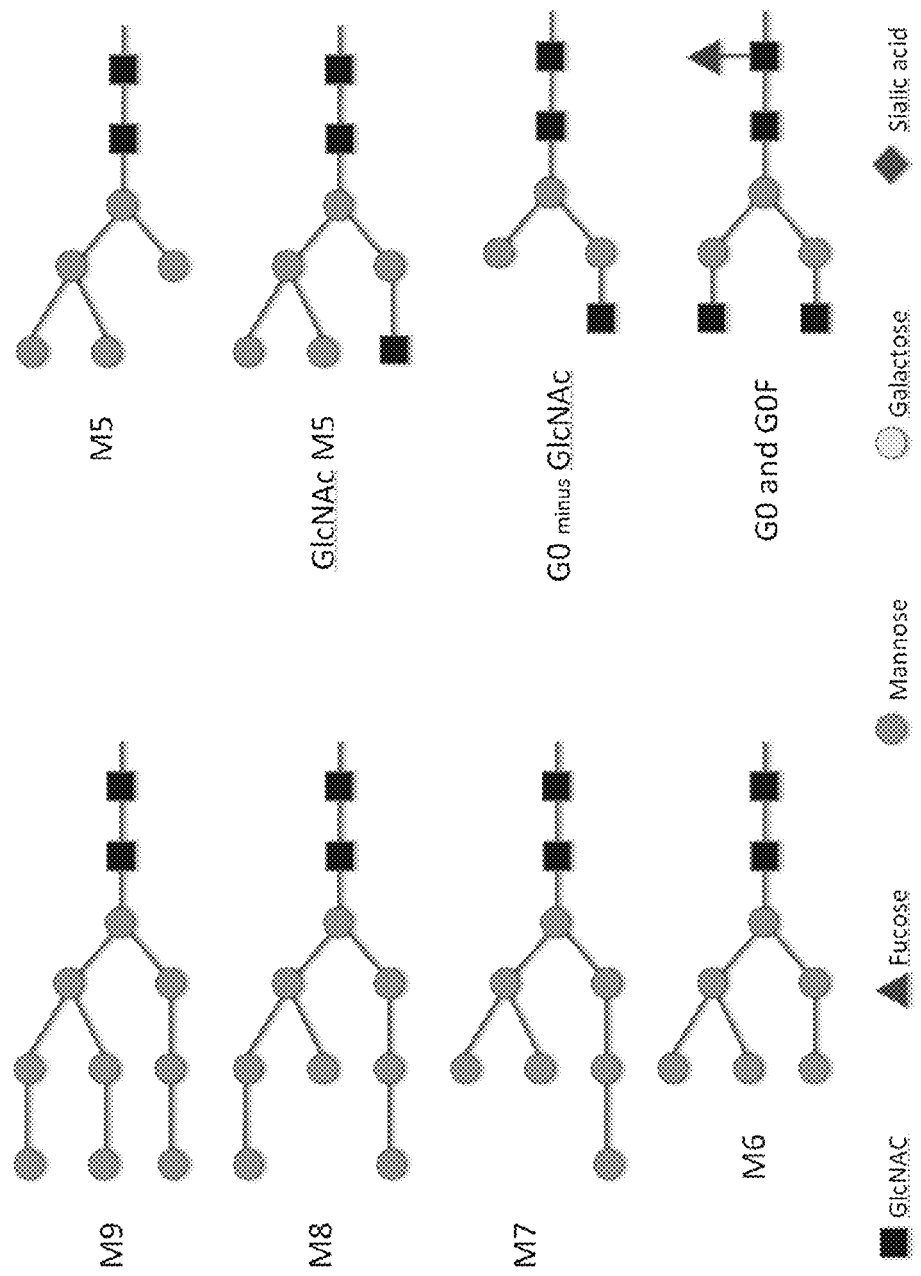
FIG. 1C is a schematic depicting exemplary non-galactosylated glycans imparting immunogenic properties to biologics.
Figure 1D:
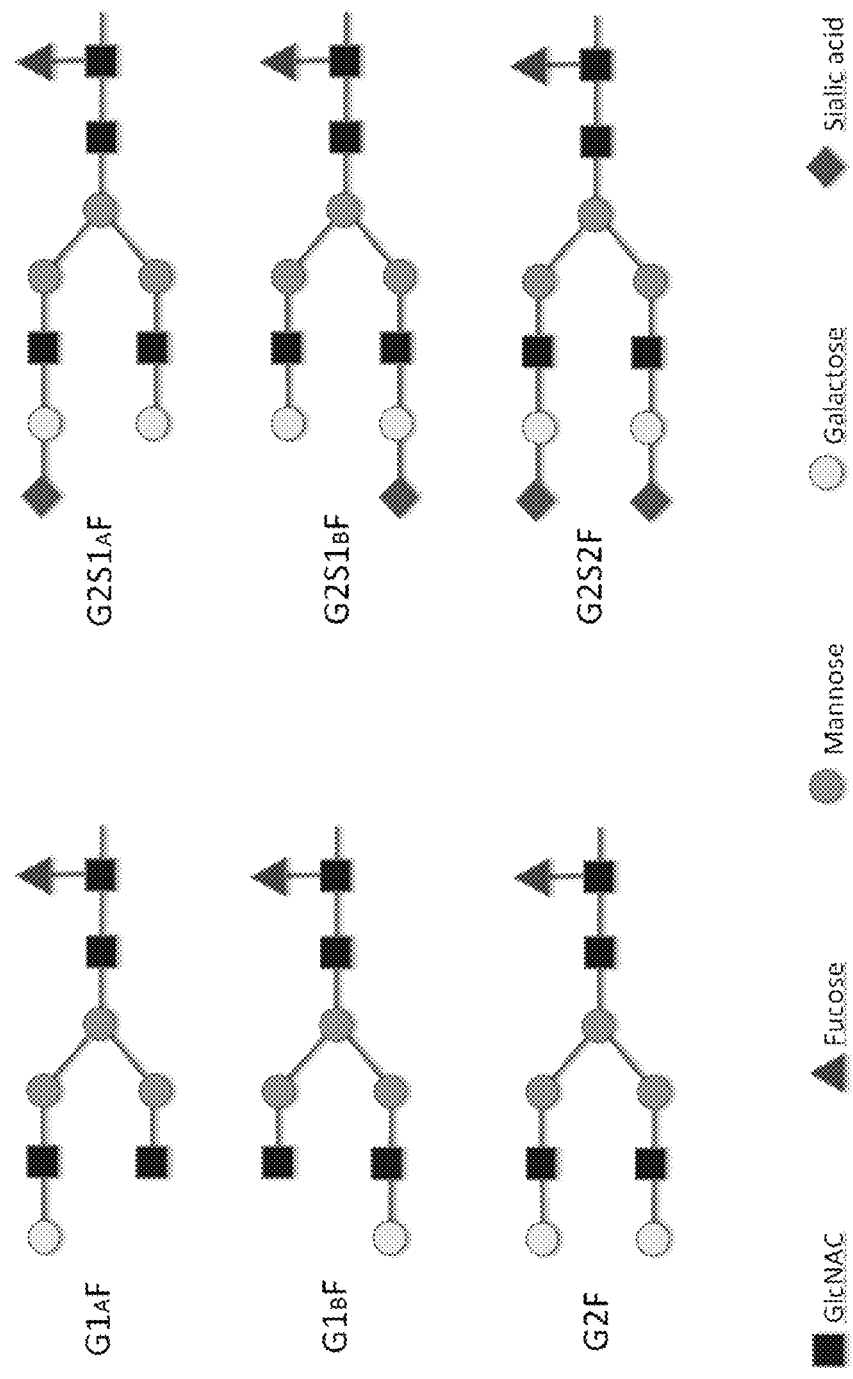
FIG. 1D is a schematic depicting exemplary galactosylated glycans imparting non-immunogenic properties to biologics.

As used herein the terms "G0 glycoform," "G1 glycoform," and "G2 glycoform" refer to N-Glycan glycoforms that have zero, one or two terminal galactose residues respectively, as depicted in FIGS. 1C and 1D herein. These terms include G0, G1, and G2 glycoforms that are fucosylated (shown as G0F, G1F and G2F respectively in FIGS. 1C and 1D) or comprise a bisecting N-acetylglucosamine residue.

In certain embodiments, the G1 and G2 glycoforms further comprise sialic acid residues linked to one or both of the terminal galactose residues to form G1S1, G2S1 and G2S2 glycoforms. As used herein the terms "G1S1 glycoform," "G2S1 glycoform," and "G2S2 glycoform" refer to N-Glycan glycoforms that have a sialic acid residue linked to the sole terminal galactose residue in a G1 glycoform, one of the terminal galactose residue in a G2 glycoform, or both of the terminal galactose residue in a G2 glycoform, respectively (see FIG. 1D herein). These terms include G1S1, G2S1 and G2S2 glycoforms that are fucosylated or comprise a bisecting N-acetylglucosamine residue. In certain embodiments, the sialic residues of G1S1, G2S1 and G2S2 glycoforms are linked by alpha-2,6-sialic acid linkages to the terminal galactose residue of each glycoform in order to enhance the anti-inflammatory activity of the binding molecule (see e.g., Anthony et al., PNAS 105: 19571-19578, 2008).

As used herein the terms "G1F glycoform," "G2F glycoform," "G1S1F glycoform," "G2S1F glycoform," and "G2S2F glycoform" refer to "G1 glycoform," and "G2 glycoform" "G1S1 glycoform," "G2S1 glycoform," and "G2S2 glycoform" that are fucosylated.

As used herein, the term"M3-M9 glycoforms" refers to the mannosylated glycoforms depicted in FIG. 1C.

As used herein, the term "G/M ratio" or "Gtotal:M ratio" refers to the ratio of the total percent amount of all galactose containing glycoforms in a population of Fc-domain containing binding proteins relative to the total percent amount of oligomannose (e.g., M3-M9) glycoforms.

As used herein, the term"G1/2:M ratio" refers to the ratio of the total percent amount of G1 and G2 glycoforms in a population of Fc-domain containing binding proteins relative to the total percent amount of M3-M8 glycoforms.

As used herein, the term "GS:M ratio" refers to the ratio of the total percent amount G1S1, G2S1 and G2S2 glycoforms in a population of Fc-domain containing binding proteins relative to the total percent amount of M3-M9 glycoforms.

As used herein the term "reference binding composition" or "reference antibody" refers to a binding composition having the substantially the same amino acid sequence as (e.g., having about 90-100% identical amino acid sequence) of a glycoengineered antibody composition of the invention disclosed herein, e.g., a binding composition to which it is compared. In some embodiments, the reference composition is a FDA approved therapeutic Fc-domain containing binding protein (e.g., antibody) or a biosimilar thereof. In other embodiments, the reference binding composition comprises a non-hypergalactosylated population of Fc-domain containing binding proteins.

As used herein the term "non-hypergalactosylated population" refers a population of Fc domain-containing binding proteins in which the amount of G1 and/or G2 glycoforms are not enriched relative to the G0 glycoforms, as compared to a reference population of Fc domain-containing binding proteins having the same amino acid sequence.

As used herein, the term "more than" means more than or equal to, and the term "less than" means less than or equal to.

As used herein, the term "infliximab" refers to the anti-TNF antibody marketed as REMICADE™, having Chemical Abstracts Service (CAS) designation 170277-31-3.

As used herein, the term "golimumab" refers to the anti-TNF antibody marketed as SIMPONI™, having Chemical Abstracts Service (CAS) designation 476181-74-5.

As used herein, the term "adalimumab" refers to the anti-TNF antibody marketed as HUMIRA™, having Chemical Abstracts Service (CAS) designation 331731-18-1.

As used herein, the term "infliximab" refers to the anti-TNF immunoadhesin marketed as ENBREL™, having Chemical Abstracts Service (CAS) designation 1094-08-2.

The term "human TNF-alpha", as used herein, is intended to refer to a human cytokine that exists as a 17 kD secreted form and a 26 kD membrane associated form, the biologically active form of which is composed of a trimer of noncovalently bound 17 kD molecules. The structure of human TNF-alpha is described further in, for example, Pennica, D., et al. (1984) Nature 312:724-729; Davis, J. M., et al. (1987) Biochemistry 26:1322-1326; and Jones, E. Y., et al. (1989) Nature 338:225-228. The term human TNF-alpha is intended to include recombinant human TNF-alpha, which can be prepared by standard recombinant expression methods or purchased commercially (R & D Systems, Catalog No. 210-TA, Minneapolis, Minn.).

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "Fc domain" is used to define the C-terminal region of an immunoglobulin heavy chain, which may be generated by papain digestion of an intact antibody. The Fc domain may be a native sequence Fc domain or a variant Fc domain. The Fc domain of an immunoglobulin generally comprises two constant domains, a CH2 domain and a CH3 domain, and optionally comprises a CH4 domain. Replacements of amino acid residues in the Fc portion to alter antibody effector function are known in the art (Winter, et al. U.S. Pat. Nos. 5,648,260; 5,624,821). The Fc domain of an antibody mediates several important effector functions e.g.

cytokine induction, ADCC, phagocytosis, complement dependent cytotoxicity (CDC) and half-life/clearance rate of antibody and antigen-antibody complexes. In certain embodiments, at least one amino acid residue is altered (e.g., deleted, inserted, or replaced) in the Fc domain of an Fc domain-containing binding protein such that effector functions of the binding protein are altered.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) an Fab fragment, a monovalent fragment consisting of the VL, VH, CL and CH1 domains; (ii) an F(ab').sub.2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5). In addition single chain antibodies also include "linear antibodies" comprising a pair of tandem Fv segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

As used herein, the terms "VH domain" and "VL domain" refer to single antibody variable heavy and light domains, respectively, comprising FR (Framework Regions) 1, 2, 3 and 4 and CDR (Complementary Determinant Regions) 1, 2 and 3 (see Kabat et al. (1991) Sequences of Proteins of Immunological Interest. (NIH Publication No. 91-3242, Bethesda).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat, based on sequence comparisons.

As used herein the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat definition of CDRs).

As used herein, the term "specifically binds to" refers to the ability of a binding protein to bind to an antigen with an $K_d$ of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or more, and/or bind to an antigen with an affinity that is at least two-fold greater than its affinity for a nonspecific antigen. It shall be understood, however, that the binding protein are capable of specifically binding to two or more antigens which are related in sequence. For example, the binding polypeptides of the invention can specifically bind to both human and a non-human (e.g., mouse or non-human primate) orthologs of an antigen.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

"Pharmacokinetics" refers to the process by which a drug is absorbed, distributed, metabolized, and excreted by an organism. The pharmacokinetic (PK) profile of Fc containing binding proteins can be easily determined in rodents using methods known to one skilled in the art (U.S. Published Patent Application No. 2009/0311253).

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae*. In certain embodiments, the host cell is an engineered CHO cell, e.g., a CHO cell transformed with a heterologous galactosyltransferase and/or a heterologous sialyltransferase.

II. Glycoengineered Binding Protein Compositions

In certain aspects, the invention provides a composition comprising a population of Fc-domain containing binding proteins that are hypergalactosylated and/or hypomannosylated. In certain embodiments, the population of Fc domain-containing binding proteins employed in the compositions and methods disclosed herein has an increased amount of G1 and/or G2 glycoforms relative to the G0 glycoforms, as compared to a reference population comprising a reference Fc domain-containing binding protein with the same amino acid sequence. In certain embodiments, all of the Fc-domain binding polypeptides in the population may be directed to the same antigen or epitope. In other embodiments, all of the Fc-domain binding polypeptides in the population are encoded by the same nucleic acid sequence.

In certain embodiments, the population of Fc domain-containing binding proteins comprises less than 70%, less than 69%, less than 68%, less than 67%, less than 66%, less than 65%, less than 64%, less than 63%, less than 62%, less than 61%, less than 60%, less than 59%, less than 58%, less than 57%, less than 56%, less than 55%, less than 54%, less than 53%, less than 52%, less than 51%, less than 50%, less than 49%, less than 48%, less than 47%, less than 46%, less than 45%, less than 44%, less than 43%, less than 42%, less than 41%, less than 40%, less than 39%, less than 38%, less than 37%, less than 36%, less than 35%, less than 34%, less than 33%, less than 32%, less than 31%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the G0 glycoforms.

In one embodiment, the population of Fc domain-containing binding proteins comprises 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the G0 glycoform.

In one embodiment, the population of Fc domain-containing binding proteins comprises more than 20%, more than 21%, more than 22%, more than 23%, more than 24%, more than 25%, more than 26%, more than 27%, more than 28%, more than 29%, more than 30%, more than 31%, more than 32%, more than 33%, more than 34%, more than 35%, more than 36%, more than 37%, more than 38%, more than 39%, more than 40%, more than 41%, more than 42%, more than 43%, more than 44%, more than 45%, more than 46%, more than 47%, more than 48%, more than 49%, more than 50%, more than 51%, more than 52%, more than 53%, more than 54%, more than 55%, more than 56%, more than 57%, more than 58%, more than 59%, more than 60, 61%, more than 62%, more than 63%, more than 64%, more than 65%, more than 66%, more than 67%, more than 68%, more than 69%, more than 70%, more than 71%, more than 72%, more than 73%, more than 74%, more than 75%, more than 76%, more than 77%, more than 78%, more than 79%, more than 80%, more than 81%, more than 82%, more than 83%, more than 84%, more than 85%, more than 86%, more than 87%, more than 88%, more than 89%, more than 90%, more than 91%, more than 92%, more than 93%, more than 94%, more than 95%, more than 96%, more than 97%, more than 98%, or more than 99% of the G1 glycoforms. In certain embodiments, the G1 glycoforms in the hypergalactosylated population are G1F glycoforms.

In one embodiment, the population of Fc domain-containing binding proteins comprises 20%, 21%, 22%, 23%, 24%, 25%, 26%, 27%, 28%, 29%, 30, 31%, 32%, 33%, 34%, 35%, 36%, 37%, 38%, 39%, 40, 41%, 42%, 43%, 44%, 45%, 46%, 47%, 48%, 49%, 50, 51%, 52%, 53%, 54%, 55%, 56%, 57%, 58%, 59%, 60%, 61%, 62%, 63%, 64%, 65%, 66%, 67%, 68%, 69%, 70, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the G1 glycoform. In certain embodiments, the G1 glycoforms in the hypergalactosylated population are G1F glycoforms.

In one embodiment, the population of Fc domain-containing binding proteins comprises more than 20%, more than 21%, more than 22%, more than 23%, more than 24%, more than 25%, more than 26%, more than 27%, more than 28%, more than 29%, more than 30%, more than 31%, more than 32%, more than 33%, more than 34%, more than 35%, more than 36%, more than 37%, more than 38%, more than 39%, more than 40%, more than 41%, more than 42%, more than 43%, more than 44%, more than 45%, more than 46%, more than 47%, more than 48%, more than 49%, more than 50%, more than 51%, more than 52%, more than 53%, more than 54%, more than 55%, more than 56%, more than 57%, more than 58%, more than 59%, more than 60%, more than 61%, more than 62%, more than 63%, more than 64%, more than 65%, more than 66%, more than 67%, more than 68%, more than 69%, more than 70%, more than 71%, more than 72%, more than 73%, more than 74%, more than 75%, more than 76%, more than 77%, more than 78%, more than 79%, more than 80%, more than 81%, more than 82%, more than 83%, more than 84%, more than 85%, more than 86%, more than 87%, more than 88%, more than 89%, more than 90%, more than 91%, more than 92%, more than 93%, more than 94%, more than 95%, more than 96%, more than 97%, more than 98%, or more than 99% of the G2 glycoforms. In certain embodiments, the G2 glycoforms in the hypergalactosylated population are G2F glycoforms.

In certain embodiments, the population of Fc domain-containing binding proteins comprises 20%, 21%, 22%, 23%, 24%, 25%, 26%, 27%, 28%, 29%, 30, 31%, 32%, 33%, 34%, 35%, 36%, 37%, 38%, 39%, 40, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the G2 glycoform. In certain embodiments, the G2 glycoforms in the hypergalactosylated population are G2F glycoforms.

In certain embodiments, the total percent amount of G1 and G2 glycoforms in the population of Fc domain-containing binding proteins is between 20% and 99%, between 21% and 99%, between 22% and 99%, between 23% and 99%, between 24% and 99%, between 25% and 99%, between 26% and 99%, between 27% and 99%, between 28% and 99%, between 29% and 99%, between 30% and 99%, between 31% and 99%, between 32% and 99%, between 33% and 99%, between 34% and 99%, between 35% and 99%, between 36% and 99%, between 37% and 99%, between 38% and 99%, between 39% and 99%, between 40, 41% and 99%, between 42% and 99%, between 43% and 99%, between 44% and 99%, between 45% and 99%, between 46% and 99%, between 47% and 99%, between 48% and 99%, between 49% and 99%, between 50% and 99%, between 51% and 99%, between 52% and 99%, between 53% and 99%, between 54% and 99%, between 55% and 99%, between 56% and 99%, between 57% and 99%, between 58% and 99%, between 59% and 99%, between 60% and 99%, between 61% and 99%, between 62% and 99%, between 63% and 99%, between 64% and 99%, between 65% and 99%, between 66% and 99%, between 67% and 99%, between 68% and 99%, between 69% and 99%, between 70% and 99%, between 71% and 99%, between 72% and 99%, between 73% and 99%, between 74% and 99%, between 75% and 99%, between 76% and 99%, between 77% and 99%, between 78% and 99%, between 79% and 99%, between 80% and 99%, between 81% and 99%, between 82% and 99%, between 83% and 99%, between 84% and 99%, between 85% and 99%, between 86% and 99%, between 87% and 99%, between 88% and 99%, between 89% and 99%, between 90% and 99%, between 91% and 99%, between 92% and 99%, between 93% and 99%, between 94% and 99%, between 95% and 99%, between 96% and 99%, between 97% and 99%, or between 98% and 99%. In certain embodiments, the G1 and G2 glycoforms in the population are G1F and G2F glycoforms.

In certain embodiments, the total percent amount of G1 and G2 glycoforms in the population of Fc domain-containing binding proteins is between 20% and 99%, between 20% and 98%, between 20% and 97%, between 20% and 96%, between 20% and 95%, between 20% and 94%, between 20% and 93%, between 20% and 92%, between 20% and 91%, between 20% and 90%, between 20% and 89%, between 20% and 88%, between 20% and 87%, between 20% and 86%, between 20% and 85%, between 20% and 84%, between 20% and 83%, between 20% and 82%, between 20% and 81%, between 20% and 80%, between 20% and 79%, between 20% and 78%, between 20% and 77%, between 20% and 76%, between 20% and 75%, between 20% and 74%, between 20% and 73%, between 20% and 72%, between 20% and 71%, between 20% and 70%, between 20% and 69%, between 20% and 68%, between 20% and 67%, between 20% and 66%, between 20% and 65%, between 20% and 64%, between 20% and 63%, between 20% and 62%, between 20% and 61%, between 20% and 60%, between 20% and 59%, between 20% and 58%, between 20% and 57%, between 20% and 56%, between 20% and 55%, between 20% and 54%, between 20% and 53%, between 20% and 52%, between 20% and 51%, between 20% and 50%, between 20% and 49%, between 20% and 48%, between 20% and 47%, between 20% and 46%, between 20% and 45%, between 20% and 44%, between 20% and 43%, between 20% and 42%, between 20% and 41%, between 20% and 40%, between 20% and 39%, between 20% and 38%, between 20% and 37%, between 20% and 36%, between 20% and 35%, between 20% and 34%, between 20% and 33%, between 20% and 32%, between 20% and 31%, between 20% and 30%, between 20% and 29%, between 20% and 28%, between 20% and 27%, between 20% and 26%, between 20% and 25%, between 20% and 24%, between 20% and 23%, between 20% and 22%, or between 20% and 21%. In certain embodiments, the G1 and G2 glycoforms in the population are G1F and G2F glycoforms.

In certain embodiments, the population of Fc domain-containing binding proteins employed in the compositions and methods disclosed herein has an increased amount of G1S1, G2S1 and G2S2 glycoforms relative to the G0 glycoforms, as compared to a reference population comprising a reference Fc domain-containing binding protein with the same amino acid sequence.

In one embodiment, the population of Fc domain-containing binding proteins comprises more than 20%, more than 21%, more than 22%, more than 23%, more than 24%, more than 25%, more than 26%, more than 27%, more than 28%, more than 29%, more than 30%, more than 31%, more than 32%, more than 33%, more than 34%, more than 35%, more than 36%, more than 37%, more than 38%, more than 39%, more than 40%, more than 41%, more than 42%, more than 43%, more than 44%, more than 45%, more than 46%, more than 47%, more than 48%, more than 49%, more than 50%, more than 51%, more than 52%, more than 53%, more than 54%, more than 55%, more than 56%, more than 57%, more than 58%, more than 59%, more than 60, 61%, more than 62%, more than 63%, more than 64%, more than 65%, more than 66%, more than 67%, more than 68%, more than 69%, more than 70%, more than 71%, more than 72%, more than 73%, more than 74%, more than 75%, more than 76%, more than 77%, more than 78%, more than 79%, more than 80%, more than 81%, more than 82%, more than 83%, more than 84%, more than 85%, more than 86%, more than 87%, more than 88%, more than 89%, more than 90%, more than 91%, more than 92%, more than 93%, more than 94%, more than 95%, more than 96%, more than 97%, more than 98%, or more than 99% of the G1S1 glycoforms. In certain embodiments, the G1S1 glycoforms in the population are G1S1F glycoforms.

In one embodiment, the population of Fc domain-containing binding proteins comprises 20%, 21%, 22%, 23%, 24%, 25%, 26%, 27%, 28%, 29%, 30, 31%, 32%, 33%, 34%, 35%, 36%, 37%, 38%, 39%, 40, 41%, 42%, 43%, 44%, 45%, 46%, 47%, 48%, 49%, 50, 51%, 52%, 53%, 54%, 55%, 56%, 57%, 58%, 59%, 60%, 61%, 62%, 63%, 64%, 65%, 66%, 67%, 68%, 69%, 70, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the G1S1 glycoform. In certain embodiments, the G1S1 glycoforms in the population are G1S1F glycoforms.

In one embodiment, the population of Fc domain-containing binding proteins comprises more than 20%, more than 21%, more than 22%, more than 23%, more than 24%, more than 25%, more than 26%, more than 27%, more than 28%, more than 29%, more than 30%, more than 31%, more than 32%, more than 33%, more than 34%, more than 35%, more than 36%, more than 37%, more than 38%, more than 39%, more than 40%, more than 41%, more than 42%, more than 43%, more than 44%, more than 45%, more than 46%, more than 47%, more than 48%, more than 49%, more than 50%, more than 51%, more than 52%, more than 53%, more than 54%, more than 55%, more than 56%, more than 57%, more than 58%, more than 59%, more than 60, 61%, more than 62%, more than 63%, more than 64%, more than 65%, more than 66%, more than 67%, more than 68%, more than 69%, more than 70%, more than 71%, more than 72%, more than 73%, more than 74%, more than 75%, more than 76%, more than 77%, more than 78%, more than 79%, more than 80%, more than 81%, more than 82%, more than 83%, more than 84%, more than 85%, more than 86%, more than 87%, more than 88%, more than 89%, more than 90%, more than 91%, more than 92%, more than 93%, more than 94%, more than 95%, more than 96%, more than 97%, more than 98%, or more than 99% of the G2S1 glycoforms. In certain embodiments, the G2S1 glycoforms in the hypergalactosylated population are G2S1F glycoforms.

In one embodiment, the population of Fc domain-containing binding proteins comprises 20%, 21%, 22%, 23%, 24%, 25%, 26%, 27%, 28%, 29%, 30, 31%, 32%, 33%, 34%, 35%, 36%, 37%, 38%, 39%, 40, 41%, 42%, 43%, 44%, 45%, 46%, 47%, 48%, 49%, 50, 51%, 52%, 53%, 54%, 55%, 56%, 57%, 58%, 59%, 60%, 61%, 62%, 63%, 64%, 65%, 66%, 67%, 68%, 69%, 70, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the G2S1 glycoform. In certain embodiments, the G2S1 glycoforms in the population are G2S1F glycoforms.

In one embodiment, the population of Fc domain-containing binding proteins comprises more than 20%, more than 21%, more than 22%, more than 23%, more than 24%, more than 25%, more than 26%, more than 27%, more than 28%, more than 29%, more than 30%, more than 31%, more than 32%, more than 33%, more than 34%, more than 35%, more than 36%, more than 37%, more than 38%, more than 39%, more than 40%, more than 41%, more than 42%, more than 43%, more than 44%, more than 45%, more than 46%, more than 47%, more than 48%, more than 49%, more than 50%, more than 51%, more than 52%, more than 53%, more than 54%, more than 55%, more than 56%, more than 57%, more than 58%, more than 59%, more than 60, 61%, more than 62%, more than 63%, more than 64%, more than 65%, more than 66%, more than 67%, more than 68%, more than 69%, more than 70%, more than 71%, more than 72%, more than 73%, more than 74%, more than 75%, more than 76%, more than 77%, more than 78%, more than 79%, more than 80%, more than 81%, more than 82%, more than 83%, more than 84%, more than 85%, more than 86%, more than 87%, more than 88%, more than 89%, more than 90%, more than 91%, more than 92%, more than 93%, more than 94%, more than 95%, more than 96%, more than 97%, more than 98%, or more than 99% of the G2S2 glycoforms. In certain embodiments, the G2S2 glycoforms in the population are G2S2F glycoforms.

In one embodiment, the population of Fc domain-containing binding proteins comprises 20%, 21%, 22%, 23%, 24%, 25%, 26%, 27%, 28%, 29%, 30, 31%, 32%, 33%, 34%, 35%, 36%, 37%, 38%, 39%, 40, 41%, 42%, 43%, 44%, 45%, 46%, 47%, 48%, 49%, 50, 51%, 52%, 53%, 54%, 55%, 56%, 57%, 58%, 59%, 60%, 61%, 62%, 63%, 64%, 65%, 66%, 67%, 68%, 69%, 70, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the G2S2 glycoform. In certain embodiments, the G2S2 glycoforms in the population are G2S2F glycoforms.

In certain embodiments, the total percent amount of G1S1, G2S1 and G2S2 glycoforms in the population of Fc domain-containing binding proteins is between 20% and 99%, between 21% and 99%, between 22% and 99%, between 23% and 99%, between 24% and 99%, between 25% and 99%, between 26% and 99%, between 27% and 99%, between 28% and 99%, between 29% and 99%, between 30% and 99%, between 31% and 99%, between 32% and 99%, between 33% and 99%, between 34% and 99%, between 35% and 99%, between 36% and 99%, between 37% and 99%, between 38% and 99%, between 39% and 99%, between 40, 41% and 99%, between 42% and 99%, between 43% and 99%, between 44% and 99%, between 45% and 99%, between 46% and 99%, between 47% and 99%, between 48% and 99%, between 49% and 99%, between 50% and 99%, between 51% and 99%, between 52% and 99%, between 53% and 99%, between 54% and 99%, between 55% and 99%, between 56% and 99%, between 57% and 99%, between 58% and 99%, between 59% and 99%, between 60% and 99%, between 61% and 99%, between 62% and 99%, between 63% and 99%, between 64% and 99%, between 65% and 99%, between 66% and 99%, between 67% and 99%, between 68% and 99%, between 69% and 99%, between 70% and 99%, between 71% and 99%, between 72% and 99%, between 73% and 99%, between 74% and 99%, between 75% and 99%, between 76% and 99%, between 77% and 99%, between 78% and 99%, between 79% and 99%, between 80% and 99%, between 81% and 99%, between 82% and 99%, between 83% and 99%, between 84% and 99%, between 85% and 99%, between 86% and 99%, between 87% and 99%, between 88% and 99%, between 89% and 99%, between 90% and 99%, between 91% and 99%, between 92% and 99%, between 93% and 99%, between 94% and 99%, between 95% and 99%, between 96% and 99%, between 97% and 99%, or between 98% and 99%. In certain embodiments, the G1S1, G2S1 and G2S2 glycoforms in the population are G1S1F, G2S1F and G2S2F glycoforms.

In certain embodiments, the total percent amount of G1S1, G2S1 and G2S2 glycoforms in the population of Fc domain-containing binding proteins is between 20% and 99%, between 20% and 98%, between 20% and 97%, between 20% and 96%, between 20% and 95%, between 20% and 94%, between 20% and 93%, between 20% and 92%, between 20% and 91%, between 20% and 90%, between 20% and 89%, between 20% and 88%, between 20% and 87%, between 20% and 86%, between 20% and 85%, between 20% and 84%, between 20% and 83%, between 20% and 82%, between 20% and 81%, between 20% and 80%, between 20% and 79%, between 20% and 78%, between 20% and 77%, between 20% and 76%, between 20% and 75%, between 20% and 74%, between 20% and 73%, between 20% and 72%, between 20% and 71%, between 20% and 70%, between 20% and 69%, between 20% and 68%, between 20% and 67%, between 20% and 66%, between 20% and 65%, between 20% and 64%, between 20% and 63%, between 20% and 62%, between 20% and 61%, between 20% and 60%, between 20% and 59%, between 20% and 58%, between 20% and 57%, between 20% and 56%, between 20% and 55%, between 20% and 54%, between 20% and 53%, between 20% and 52%, between 20% and 51%, between 20% and 50%, between 20% and 49%, between 20% and 48%, between 20% and 47%, between 20% and 46%, between 20% and 45%, between 20% and 44%, between 20% and 43%, between 20% and 42%, between 20% and 41%, between 20% and 40%, between 20% and 39%, between 20% and 38%, between 20% and 37%, between 20% and 36%, between 20% and 35%, between 20% and 34%, between 20% and 33%, between 20% and 32%, between 20% and 31%, between 20% and 30%, between 20% and 29%, between 20% and 28%, between 20% and 27%, between 20% and 26%, between 20% and 25%, between 20% and 24%, between 20% and 23%, between 20% and 22%, or between 20% and 21% of the G1S1, G1S2 and G2S2 glycoforms. In certain embodiments, the G1S1, G2S1 and G2S2 glycoforms in the population are G1S1F, G2S1F and G2S2F glycoforms.

In certain embodiments, the total percent amount of G1, G2, G1S1, G2S1 and G2S2 glycoforms in the population of Fc domain-containing binding proteins is between 20% and 99%, between 21% and 99%, between 22% and 99%, between 23% and 99%, between 24% and 99%, between 25% and 99%, between 26% and 99%, between 27% and 99%, between 28% and 99%, between 29% and 99%, between 30% and 99%, between 31% and 99%, between 32% and 99%, between 33% and 99%, between 34% and 99%, between 35% and 99%, between 36% and 99%, between 37% and 99%, between 38% and 99%, between 39% and 99%, between 40, 41% and 99%, between 42% and 99%, between 43% and 99%, between 44% and 99%, between 45% and 99%, between 46% and 99%, between 47% and 99%, between 48% and 99%, between 49% and 99%, between 50% and 99%, between 51% and 99%, between 52% and 99%, between 53% and 99%, between 54% and 99%, between 55% and 99%, between 56% and 99%, between 57% and 99%, between 58% and 99%, between 59% and 99%, between 60% and 99%, between 61% and 99%, between 62% and 99%, between 63% and 99%, between 64% and 99%, between 65% and 99%, between 66% and 99%, between 67% and 99%, between 68% and 99%, between 69% and 99%, between 70% and 99%, between 71% and 99%, between 72% and 99%, between 73% and 99%, between 74% and 99%, between 75% and 99%, between 76% and 99%, between 77% and 99%, between 78% and 99%, between 79% and 99%, between 80% and 99%, between 81% and 99%, between 82% and 99%, between 83% and 99%, between 84% and 99%, between 85% and 99%, between 86% and 99%, between 87% and 99%, between 88% and 99%, between 89% and 99%, between 90% and 99%, between 91% and 99%, between 92% and 99%, between 93% and 99%, between 94% and 99%, between 95% and 99%, between 96% and 99%, between 97% and 99%, or between 98% and 99%. In certain embodiments, the G1, G2, G1S1, G2S1 and G2S2 glycoforms in the population are G1F, G2F, G1S1F, G2S1F and G2S2F glycoforms.

In certain embodiments, the total percent amount of G1, G2, G1S1, G2S1 and G2S2 glycoforms in the population of Fc domain-containing binding proteins is between 20% and 99%, between 20% and 98%, between 20% and 97%, between 20% and 96%, between 20% and 95%, between 20% and 94%, between 20% and 93%, between 20% and 92%, between 20% and 91%, between 20% and 90%, between 20% and 89%, between 20% and 88%, between 20% and 87%, between 20% and 86%, between 20% and 85%, between 20% and 84%, between 20% and 83%, between 20% and 82%, between 20% and 81%, between 20% and 80%, between 20% and 79%, between 20% and 78%, between 20% and 77%, between 20% and 76%, between 20% and 75%, between 20% and 74%, between 20% and 73%, between 20% and 72%, between 20% and 71%, between 20% and 70%, between 20% and 69%, between 20% and 68%, between 20% and 67%, between 20% and 66%, between 20% and 65%, between 20% and 64%, between 20% and 63%, between 20% and 62%, between 20% and 61%, between 20% and 60%, between 20% and 59%, between 20% and 58%, between 20% and 57%, between 20% and 56%, between 20% and 55%, between 20% and 54%, between 20% and 53%, between 20% and 52%, between 20% and 51%, between 20% and 50%, between 20% and 49%, between 20% and 48%, between 20% and 47%, between 20% and 46%, between 20% and 45%, between 20% and 44%, between 20% and 43%, between 20% and 42%, between 20% and 41%, between 20% and 40%, between 20% and 39%, between 20% and 38%, between 20% and 37%, between 20% and 36%, between 20% and 35%, between 20% and 34%, between 20% and 33%, between 20% and 32%, between 20% and 31%, between 20% and 30%, between 20% and 29%, between 20% and 28%, between 20% and 27%, between 20% and 26%, between 20% and 25%, between 20% and 24%, between 20% and 23%, between 20% and 22%, or between 20% and 21% of the G1S1, G1S2 and G2S2 glycoforms. In certain embodiments, the G1, G2, G1S1, G2S1 and G2S2 glycoforms in the hypergalactosylated population are G1F, G2F, G1S1F, G2S1F and G2S2F glycoforms.

In one embodiment, the sialylated glycoforms (e.g., G1S1, G2S1 and G2S2 glycoforms) in the population of Fc domain-containing binding proteins have increased levels of terminal alpha 2,6-sialic acid linkages on their Fc glycans. In certain embodiments, more than 20%, more than 21%, more than 22%, more than 23%, more than 24%, more than 25%, more than 26%, more than 27%, more than 28%, more than 29%, more than 30%, more than 31%, more than 32%, more than 33%, more than 34%, more than 35%, more than 36%, more than 37%, more than 38%, more than 39%, more than 40%, more than 41%, more than 42%, more than 43%, more than 44%, more than 45%, more than 46%, more than 47%, more than 48%, more than 49%, more than 50%, more than 51%, more than 52%, more than 53%, more than 54%, more than 55%, more than 56%, more than 57%, more than 58%, more than 59%, more than 60, 61%, more than 62%, more than 63%, more than 64%, more than 65%, more than 66%, more than 67%, more than 68%, more than 69%, more than 70%, more than 71%, more than 72%, more than 73%, more than 74%, more than 75%, more than 76%, more than 77%, more than 78%, more than 79%, more than 80%, more than 81%, more than 82%, more than 83%, more than 84%, more than 85%, more than 86%, more than 87%, more than 88%, more than 89%, more than 90%, more than 91%, more than 92%, more than 93%, more than 94%, more than 95%, more than 96%, more than 97%, more than 98%, or more than 99% of the sialylated glycoforms contain alpha 2,6-linkages.

In certain embodiments, the G1, G2, G1S1, G2S1 and G2S2 glycoforms in the hypergalactosylated population are G1F, G2F, G1S1F, G2S1F and G2S2F glycoforms.

In certain embodiments, the compositions of the invention are obtained from host cells (e.g., CHO cells or other mammalian host cells) capable of expressing a population of hyperglycosylated and/or hypomannosylated Fc domain-containing binding proteins when grown in culture. In certain embodiments, the composition is obtained from host cells that are genetically engineered for the production of a hyperglycosylated and/or hypomannosylated binding proteins. For example, the host cell (e.g., a CHO cell) may be genetically engineered to overexpress a heterologous galactosyltransferase such as human β1, 4-galactosyltransferase (E.C. 2.4.1.38; Weikert et al., Nature Biotechnology 17, 1116-1121 (1999)) or a mammalian homolog thereof (e.g., mouse galactosyltransferase β1, 4 (Genbank accession number: D00314). Additionally or alternatively, the host cell is a CHO cell having a knock out at least one of the alleles of the beta galactosidase gene (*Cricetulus griseus* Glb1 (Gene ID: 100767446; mRNA sequence: NCBI Reference Sequence: XM_007630176.1; genomic sequence NW_003613697.1 from 2278553 to 2336708). In other embodiments, the binding protein composition is obtained from a host cell that is cultured under conditions such that hypergalactosylated and/or hypomannosylated binding proteins are produced. In some embodiments, the binding protein is expressed in a host cell with one or more sialyltransferase enzymes, e.g., an a2,6 sialyltransferase (e.g., ST6Gal-1).

Exemplary binding protein compositions of the invention may be obtained from cultured mammalian (e.g., CHO) host cells have a "high Gal/low Man" glycoform profile which provides for unexpectedly improved properties (e.g., reduced ADA activity and/or prolonged half-life). Notably, this glycoform profile differs from the highly mannosylated glycoprofile of binding proteins produced in the milk of transgenic animals (see, e.g., US 2014/0296490). Antibody compositions with high oligomannose content are thought to promote the ADA response and/or reduce serum half-life. By contrast, binding protein compositions of the invention exhibit a low degree of terminally mannosylated glycoforms (e.g., M3-M9 glycoforms). For example, in certain embodiments, binding protein compositions of the invention comprise a population of Fc domain-containing binding proteins comprising less than 10%, less than 9%, less than 8%, less than 7%, less than 6%, less than 5%, less than 4%, less than 3%, less than 2% or less than 1% of oligomannose (e.g., M3-M9) glycoforms.

Thus, the compositions of the invention may be characterized as having glycan structures with a G/M ratio (galactose content/mannose content) of greater than 1:1, e.g., greater than 10:1, 50:1 or 99:1. In certain embodiments, the population of Fc domain-containing binding proteins has a G1/2:M ratio of at least 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 80:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, or 1000:1 (e.g., about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 80:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, or 1000:1).

In certain embodiments, the population of Fc domain-containing binding proteins has a GS:M ratio of at least 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 80:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, or 1000:1 (e.g., about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 80:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, or 1000:1).

In certain embodiments, the population of Fc domain-containing binding proteins has a Gtotal:M ratio of at least 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 80:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, or 1000:1 (e.g., about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 80:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, or 1000:1).

Glycoengineered binding compositions of the invention may exhibit improvement in at least one biological activity as compared to a reference binding composition. Biological activity of the preparation can be analyzed by any known method. In some embodiments, a binding activity of the binding composition is improved (e.g., binding to a ligand or receptor). In some embodiments, a therapeutic activity of the glycoengineered binding composition is improved (e.g., an activity in decreasing severity or symptom of a disease or condition, or in delaying appearance of a symptom of a disease or condition). In some embodiments, a pharmacologic activity of the glycoengineered binding composition is improved (e.g., bioavailability, pharmacokinetics, pharmacodynamics). Methods of analyzing bioavailability, pharmacokinetics, and pharmacodynamics of glycoprotein therapeutics are well known in the art.

Glycoengineered binding protein compositions of the invention may exhibit reduced ADA activity and/or enhanced half-life without also exhibiting enhanced complement dependent cytotoxicity (CDC) activity and/or enhanced antibody-dependent cellular cytotoxicity (ADCC) activity. In certain embodiments, the glycoengineered binding protein composition of the invention exhibit reduced ADCC and/or CDC activity relative to a reference binding protein composition comprising the same polypeptide sequence but is not glycoengineered (e.g., hypergalactosylated and/or hypomannosylated) according to the methods of the invention. In one embodiment, the reference binding protein composition is not hypergalactosylated and hypomannosylated. In another embodiment, the reference composition is transgenically produced in mammary gland epithelial cells.

In certain embodiments, the ADCC and/or CDC activity of the glycoengineered composition of the invention is at least 1.1 time lower, at least 1.2 times lower, at least 1.3 times lower, at least 1.4 times lower, at least 1.5 times lower, at least 1.6 times lower, at least 1.7 times lower, at least 1.8 times lower, at least 10 times lower, at least 20 times lower, at least 50 times lower or up to 100 times lower when compared to the reference composition. Methods for determining the level of CDC are known in the art and are often based on determining the amount of cell lysis. Methods for determining the level of ADCC are also known in the art and may be based on evaluating binding to CD16. Commercial kits for determining CDC and/or ADCC activity can be purchased for instance from Genscript (Piscataway, N.J.) and Promega (Madison, Wis.).

In certain embodiments, the compositions of the invention do not induce B-cell depletion. In other embodiments, the hypergalactosylated compositions of the invention exhibit reduced ADA activity and/or enhanced half-life relative to the reference antibody composition. In certain embodiments, the ADA activity of the glycoengineered composition of the invention is at least 1.1 times lower, at least 1.2 times lower, at least 1.3 times lower, at least 1.4 times lower, at least 1.5 times lower, at least 1.6 times lower, at least 1.7 times lower, at least 1.8 times lower, at least 10 times lower, at least 20 times lower, at least 50 times lower or up to 100 times lower when compared to the reference composition. In other embodiments, the serum half-life of the glycoengineered composition of the invention is at least 6 hours, 12 hours, 1 day, 2 days, 3 days, 4 days, 5 days, 6 days, 7 days, 8 days, 9 days, 10 days, 11 days, 12 days, 13 days, 2 weeks, 3 weeks, or 4 weeks longer than the reference composition.

In certain embodiments, the glycoengineered binding protein compositions of the invention exhibit decreased internalization by dendritic cells in a dendritic cell internalization (DCI) assay, as compared to a reference binding protein composition. In an exemplary DCI assay, the glycoengineered binding protein compositions may be fluorescently labelled with a pH-sensitive fluorophore (e.g., pH$^{rodo}$ Red) and combined with dendritic cells and an immunostimulant (e.g., LPS). Internalization of the fluorescently labelled antibodies may be quantified by measuring (e.g., via FACS cell sorting) the fluorescence which occurs upon uptake and exposure of the fluorophore-labelled antibody to the acidic pH in the endosomal compartments of the dendritic cell. Exemplary DCI assays are described in Example 6 herein. Accordingly, in certain embodiments, the glycoengineered binding protein compositions of the invention exhibit at least 10%, at least 20%, at least 30%, at least 40%, at least 50%, at least 60%, at least 70%, at least 80%, at least 90% or at least 100% reduction in fluorescent intensity as compared to a reference antibody composition comprising the same binding polypeptide sequence. In certain embodiments, the glycoengineered binding protein composition is a hypergalactosylated and/or hypomannosylated preparation of adalimumab and the reference binding protein composition is a commercially available or non-glycoengineered preparation of adalimumab (e.g., Humira®). In another embodiment, the reference binding protein composition is a binding protein composition (e.g., an adalimumab composition) obtained from the milk of a transgenic animal.

Quantification of Glycoforms

The glycosylation pattern of the compositions of the invention can be determined by many methods known in the art. For example, methods of analyzing carbohydrates on proteins have been described in U.S. Patent Applications US 2006/0057638 and US 2006/0127950 and: Guile G R, et al. Anal Biochem. 1996 Sep. 5; 240(2):210-26; Packer et al., Glycoconj J. 1998 August; 15(8):737-47; Barb, Biochemistry 48:9705-9707 (2009); Anumula, J. Immunol. Methods 382:167-176 (2012); Gilar et al., Analytical Biochem. 417: 80-88 (2011).

In some instances, glycan structure and composition as described herein are analyzed, for example, by one or more enzymatic methods, chromatographic methods, mass spectrometry (MS) methods, electrophoretic methods, nuclear magnetic resonance (NMR) methods, and combinations thereof. Exemplary enzymatic methods include contacting a composition with one or more enzymes under conditions and for a time sufficient to release one or more glycan(s) (e.g., one or more exposed glycan(s)). In some instances, the one or more enzymes include(s) PNGase F. Exemplary chromatographic methods include, but are not limited to, Strong Anion Exchange chromatography using Pulsed Amperometric Detection (SAX-PAD), Weak Anion Exchange chromatography, liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) methods include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) methods include, but are not limited to, one-dimensional NMR (1 D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof. Additional techniques for the detection, analysis, and/or isolation of particular glycans are described in WO2008/128216; WO2008/128220; WO2008/128218; WO2008/130926; WO2008/128225; WO2008/130924; WO2008/128221; WO2008/128228; WO2008/128227; WO2008/128230; WO2008/128219; WO2008/128222; WO2010/071817; WO2010/071824; WO2010/085251; WO2011/069056; and WO2011/127322, each of which is incorporated herein by reference in its entirety). For example, in some instances, glycans are characterized using one or more of chromatographic methods, electrophoretic methods, nuclear magnetic resonance methods, and combinations thereof.

In exemplary embodiments, the compositions of the invention are analyzed using the art-recognized 2-AB labelling methodology (see U.S. Pat. No. 5,747,347 and Bigge et al., Anal. Biochem., 230: 229-238 (1995) which are incorporated by reference herein in their entireties). 2-AB labelling kits are commercially available (see, e.g., GlycoProfile™ 2-AB Labeling from Sigma Aldrich, St. Louis, Mo.). 2-AB labeling technology employs the fluorophores 2-AB (2-aminobenzamide) or 2-AA (anthranilic acid or 2-aminbenzoic acid) to label the free reducing sugars of a glycoform. Glycans with a free reducing sugar exist in equilibrium between the cyclic (closed ring) and acyclic (open ring) structure. A stable Schiff's base is formed when the carbonyl atom of an acyclic reducing sugar is linked to the amine moiety of the fluorophore in a nucleophilic matter. Following formation of the Schiff's base, the resulting imine group is reduced using sodium cyanoborohydride, resulting in a stable labeled glycan. The 2-AB reagent has an excitation range of 200-450 nm, with an excitation peak at 330 nm, and an emission range of 300-750 nm, with an emission peak at 420 nm.

Prior to labeling, N-glycan samples may be prepared by enzymatic (e.g., PNGase F) or chemical deglycosylation (e.g., hydrazinolysis) of an antibody composition in order to release the N-glycans from the antibodies, and removing any contaminating protein, peptides, salts, detergents, and any additional contaminating substances. Once the N-glycan samples have been labeled, a variety of methods exist to analyze them, including, for example, HPLC, separation by ion exchange chromatography (e.g., high-performance anion exchange), normal phase HPLC, and size exclusion chromatography. Labeled glycans can also be detected using SDS-PAGE and mass spectrometry (e.g., electrospray ionization (ESI) or matrix assisted laser absorption ionization (MALDI-TOF).

Figure 7A:
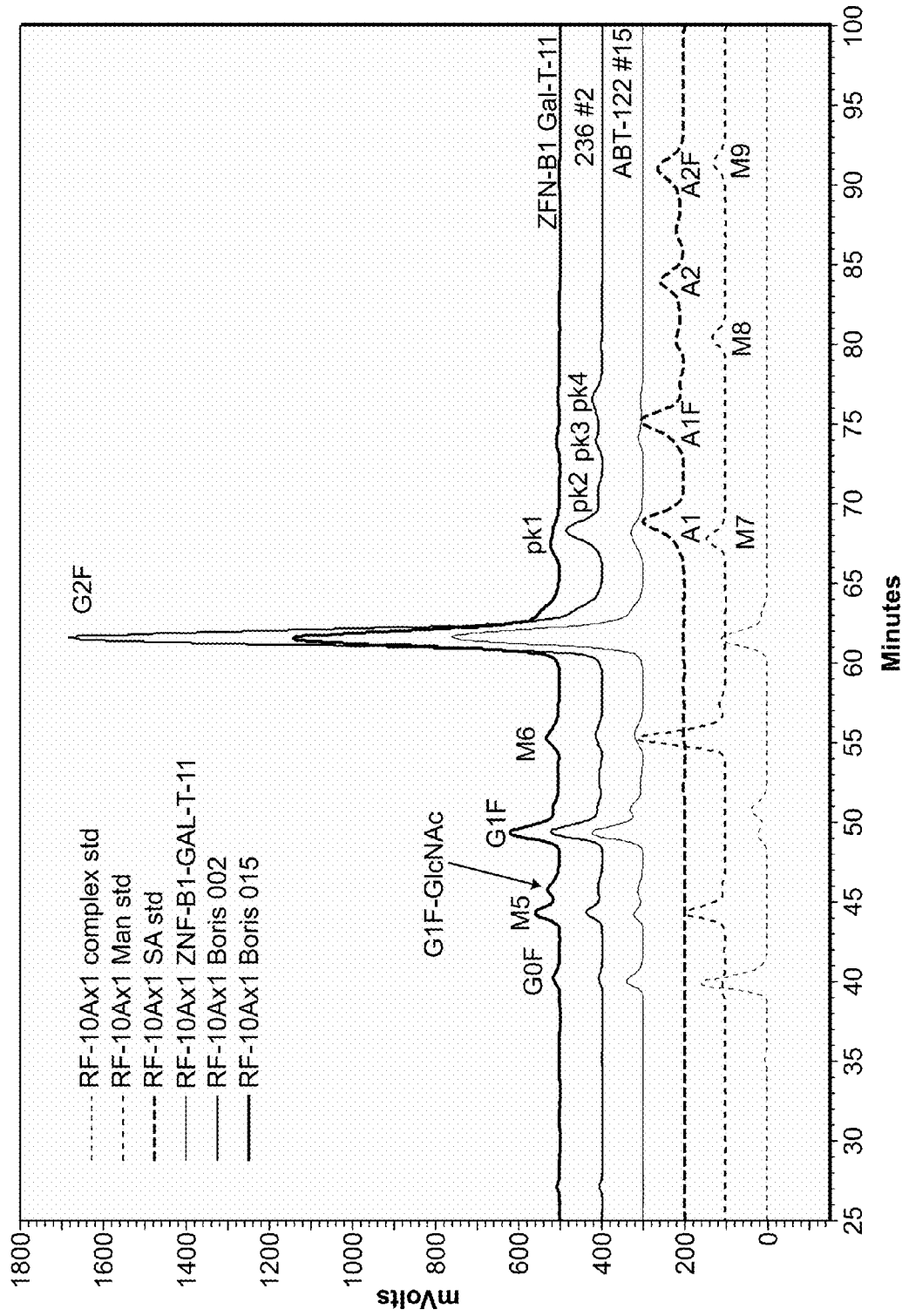
FIG. 7A depicts an exemplary 2-AB HPLC quantitative analysis of glycoengineered binding compositions of the invention. Cell line 236 is a galactosyl transferase transfected CHO cell line producing Adalimumab (D2E7). ZFN-B1 is a CHO cell line producing Adalimumab and containing a knockdown of the Beta galactosidase gene. ABT-122 is an IL17xTNF DVD-Ig.
Figure 7B:
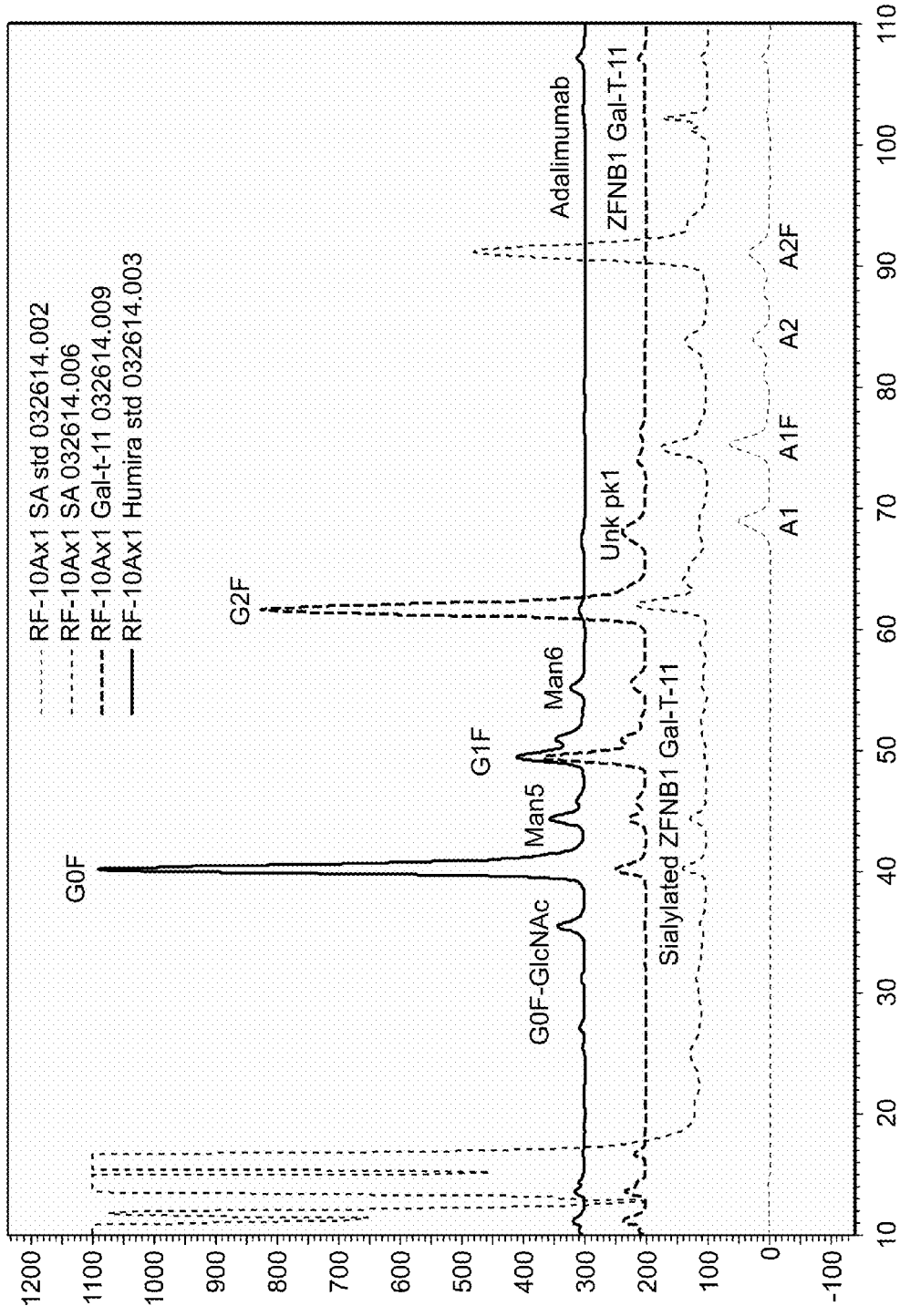
FIG. 7B depicts an exemplary 2-AB HPLC quantitative analysis of the Galtr-11 (pink trace, second from top) and SA-D2E7 (blue trace, second from bottom) glycoengineered binding compositions of the invention as compared to a non-glycoengineered form of adalimumab (Humira®; top trace). The bottom trace corresponds to sialylated glycan standards.

The percent content of each labeled glycoform can be quantified using art-recognized methods. For example, the glycoforms can be quantified based on the N-glycan peaks of a chromatogram, such as a NP HPLC spectrum. Exemplary chromatograms of binding protein composition of the invention are depicted in FIG. 7. Thus, the glycoform profile in a population of Fc-containing binding proteins can be determined by releasing the N-glycans from the binding proteins, resolving the N-glycans on a chromatogram, identifying the N-glycan that corresponds to a specific peak, determining the peak intensity and applying the data to a quantitative formula.

For example, the galactosylation state of a particular binding protein composition can be quantified according to the following formula:

$$\frac{\sum_{i=1}^{n}[\text{number of Gal}]\times(\%\ \text{relative Area})}{\sum_{i=1}^{n}(\text{number of }A)\times(\%\ \text{relative Area})}*100$$

wherein:

n represents the number of analyzed N-glycan peaks of the chromatogram,

"number of Gal" represents the number of Galactose motifs on the antennae of the glycan corresponding to the peak;

"number of A" corresponds to the number of antennae of the glycan form corresponding to the peak; and "% relative Area" corresponds to % of the Area under the corresponding peak.

Similarly, the mannosylation state of a particular binding protein composition can be determined according to the same formula, but where the "number of Gal" is substituted for "number of Man". "Number of Man" represents that number of Mannose motifs on the antennae of the glycan corresponding to the peak.

III. Binding Proteins

In one aspect, the invention provides a population of Fc domain-containing binding proteins (e.g., TNF binding proteins) with a reduced anti-drug immune response.

Any Fc domain-containing binding protein known in the art that comprises an N-Glycan structure is suitable for use in the compositions disclosed herein. In certain embodiments, the binding proteins are therapeutic antibodies or immunoadhesin molecules. In certain embodiments, the binding proteins are FDA approved therapeutic binding proteins. In certain embodiments, the binding proteins are antibodies (e.g., monoclonal antibodies). For example, the binding protein may be selected from the group consisting of alemtuzumab, bevacizumab, cetuximab, edrecolomab, gemtuzumab ozogamicin, ibritumomab tiuxetan, ofatumumab, panitumumab, rituximab, tositumomab, trastuzumab, arcitumomab, capromab pendetide, nofetumomab, satumomab, basiliximab, daclizumab, muromonab-cd3, infliximab, natalizumab, adalimumab, certolizumab, golimumab, infliximab, tocilizumab, omalizumab, abciximab, bevacizumab, ranibzumab, natalizumab, efalizumab, ustekinumab, palivizumab, ruplizumab, denosumab, eculizumab, alefacept, abatacept, etanercept, romiplostim, rilonacept, aflibercept, belatacept, and rilonacept.

In certain embodiments, the Fc domain-containing binding proteins bind to human TNF. Exemplary binding proteins which bind to human TNF include etanercept, infliximab, adalimumab, and golimumab.

In certain exemplary embodiments, the binding protein is the anti-TNF antibody adalimumab or a variant thereof. In certain embodiments, the anti-TNF antibody is an Fc variant of adalimumab (D2E7) comprising the heavy and light chain variable region sequences of adalimumab (see, e.g., U.S. Pat. No. 6,090,382) and a variant Fc region with an amino acid substitution that confers enhanced serum half-life. In certain exemplary embodiments, the variant Fc region is a human IgG1 Fc region comprising the mutations T250Q and M428L relative to a wild-type human IgG1 sequence (wherein amino acid numbering is according to the EU numbering convention as in Kabat). In other embodiments, the anti-TNF antibody is a variant of adalimumab which exhibits pH-sensitive binding to the TNF antigen. PH-sensitive variants may exhibit reduced binding of the TNF-antigen at an acidic pH, thereby promoting release from the endosomal compartment and prolonging serum half-life. For example, pH-sensitive variants comprise histidine mutations within the CDRs of heavy or light chain variable regions of adalimumab. Exemplary pH-sensitive variants of Adalimumab include D2E7SS22.

The heavy chain of D2E7SS22 is provided in SEQ ID NO: 1 (variant Histidine bolded and underlined; C-terminal lysine in parentheses may be present or absent):

EVQLVESGGGLVQPGRSLRLSCAASGFTFDHYAMHWVRQAPGKGLEWVSAI

TWNSGHIDYADSVEGRFTISRDNAKNSLYLQMNSLRAEDTAVYYCAKVSYL

STASSLDYWGQGTLVTVSSASTKGPSVFPLAPSSKSTSGGTAALGCLVKDY

FPEPVTVSWNSGALTSGVHTFPAVLQSSGLYSLSSWTVPSSSLGTQTYICN

VNHKPSNTKVDKKVEPKSCDKTHTCPPCPAPELLGGPSVFLFPPKPKDTLM

ISRTPEVTCVWDVSHEDPEVKFNWYVDGVEVHNAKTKPREEQYNSTYRWSV

LTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLY

SKLTVDKSRWQQGNVFSCSVMHEALHNHYTQKSLSLSPG(K)

The light chain of D2E7SS22 is provided in SEQ ID NO:2 (variant Histidine bolded and underlined):

DIQMTQSPSSLSASVGDRVTITCRASHSIRNYLSWYQQKPGKAPKLLIYAA

STLQSGVPSRFSGSGSGTDFTLTISSLQPEDVATYYCQRYNRAPYTFGQGT

KVEIKRTVAAPSVFIFPPSDEQLKSGTASWCLLNNFYPREAKVQWKVDNAL

QSGNSQESVTEQDSKDSTYSLSSTLTLSKADYEKHKVYACEVTHQGLSSPV

TKSFNRGEC

In another exemplary embodiment, the pH-sensitive variant comprises the heavy and light chain variable regions of D2E7SS22 and a variant Fc region (e.g., a human IgG1 Fc region comprising the mutations T250Q and M428L relative to a wild-type human IgG1 sequence).

In certain embodiments, the binding proteins comprise an antigen binding fragment of an antibody. In exemplary embodiments, the binding protein comprises a single chain variable region sequence (ScFv). Single chain variable region sequences comprise a single polypeptide having one or more antigen binding sites, e.g., a VL domain linked by a flexible linker to a VH domain. ScFv molecules can be constructed in a VH-linker-VL orientation or VL-linker-VH orientation. The flexible hinge that links the VL and VH domains that make up the antigen binding site preferably comprises from about 10 to about 50 amino acid residues. Connecting peptides are known in the art. Binding proteins of the invention may comprise at least one scFv and/or at least one constant region.

In certain embodiments, the binding proteins are multivalent (e.g., tetravalent) antibodies which are produced by fusing a DNA sequence encoding an antibody with a ScFv molecule (e.g., an altered ScFv molecule). For example, in one embodiment, these sequences are combined such that the ScFv molecule (e.g., an altered ScFv molecule) is linked at its N-terminus or C-terminus to an Fc fragment of an antibody via a flexible linker (e.g., a gly/ser linker). In another embodiment a tetravalent antibody of the current disclosure can be made by fusing an ScFv molecule to a connecting peptide, which is fused to a CH1 domain.

In certain embodiments, the binding proteins comprise an altered minibody. Altered minibodies of the current disclosure are dimeric molecules made up of two polypeptide chains each comprising an ScFv molecule (e.g., an altered ScFv molecule comprising an altered VH domain described supra) which is fused to a CH3 domain or portion thereof via a connecting peptide. Minibodies can be made by constructing an ScFv component and connecting peptide-CH3 component using methods described in the art (see, e.g., U.S. Pat. No. 5,837,821 or WO 94/09817A1). In another embodiment, a tetravalent minibody can be constructed. Tetravalent minibodies can be constructed in the same manner as minibodies, except that two ScFv molecules are linked using a flexible linker. The linked scFv-scFv construct is then joined to a CH3 domain.

In certain embodiments, the binding proteins comprise a diabody. Diabodies are dimeric, tetravalent molecules each having a polypeptide similar to scFv molecules, but usually having a short (less than 10 and preferably 1-5) amino acid residue linkers connecting both variable domains, such that the VL and VH domains on the same polypeptide chain cannot interact. Instead, the VL and VH domain of one polypeptide chain interact with the VH and VL domain (respectively) on a second polypeptide chain (see, for example, WO 02/02781). Diabodies of the current disclosure comprise an scFv molecule fused to a CH3 domain.

In certain embodiments, the binding proteins comprise multispecific or multivalent antibodies comprising one or more variable domain in series on the same polypeptide chain, e.g., tandem variable domain (TVD) polypeptides. Exemplary TVD polypeptides include the "double head" or "Dual-Fv" configuration described in U.S. Pat. No. 5,989,830. In the Dual-Fv configuration, the variable domains of two different antibodies are expressed in a tandem orientation on two separate chains (one heavy chain and one light chain), wherein one polypeptide chain has two VH in series separated by a peptide linker (VH1-linker-VH2) and the other polypeptide chain consists of complementary VL domains connected in series by a peptide linker (VL1-linker-VL2). In the cross-over double head configuration, the variable domains of two different antibodies are expressed in a tandem orientation on two separate polypeptide chains (one heavy chain and one light chain), wherein one polypeptide chain has two VH in series separated by a peptide linker (VH1-linker-VH2) and the other polypeptide chain consists of complementary VL domains connected in series by a peptide linker in the opposite orientation (VL2-linker-VL1). Additional antibody variants based on the "Dual-Fv" format include the Dual-Variable-Domain IgG (DVD-IgG) bispecific antibody (see U.S. Pat. No. 7,612,181 and the TBTI format (see US 2010/0226923 A1). The addition of constant domains to respective chains of the Dual-Fv (CH1-Fc to the heavy chain and kappa or lambda constant domain to the light chain) leads to functional bispecific antibodies without any need for additional modifications (i.e., obvious addition of constant domains to enhance stability).

In certain embodiments, the binding proteins comprise a cross-over dual variable domain IgG (CODV-IgG) bispecific antibody based on a "double head" configuration (see US20120251541 A1, which is incorporated by reference herein in its entirety). CODV-IgG antibody variants generally have one polypeptide chain with VL domains connected in series to a CL domain (VL1-L1-VL2-L2-CL) and a second polypeptide chain with complementary VH domains connected in series in the opposite orientation to a CH1 domain (VH2-L3-VH1-L4-CH1), where the polypeptide chains form a cross-over light chain-heavy chain pair. In certain embodiment, the second polypeptide may be further connected to an Fc domain (VH2-L3-VH1-L4-CH1-Fc).

In certain embodiments, the binding proteins comprise an immunoadhesin molecule comprising a non-antibody binding region (e.g., a receptor, ligand, or cell-adhesion molecule) fused to an antibody constant region (see e.g., Ashkenazi et al., Methods, 1995 8(2), 104-115, which is incorporated by reference herein in its entirety).

In certain embodiments, the binding proteins comprise an immunoglobulin-like domain. Suitable immunoglobulin-like domains include, without limitation, fibronectin domains (see, for example, Koide et al. (2007), Methods Mol. Biol. 352: 95-109, which is incorporated by reference herein in its entirety), DARPin (see, for example, Stumpp et al. (2008) Drug Discov. Today 13 (15-16): 695-701, which is incorporated by reference herein in its entirety), Z domains of protein A (see, Nygren et al. (2008) FEBS J. 275 (11): 2668-76, which is incorporated by reference herein in its entirety), lipocalins (see, for example, Skerra et al. (2008) *FEBS J.* 275 (11): 2677-83, which is incorporated by reference herein in its entirety), Affilins (see, for example, Ebersbach et al. (2007) *J. Mol. Biol.* 372 (1): 172-85, which is incorporated by reference herein in its entirety), Affitins (see, for example, Krehenbrink et al. (2008). *J. Mol. Biol.* 383 (5): 1058-68, which is incorporated by reference herein in its entirety), Avimers (see, for example, Silverman et al. (2005) *Nat. Biotechnol.* 23 (12): 1556-61, which is incorporated by reference herein in its entirety), Fynomers, (see, for example, Grabulovski et al. (2007) *J Biol Chem* 282 (5): 3196-3204, which is incorporated by reference herein in its entirety), and Kunitz domain peptides (see, for example, Nixon et al. (2006) *Curr Opin Drug Discov Devel* 9 (2): 261-8, which is incorporated by reference herein in its entirety).

In certain embodiments, the Fc domain-containing binding proteins of the invention are capable of binding one or more targets selected from the group consisting of ABCF1; ACVR1; ACVR1B; ACVR2; ACVR2B; ACVRL1; ADORA2A; Aggrecan; AGR2; AICDA; AIF1; AIG1;

AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAH; BCL2; BCL6; BDNF; BLNK; BLR1 (MDR15); BlyS; BMP1; BMP2; BMP3B (GDF10); BMP4; BMP6; BMP8; BMPRIA; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL2? (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM 145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EB11); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKN1C; CDKN2A (p161NK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYD1); CX3CR1 (V28); CXCL1 (GRO1); CXCL10 (IP-10); CXCL11 (1-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB2IP; DES; DKFZp451J0118; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; F1125530; FLRT1 (fibronectin); FLT1; FOS; FOSL1 (FRA-1); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC10 (C10); GRP; GSN (Gelsolin); GSTP1; HAVCR2; HDAC4; HDAC5; HDAC7A; HDAC9; HGF; HIF1A; HIP1; histamine and histamine receptors; HLA-A; HLA-DRA; HM74; HMOX1; HUMCYT2A; ICEBERG; ICOSL; ID2; IFN-α; IFNA1; IFNA2; IFNA4; IFNA5; IFNA6; IFNA7; IFNB1; IFNgamma; IFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMAS; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MKI67 (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2Rx7; PAP; PART1; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; S100A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Spr1); ST6GAL1; STAB1; STAT6; STEAP; STEAP2; TB4R2; TBX21; TCP10; TDGF1; TEK; TGFA; TGFB1; TGFB11; TGFB2; TGFB3; TGFB1; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-α; TNFAIP2 (B94); TNFAIP3; TNFRSF1A; TNFRSF1A; TNFRSF1B; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-IBB ligand); TOLLIP; Toll-like receptors; TOP2A (topoisomerase Iia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-1b); XCR1 (GPR5/CCXCR1); YY1; and ZFPM2.

IV. Engineered Binding Proteins

In certain preferred embodiments, the binding proteins produced using the methods and compositions disclosed herein exhibit improved properties (e.g., affinity or stability)

with respect to a corresponding parental reference binding protein. For example, the engineered binding protein may dissociate from its target antigen with a $k_{off}$ rate constant of about $0.1$ s$^{-1}$ or less, as determined by surface plasmon resonance, or inhibit the activity of the target antigen with an IC$_{50}$ of about $1\times10^{-6}$M or less. Alternatively, the binding protein may dissociate from the target antigen with a $k_{off}$ rate constant of about $1\times10^{-2}$ s$^{-1}$ or less, as determined by surface plasmon resonance, or may inhibit activity of the target antigen with an IC$_{50}$ of about $1\times10^{-7}$M or less. Alternatively, the binding protein may dissociate from the target with a $k_{off}$ rate constant of about $1\times10^{-3}$ s$^{-1}$ or less, as determined by surface plasmon resonance, or may inhibit the target with an IC$_{50}$ of about $1\times10^{-8}$M or less. Alternatively, binding protein may dissociate from the target with a $k_{off}$ rate constant of about $1\times10^{-4}$ s$^{-1}$ or less, as determined by surface plasmon resonance, or may inhibit its activity with an IC$_{50}$ of about $1\times10^{-9}$M or less. Alternatively, binding protein may dissociate from the target with a $k_{off}$ rate constant of about $1\times10^{-5}$ s$^{-1}$ or less, as determined by surface plasmon resonance, or inhibit its activity with an IC$_{50}$ of about $1\times10^{-10}$M or less. Alternatively, binding protein may dissociate from the target with a $k_{off}$ rate constant of about $1\times10^{-5}$ s$^{-1}$ or less, as determined by surface plasmon resonance, or may inhibit its activity with an IC$_{50}$ of about $1\times10^{-11}$ M or less.

In certain embodiments, the engineered binding protein comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the binding protein can comprise a light chain constant region, either a kappa light chain constant region or a lambda light chain constant region. The binding protein comprises a kappa light chain constant region. Alternatively, the binding protein portion can be, for example, a Fab fragment or a single chain Fv fragment.

In certain embodiments, the engineered binding protein comprises an engineered effector function known in the art (see, e.g., Winter, et al. U.S. Pat. Nos. 5,648,260; 5,624,821). The Fc portion of a binding protein mediates several important effector functions e.g. cytokine induction, ADCC, phagocytosis, complement dependent cytotoxicity (CDC) and half-life/clearance rate of binding protein and antigen-binding protein complexes. In some cases these effector functions are desirable for therapeutic binding protein but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of binding proteins. In still another embodiment at least one amino acid residue is replaced in the constant region of the binding protein, for example the Fc region of the binding protein, such that effector functions of the binding protein are altered.

In certain embodiments, the engineered binding protein is derivatized or linked to another functional molecule (e.g., another peptide or protein). For example, a labeled binding protein of the invention can be derived by functionally linking a binding protein or binding protein portion of the invention (by chemical coupling, genetic fusion, noncovalent association or otherwise) to one or more other molecular entities, such as another binding protein (e.g., a bispecific binding protein or a diabody), a detectable agent, a cytotoxic agent, a pharmaceutical agent, and/or a protein or peptide that can mediate associate of the binding protein with another molecule (such as a streptavidin core region or a polyhistidine tag).

Useful detectable agents with which a binding protein or binding protein portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. A binding protein may also be derivatized with detectable enzymes, such as alkaline phosphatase, horseradish peroxidase, glucose oxidase and the like. When a binding protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding protein may also be derivatized with biotin, and detected through indirect measurement of avidin or streptavidin binding.

In other embodiment, the engineered binding protein is further modified to generate glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the present invention.

Additionally or alternatively, an engineered binding protein of the invention can be further modified with an altered type of glycosylation, such as a hypofucosylated binding protein having reduced amounts of fucosyl residues or a binding protein having increased bisecting GlcNAc structures. Such altered glycosylation patterns have been demonstrated to increase the ADCC ability of binding proteins. Such carbohydrate modifications can be accomplished by, for example, expressing the binding protein in a host cell with altered glycosylation machinery. Cells with altered glycosylation machinery have been described in the art and can be used as host cells in which to express recombinant binding proteins of the invention to thereby produce a binding protein with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342 80, each of which is incorporated herein by reference in its entirety. Using techniques known in the art a practitioner may generate binding proteins exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

V. Production of Glycoengineered Binding Proteins

Binding proteins of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the binding proteins of the invention in either prokaryotic or eukaryotic host cells, expression of binding proteins in eukaryotic cells is preferable, and most preferable in mammalian host cells, because such eukaryotic cells (and in particular mammalian cells) are more likely than prokaryotic cells to assemble and secrete a properly folded and immunologically active binding protein.

Preferred mammalian host cells for expressing the recombinant binding proteins of the invention include Chinese Hamster Ovary (CHO cells) (including dhfr− CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. When recombinant expression vectors encoding binding protein genes are introduced into mammalian host cells, the binding proteins are produced by culturing the host cells for a period of time sufficient to allow for expression of the binding protein in the host cells or, more preferably, secretion of the binding protein into the culture medium in which the host cells are grown. Binding proteins can be recovered from the culture medium using standard protein purification methods. Additional methods of culturing antibody-producing mammalian cells are also taught, for example, in U.S. Pat. No. 8,663,945 which is incorporated herein in its entirety.

Host cells can also be used to produce functional binding protein fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of a binding protein of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the binding proteins of the invention. In addition, bifunctional binding proteins may be produced in which one heavy and one light chain are a binding protein of the invention and the other heavy and light chain are specific for an antigen other than the antigens of interest by crosslinking a binding protein of the invention to a second binding protein by standard chemical crosslinking methods.

In a preferred system for recombinant expression of a binding protein, or antigen-binding portion thereof, of the invention, a recombinant expression vector encoding both the binding protein heavy chain and the binding protein light chain is introduced into DHFR− CHO cells by calcium phosphate-mediated transfection. Within the recombinant expression vector, the binding protein heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the binding protein heavy and light chains and intact binding protein is recovered from the culture medium. Standard molecular biology techniques are used to prepare the recombinant expression vector, transfect the host cells, select for transformants, culture the host cells and recover the binding protein from the culture medium. Still further the invention provides a method of synthesizing a recombinant binding protein of the invention by culturing a host cell of the invention in a suitable culture medium until a recombinant binding protein of the invention is synthesized. The method can further comprise isolating the recombinant binding protein from the culture medium.

Glycoengineering of the binding proteins of the invention can be achieved by any methods known in the art. Suitable methods include: (1) glycosylation of purified binding proteins can be modified enzymatically in vitro, (2) the cell culture and production conditions can be modified to bias a defined glycosylation profile of recombinant proteins expressed in the cultured cells, (3) the protein can be engineered to add or eliminate sites for the attachment of glycans or (4) a cell line can be genetically engineered for production of biotherapeutics with a modified glycosylation profile. Exemplary methods of making glycoengineered Fc domain containing binding proteins can be found in the Examples herein.

In certain embodiments, glycoengineering of recombinant binding proteins is achieved by expression of Fc domain-containing binding proteins in cells capable of N-linked glycosylation under specific culture conditions. For example, growing CHO cells expressing recombinant antibodies in chemically defined culture media supplemented with metal ions such as manganese or ferric nitrate increases the G1F and G2F glycoforms of the expressed recombinant antibodies by at least 25-30% (see published U.S. Patent Application No. 2012/0276631, the contents of which are incorporated herein in their entirety and Example 1). In one embodiment, the Fc containing binding proteins are hypergalactosylated and/or hypomannosylated by expression in a host cell with a knock down or knock out of its beta galactosidase gene, for example, using beta galactosidase gene-specific RNAi, homologous recombination or Zn finger nuclease inactivation of the beta galactosidase gene (see Examples). In another embodiment, the Fc containing binding proteins are hypergalactosylated and/or hypomannosylated by expression in a host cell that overexpresses a galactosyl transferase. In other embodiments, the glycosylation of purified recombinant binding proteins is modified through enzymatic means, in vitro. For example, one or more glycosyltransferases may be employed to add specific saccharide residues to N-Glycans, and one or more glycosidases may be employed to remove unwanted saccharides from the N-linked glycan. Such enzymatic means are well known in the art (see. e.g., WO/2007/005786, which is incorporated herein by reference in its entirety). For example, purified recombinant antibodies can be hypergalactosylated in vitro in the presence of galactosyltransferase (see Warnock D. et al. (2005) In vitro galactosylation of human IgG at 1 kg scale using recombinant galactosyltransferase. Biotechnol. Bioeng. 92, 831-842). In Vitro Galactosylation and Sialylation of Glycoproteins with Terminal N-Acetylglucosamine and Galactose Residues has also been reported (Raju et al. Biochemistry, 2001, 40 (30), pp 8868-8876).

In other embodiments, mammalian cell lines are genetically engineered to modify the glycosylation profile of expressed recombinant binding proteins. For example, cells can be genetically engineered to overexpress human β1, 4-galactosyltransferase (E.C. 2.4.1.38; Weikert et al., Nature Biotechnology 17, 1116-1121 (1999)) or knock-out/knock down of β-galactosidase proteins. In other embodiments, the host cell is genetically engineered with one or more sialyltransferase enzymes, e.g., an a2,6 sialyltransferase (e.g., ST6Gal-1). Any natural or engineered cell (e.g., prokaryotic or eukaryotic) can be employed. In general, mammalian cells are employed to effect glycosylation. The N-glycans that are produced in mammalian cells are commonly referred to as complex N-glycans (see e.g., Drickamer K, Taylor M E (2006). Introduction to Glycobiology, 2nd ed., which is incorporated herein by reference in its entirety).

The glycoengineered binding polypeptides may be recovered from the culture supernatant of a glycoengineered host cell and subjected to one or more purification steps, such as, for example, ion-exchange or affinity chromatography, to further increase the G/M ratio of the binding composition. Suitable methods of purification will be apparent to a person of ordinary skill in the art. A person of ordinary skill in the art will appreciate that different combinations of purification methods, disclosed above, can lead to production of the polypeptide compositions with extremely high levels of galactosylation and extremely low levels of mannosylation. For example, the hypergalactosylated and/or hypomannosylated binding protein compositions obtained from glycoengineered host cells can be further glycoengineered using in vitro techniques. For example, the G/M ratio of said composition can be further increased by subjecting the composition to treatment with galactosyltransferases in vitro.

Galactosyltransferases are commercially available (Sigma Chemical Co, St. Louis, Mo.; Boehringer Mannheim, Indianapolis, Ind. and Genzyme, Cambridge Mass.).

Additionally or alternatively, compositions of the present invention can be further purified or modified so that they have an increased amount of sialic acid compared to reference antibody composition. The addition of charged sialic acid residue can help facilitate separation of the sialylated glycoforms by ion exchange chromatography (see e.g., FIG. 7C). For example, the sialylation levels of the composition can be increased for instance by subjecting the composition to treatment with sialyltransferases (e.g., an alpha 2,6 sialyltransferase). For example, hypergalactosylated and/or hypomannosylated binding protein compositions produced in CHO cells can be sialylated in vitro by subjecting the purified or partially purified binding protein composition to a sialyltransferase and the appropriate saccharide based substrate. Further, one may employ an enzymatic reaction with a sialyltransferase and a donor of sialic acid as described, for example, in the U.S. Pat. No. 7,473,680, which is incorporated herein by reference. Sialyltransferase enzymes are known in the art and are commercially available. Methods and compositions described herein include the use of a sialyltransferase enzyme, e.g., an a2,6 sialyltransferase (e.g., ST6Gal-1). A number of ST6Gal sialyltransferases are known in the art and are commercially available (see, e.g., Takashima, Biosci. Biotechnol. Biochem. 72:1 155-1 167 (2008); Weinstein et al., J. Biol. Chem. 262:17735-17743 (1987)). ST6Gal-1 catalyzes the transfer of sialic acid from a sialic acid donor (e.g., cytidine 5'-monophospho-N-acetyl neuraminic acid) to a terminal galactose residue of glycans through an a2,6 linkage. Accordingly, a purified or partially purified binding protein composition may contacted with an ST6Gal sialyltransferase (e.g., a recombinantly expressed and purified ST6Gal sialyltransferase) in the presence of a sialic acid donor, e.g., cytidine 5'-monophospho-N-acetyl neuraminic acid, manganese, and/or other divalent metal ions.

Additionally or alternatively, the composition can be sialylated in vivo by expressing the binding protein in a CHO cell that has been glycoengineered to express a sialyltransferase. Suitable non-limiting examples of sialyltransferase enzymes useful in the claimed methods are ST3Gal III, which is also referred to as alpha-(2,3)sialyltransferase (EC 2.4.99.6), and alpha-(2,6)sialyltransferase (EC 2.4.99.1). The alpha-2,3-sialyltransferase may be the human alpha-2,3-sialyltransferase, known as SIAT4C or STZ (GenBank accession number L23767), and described, for example, in the U.S. Patent Publication No. 20050181359. In yet other embodiments, the binding protein composition can be passed through a column having a lectin which is known to bind sialic acid in order to enrich for sialylated glycoforms. A person of the ordinary skill in the art will appreciate that different lectins display different affinities for alpha 2,6 versus alpha 2,3 linkages between galactose and sialic acid. Thus, selecting a specific lectin will allow enrichment of antibodies with the desired type of linkage between the sialic acid and the galactose. In one embodiment, the lectin is isolated from *Sambuccus nigra*. A person of the ordinary skill in the art will appreciate that the *Sambuccus nigra* agglutinin (SNA) is specific for sialic acids linked to galactose or N-acetylgalactosamine by alpha (2-6) linkages. Shibuya et al, J. Biol. Chem., 262: 1596-1601 (1987). In contrast, the *Maakia amurensis* ("MAA") lectin binds to sialic acid linked to galactose by a(2-3) linkages. Wang et al, J Biol. Chem., 263: 4576-4585 (1988). Thus, a fraction of the polypeptides containing at least one IgG Fc region having a desired linkage between the galactose and the sialic acid will be retained in the column while a fraction lacking such linkage will pass through. The sialylated fraction of the polypeptides containing at least one IgG Fc region can be eluted by another wash with a different stringency conditions. Thus, it is possible to obtain a preparation of the polypeptide of the present invention wherein the content of sialic acid is increased compared to the normal content.

In addition, a person of average skill in the art will appreciate that cell culture conditions can be manipulated to change the sialylation content. For example, to increase the sialic acid content, production rate is decreased and osmolality is generally maintained within a lower margin suitable for the particular host cell being cultured. Osmolality in the range from about 250 mOsm to about 450 mOsm is appropriate for increased sialic acid content. This and other suitable cell culture conditions are described in, e.g., U.S. Pat. No. 6,656,466. Patel et al., Biochem J, 285, 839-845 (1992) have reported that the content of sialic acid in antibody linked sugar side chains differs significantly if antibodies were produced as ascites or in serum-free or serum containing culture media. Moreover, Kunkel et al., Biotechnol. Prog., 16, 462-470 (2000) have shown that the use of different bioreactors for cell growth and the amount of dissolved oxygen in the medium influenced the amount of galactose and sialic acid in antibody linked sugar moieties.

VII. Purification of Glycoengineered Binding Proteins

Also provided is a process for manufacturing a glycoengineered binding composition of the invention by performing additional purification. In an embodiment, a process for manufacturing a composition of the invention is provided, comprising the following steps: i) recombinantly expressing the glycoengineered of interest in a host cell (e.g., a glycoengineered CHO cell of the invention) and; ii) purifying the binding protein of interest by subjecting a liquid containing said binding composition to one or more chromatographic steps. The respective manufacturing process leads to the production homogenous glycoprotein compositions which are in particular suitable for use in pharmaceutical formulations.

Accordingly, the compositions can be subjected to further chromatographic purification including, for example, ion exchange chromatography such anion exchange chromatography or cation exchange chromatography. Additional chromatography steps may include any of the following: a) reverse phase chromatography (RPC); b) size exclusion chromatography (SEC); and c) hydrophobic interaction chromatography (HIC); (d) affinity chromatography such as dye affinity chromatography, immune affinity chromatography, lectin affinity chromatography or perborate affinity chromatography, (e) filtration such as diafiltration, ultrafiltration or nanofiltration, and/or (f) at least one virus inactivation step. In an exemplary embodiment the process of the present invention includes an anion exchange chromatography (AEX) as a chromatography step. In another embodiment, AEX chromatography is performed subsequent to SEC chromatography and prior to HIC chromatography. Additional steps may be performed in addition to and also between the steps.

The purification methods may provide glycoengineered binding protein compositions in high purity, which may then be formulated as a pharmaceutical composition. For example, the purity may be above 90% hypergalactosylated binding protein, preferably >95% w/w, more preferably >99% w/w, even more preferably >99.5% w/w, based on total protein. In exemplary embodiments, the level of mannosylated species (e.g., M3-M9) is less than 10%, preferably <5% w/w, more preferably <1% w/w, even more preferably <0.5% w/w, based on total protein. In certain embodiments, the glycoprotein composition comprises only trace amounts of oligomannose glycoforms.

The binding protein compositions which form the starting material for the purification process may be provided in or obtained by recombinant techniques such as, e.g., in cell culture harvests of glycoengineered host cells of the invention. Typically, the starting material as obtained from a cell harvest, is clarified first (e.g. by filtration) and then optionally concentrated (e.g. by using ultrafiltration) and/or buffer exchanged (e.g. through a diafiltration step) prior to being captured by the first chromatographic step. In the steps of chromatography typically commercially available resins are used, preferably polymer-based resins or agarose-based resins. It is also possible to use membrane chromatography in which the resin is replaced by a functionalized membrane such as SARTOBIND® membranes (Sartorius) or CHROMASORB® (Millipore).

Anion Exchange (AEX) Chromatography

In certain embodiments, the glycoengineered binding compositions of the invention are subjected to an anion exchange (AEX) chromatography step. The anion exchange chromatography is usually performed by equilibrating and loading the column, followed by a wash and subsequent elution. The anion exchange chromatography is carried out, e.g., with a quaternary ammonium resin, such as CAPTOQ® (obtainable from GE Healthcare), or a resin having similar characteristics such as TOYOPEARL QEA® (obtainable from Tosoh), or FRACTOGEL EMD®, FRACTOGEL TMAE® or FRACTOGEL HICAP® (obtainable from Merck KGaA, Darmstadt Germany). Other exemplary anion exchange resins (i.e., the stationary phase) include, but are not limited to, quaternary amine resins or "Q-resins" (e.g., Q-Sepharose®, QAE Sephadex®); diethylaminoethane (DEAE) resins (e.g., DEAE-Trisacryl®, DEAE Sepharose®, benzoylated naphthoylated DEAE, diethylaminoethyl Sephacel®); Amberjet® resins; Amberlyst® resins; Amberlite® resins (e.g., Amberlite® IRA-67, Amberlite® strongly basic, Amberlite® weakly basic), cholestyramine resin, ProPac® resins (e.g., ProPac® SAX-10, ProPac® WAX-10, ProPac® WCX-10); TSK-GEL® resins (e.g., TSKgel DEAE-NPR; TSKgel DEAE-5PW); and Acclaim® resins. In certain embodiments, the anion exchange resin is a Q resin. In certain embodiments, the anion exchange resin is a DEAE resin. In certain embodiments, the DEAE resin is a TSK-GEL® DEAE resin.

Typical mobile phases for anionic exchange chromatography include relatively polar solutions, such as water and polar organic solvents (e.g., acetonitrile and organic alcohols such as methanol, ethanol, and isopropanol). Thus, in certain embodiments, the mobile phase comprises about 0%, 1%, 2%, 4%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, or about 100% acetonitrile. In certain embodiments, the mobile phase comprises between about 1% to about 100%, about 5% to about 95%, about 10% to about 90%, about 20% to about 80%, about 30% to about 70%, or about 40% to about 60% acetonitrile at any given time during the course of the separation.

In certain embodiments, the mobile phase is buffered. In certain embodiments, the mobile phase is not buffered. In certain embodiments, the mobile phase is buffered to a pH between about 7 to about 14. In certain embodiments, the mobile phase is buffered to a pH between about 7 to about 10. In certain embodiments, the mobile phase is buffered to a pH between about 7 to about 8. In certain embodiments, the mobile phase is buffered to a pH of about 7. Exemplary buffers for anion exchange chromatography are included in Table 1.

The anion exchange chromatography resin may be equilibrated, loaded and washed by using a buffer having a mildly alkaline pH, e.g. at or about 7.2 to at or about 9.0. Suitable buffers include, for example borate buffer, triethanolamine/iminodiacetic acid, Tris (2-Amino-2-hydroxymethyl-propane-1,3-diol), sodium phosphate, ammonium acetate, tricine (N-(Tri(hydroxymethyl)methyl)glycine), bicine (2-(bis (2-hydroxyethyl)amino)ethanoic acid), TES, HEPES, TAPS (N-Tris(hydroxymethyl)methyl-3-aminopropanesulfonic acid). Elution from the ion-exchange resin is achieved by increasing the conductivity of the mobile phase through the addition of salt, preferably NaCl. Suitable buffers include, for example borate buffer, triethanolamine/iminodiacetic acid Tris, ammonium acetate, tricine, bicine, TES, HEPES, TAPS. Preferred is ammonium acetate.

In certain exemplary embodiments, the anion exchange chromatography can be utilized to selectively elute different charged glycoforms mainly originating from different sialylation levels. For the selective elution of differently charged glycoforms, such as differently sialylated glycoforms, one may use two or more, preferably two elution buffers A and B which differ in pH and/or salt content, each of them being based on e.g. ammonium acetate, borate buffer, triethanolamine/iminodiacetic acid, Tris, sodium phosphate, ammonium acetate, tricine, bicine, TES, HEPES or TAPS, preferred is ammonium acetate. Using different elution buffers, elution can be performed in a stepwise fashion, first using one elution buffer and then using the other elution buffer, optionally also using one or more intermediate elution steps with different mixtures of the elution buffers. Alternatively or additionally, elution can be performed using a gradient, starting with a first mixing ratio of the elution buffers (e.g. 100% of the first elution buffer) and gradually changing to a second mixing ratio of the elution buffers (e.g. 100% of the second elution buffer). The elution buffer used first (buffer A) in general can be a) a mildly acidic buffer which is salt-free, or b) a neutral or mildly basic buffer with low salt content such as NaCl (preferably between 20 and 200 mM). Buffer A can be used to elute glycoforms of low charge, e.g., low degree of sialylation. In variant a) buffer A has a pH e.g. at or about 3.0 to at or about 6.5, or at or about 4.0 to at or about 6.0, most preferably at or about 5. In variant b) buffer A has a pH e.g. at or about 7.0 to 9.0, preferably 8.5. The elution buffer used second (buffer B) in general is a salt-containing mildly alkaline buffer of a higher salt content than buffer A which can be used to elute glycoprotein of high charge, e.g. high degree of sialylation. Buffer B has a pH e.g. at or about 7.0 to at or about 9.0, or at or about 8.0 to at or about 9.0, most preferably at or about 8.5. The salt is preferably NaCl. The salt content in buffer B is preferably from 200 mM to 1M. In certain exemplary embodiments, buffer A is 10 mM sodium phosphate, pH 7.5 and buffer B is 10 mM sodium phosphate/500 mM sodium chloride, pH 5.5.

Using different elution buffers and a gradient or stepwise elution, the different glycoforms loaded onto the anion exchange chromatography column will elute in different fractions depending on their charge. For example, the glycoprotein to be purified may be present in the fractions of the flow-through, i.e. it binds to the anion exchange chromatography column only weakly or not at all, it may be eluted with the first elution buffer, at a specific mixing ratio of the first and second elution buffer, or with the second elution buffer. The glycoprotein fractions which are used for the further purification steps and thus, the glycoforms which are to be purified, mainly depend on the desired applications of the glycoprotein. The other glycoforms which are not of interest can be removed using the anion exchange chromatography step.

As an alternative or additionally to standard anion exchange chromatography, chromatofocusing can be performed. Chromatofocusing is a chromatography technique that separates glycoforms according to differences in their isoelectric point (pI). In particular, a charged stationary phase can be used and the proteins loaded onto the chromatofocusing column can be eluted using a pH gradient. For example, the stationary phase may be positively charged and the pH gradient may develop from a first pH to a second, lower pH, for example from about pH 9 to about pH 6 or from about pH 7 to about pH 4. Due to the specific conditions of the chromatofocusing, glycoforms elute in order of their isoelectric points and preferably proteins of a specific pI are focused into narrow bands. Thus, as glycoforms at a pH higher than their pI are negatively charged and attach to the positively charged stationary phase, thereby being slowed down. When the pH in the elution gradient reaches the pI of the glycoform, it is overall neutral in charge and thus migrates with the flow of the mobile phase. At a pH lower than the pI of the protein, the glycoform is repulsed by the stationary phase due to its positive charge, thus accelerating it. Thereby glycoforms at the rear of a zone will migrate more rapidly than those at the front. In this setting, the glycoform with the highest pI elutes first and the glycoform with the lowest pI will elute last.

Suitable stationary phases are, for example, media substituted with charged, buffering amines such as MONO P (obtainable from GE Healthcare) or other anion exchange chromatography material. For forming the pH gradient for elution, suitable buffing systems such as POLYBUFFER 74® or POLYBUFFER 76® (obtainable from GE Healthcare) can be used. Equilibration, loading and washing of the column can be done using any condition where the glycoprotein of interest and/or any impurities bind to the column material. For example, conditions as described above for the anion exchange chromatography can be used. When using a decreasing pH gradient, preferably a buffer having a pH equal to or higher than the starting pH of the elution gradient is used for equilibration, loading and/or washing. When using an increasing pH gradient, preferably a buffer having a pH equal to or lower than the starting pH of the elution gradient is used for equilibration, loading and/or washing.

Reverse Phase Chromatography Reverse phase chromatography refers to a chromatography step wherein a non-polar stationary phase and preferably a polar mobile phase are used. In reverse phase chromatography, normally polar compounds are eluted first while non-polar compounds are retained. The reverse phase chromatography is usually performed by equilibrating and loading the column, followed by a wash and subsequent elution, each with a buffer preferably containing an organic solvent such as acetonitrile or isopropanol. The organic solvent such as isopropanol can be used for virus inactivation subsequent to elution. Preferably the organic solvent is a water miscible organic solvent such as acetonitrile or an alcohol (such as methanol, ethanol, etc./). Reversed phase column material is made of a resin to which a hydrophobic material may be attached. Typical column materials are silica and polystyrene; hydrophobic ligands may optionally be attached. In case of substituted resins, the resin is substituted with a hydrophobic ligand, typically selected from (but not limited to) aliphates, such as $C_2$, $C_4$, $C_6$, $C_8$, $C_{10}$, $C_{12}$, $C_{14}$, $C_{16}$, or $C_{18}$ or derivatives of these, e.g. cyanopropyl (CN-propyl), or branched aliphates, or benzene-based aromates, such as phenyl, or other polar or non-polar ligands. The ligand may be a mixture of two or more of these ligands. Suitable polystyrene based resins include, without limitation, resins supplied by Rohm Haas (e.g. Amberlite XAD® or Amberchrom CG®), Polymer Labs (e.g. PLRP-S®), GE Healthcare (e.g. Source RPC®), Applied Biosystems (e.g. Poros R®)). A particularly preferred resin is Source 30 RPC® (GE Healthcare).

Viral Inactivation

In certain embodiments, the purification process can include a virus inactivation step. Virus inactivation may be achieved by incubating the protein loaded onto, bound to or eluted from the column in the presence of an organic solvent, preferably isopropanol or ethanol. The incubation time and incubation temperature preferably are chosen so as to affect a desired degree of virus inactivation and in particular depend on the concentration and nature of the organic solvent used. Furthermore, these parameters should also be adjusted depending on the stability of the binding protein composition to be purified. For example, the protein is incubated for at least 15 min, preferably for at least 30 min, at least 45 min, at least 1 h, at least 2 h, at least 3 h or at least 6 h. The incubation can be performed at low temperature such as at or below 4° C. or at or below 10° C., or it can be performed at about room temperature. The incubation can be performed directly after the sample has been loaded onto the column, during or after the washing step, after applying the elution buffer but prior to elution of the glycoprotein, or after elution of the binding protein. If isopropanol is used as the organic solvent, virus inactivation is preferably done at an isopropanol concentration of at least 15% (v/v), preferably at about 18% (v/v). In this case, the binding protein is preferably incubated for about 2 h, preferably at room temperature. Preferably, the virus inactivation is performed after elution of the glycoprotein from the reverse phase chromatography column, preferably in the elution buffer used. However, optionally further components may be added to the glycoprotein solution after elution from the column, in particular for enhancing the virus inactivation and/or the binding protein stability.

Size Exclusion Chromatography

The purification process may include a step of size exclusion chromatography, e.g. for further purifying and/or re-buffering of the binding protein composition. Size exclusion chromatography comprises the step of equilibrating and loading the eluate of the previous chromatography step to a gel filtration matrix equilibrated with a buffer having a composition which is desired for storage or further processing of the glycoprotein at a pH of typically between 6.5 and 9. For performing size exclusion chromatography, the gel is typically selected from the groups of polymeric gels including, but not limited to dextra-based gels such as SEPHADEX® (e.g. SEPHADEX G-25®) or polyacrylamide gels such as SEPHACRYL® (e.g. SEPHACRYL-S400®), agarose-based gels such as SUPEROSE® or SEPHAROSE® (e.g. SEPHAROSE CL-4B®), and composite gels prepared from two kinds of gels such as SUPERDEX 200® combining DEXTRAN® (SEPHADEX®) and crosslinked Agarose (SUPEROSE®) gels. Buffers may be selected from the group consisting sodium phosphate, ammonium acetate, MES (2-(N-morpholino)ethanesulfonic acid), Bis-Tris (2-bis(2-hydroxyethyl)amino-2-(hydroxymethyl)-1,3-propanediol), ADA (N-(2-Acetamido) iminodiacetic acid), PIPES (piperazine-N,N'-bis(2-ethanesulfonic acid), ACES (N-(2-Acetamido)-2-aminoethanesulfonic acid), BES (N,N-Bis(2-hydroxyethyl)-2-aminoethane-sulfonic acid), MOPS (3-(N-morpholino) propanesulfonic acid), TES (N-Tris(hydroxymethyl)methyl-2-aminoethanesulfonic acid), HEPES (N-2-Hydroxyethyl-piperazine-N'-2-ethanesulfonic acid), sodium phosphate or ammonium acetate. Said buffer may additionally comprise an inorganic salt, e.g., a halide of an alkaline metal, e.g., potassium chloride or sodium chloride and/or an antioxidant, such as L-methionine, t-butyl-4-methoxyphenol, 2,6-bis(1,1-dimethylethyl)-4-methyl phenol; potassium or sodium bimetabisulfite, sodium bisulfite. The size exclusion chromatography may further comprise the step of eluting the binding protein from said gel filtration matrix by isocratic elution, i.e. the elution buffer has about the same, preferably the same composition as the buffer used for equilibration and/or loading. The flow through may be recorded by UV absorption at 280 nm and the fraction containing the glycoprotein is collected.

Hydrophobic Interaction Chromatography (HIC)

HIC is a separation method that takes advantage of the hydrophobic properties of the proteins. The adsorption is promoted by the hydrophobic interactions between non-polar regions on the protein and immobilized hydrophobic ligands on a solid support. Adsorption is achieved at high salt concentrations in the aqueous mobile phase and elution is facilitated by decreasing the salt concentration. The hydrophobic interaction chromatography material is a matrix substituted with hydrophobic ligands such as ethyl-, butyl-, phenyl- or hexyl-groups. Preferred material is a matrix substituted with a butyl or a phenyl ligand. Hydrophobic Interaction Chromatography (HIC) resins are known in the art and include resins such as BUTYL SEPHAROSE® (GE Healthcare), PHENYL SEPHAROSE® (low and high substitution), OCTYL SEPHAROSE® and ALKYL SEPHAROSE® (all of GE Healthcare; other sources of HIC resins include Biosepra, France; E. Merck, Germany; BioRad USA). Alternative resins that may be used are as follows: TOYOPEARL BUTYL 650M® (obtainable from Tosoh Biosep Inc.), PHENYL SEPHAROSE 6 FAST FLOW® (low sub); PHENYL SEPHAROSE 6 FAST FLOW® (high sub); BUTYL SEPAROSE 4 FAST FLOW®; OCTYL SEPHAROSE 4 FAST FLOW® PHENYL SEPHAROSE HIGH PERFORMANCE® SOURCE 15ETH®; SOURCE 15ISO®; SOURCE 15PHE® all from GE Biosciences (800) 526-3593. Still further resins are: HYDROCELL® C3 or C4; HYDROCELL PHENYL® from BioChrom Labs Inc. (812) 234-2558. Equilibration, loading, wash and elution buffers may be selected from the group consisting of sodium phosphate, MES, Bis-Tris, ADA, PIPES, ACES, BES, MOPS, TES, HEPES. Binding on the HIC resin is in general achieved by using an equilibration and loading buffer with a high conductivity, obtained e.g. through the addition of salt such as NaCl, (NH4)2SO4 or Na2SO4, preferably ammonium sulfate. Exemplary salt concentrations are 1 to 2M. The wash generally uses the loading buffer. Elution in the step of hydrophobic interaction chromatography is preferably carried out by reducing the conductivity of the mobile phase (reducing salt concentration). The reduction can be achieved in a linear way or step-wise.

Other Purification Steps

Prior to the first chromatography step, it may be desirable to carry out a step of ultrafiltration, in order to concentrate the crude binding protein. Furthermore, additionally a step of diafiltration may be performed prior to the first chromatography step in order to perform a buffer exchange. The ultrafiltration step and the diafiltration step may be performed simultaneously or sequentially. The ultrafiltration and/or diafiltration is preferably carried out using a membrane having a cut-off of at or about 3-30 kD, most preferably at or about 10 kD. It is preferred to perform during ultrafiltration and/or diafiltration a buffer exchange to a pre-formulation buffer, e.g. selected from the group consisting of sodium phosphate, sodium citrate, MES, Bis-Tris, ADA, PIPES, ACES, BES, MOPS, TES, HEPES, preferably sodium phosphate, preferably sodium-phosphate containing stabilizers e.g. sucrose and antioxidants like L-methionine. The pH preferably is in the range of 6.5 to 7.5, more preferably about 7.0 to 7.1.

Further optional steps which can be performed in the purification process according to the invention include one or more sterile filtration steps. These steps can be used to remove biological contaminations such as eukaryotic and/or prokaryotic cells, in particular bacteria, and/or viruses. Preferably, these steps are performed at or near the end of the purification process to prevent a further contamination after the sterile filtration step. For removal of bacteria or other cells, the filter used for sterile filtration preferably has a pore size of 0.22 µm or less, preferably 0.1 µm or less. For removal of viruses or virus-like particles, a nanofiltration step may also be performed.

Storage/Lyophilisation

The binding protein composition resulting from the purification process as described above and containing purified glycoprotein may be frozen for storage as is, or after purification, the eluate may be subjected to lyophilisation ("freeze-drying") to remove solvent.

VIII. Pharmaceutical Compositions

In one aspect, pharmaceutical compositions comprising one or more population of binding proteins, either alone or in combination with prophylactic agents, therapeutic agents, and/or pharmaceutically acceptable carriers are provided. The pharmaceutical compositions provided herein are for use in, but not limited to, diagnosing, detecting, or monitoring a disorder, in preventing, treating, managing, or ameliorating a disorder or one or more symptoms thereof, and/or in research. The formulation of pharmaceutical compositions, either alone or in combination with prophylactic agents, therapeutic agents, and/or pharmaceutically acceptable carriers, is known to one skilled in the art (US Patent Publication No. 20090311253 A1).

Methods of administering a prophylactic or therapeutic agent provided herein include, but are not limited to, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

One embodiment provides a composition for the release of a binding protein wherein the composition comprises a formulation that in turn comprises a crystallized binding protein, as disclosed herein, and an ingredient, and at least one polymeric carrier. For example, the polymeric carrier is a polymer selected from one or more of the group consisting of: poly(acrylic acid), poly(cyanoacrylates), poly(amino acids), poly(anhydrides), poly(depsipeptide), poly (esters), poly(lactic acid), poly(lactic-co-glycolic acid) or PLGA, poly(b-hydroxybutryate), poly(caprolactone), poly(dioxanone); poly(ethylene glycol), poly((hydroxypropyl)methacrylamide, poly[(organo)phosphazene], poly(ortho esters), poly(vinyl alcohol), poly(vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. For example, the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed herein.

The "solubility" of a mAb correlates with the production of correctly folded, monomeric IgG. The solubility of the IgG may therefore be assessed by HPLC. For example, soluble (monomeric) IgG will give rise to a single peak on the HPLC chromatograph, whereas insoluble (e.g., multimeric and aggregated) will give rise to a plurality of peaks. A person skilled in the art will therefore be able to detect an increase or decrease in solubility of an IgG using routine HPLC techniques. For a more comprehensive list of analytical techniques that may be employed to analyze solubility (see Jones, A. G. Dep. Chem. Biochem. Eng., Univ. Coll. London, London, UK. Editor(s): Shamlou, P. Ayazi. Process. Solid-Liq. Suspensions (1993), 93-117. Publisher: Butterworth-Heinemann, Oxford, UK and Pearlman, Rodney; Nguyen, Tue H, Advances in Parenteral Sciences (1990), 4 (Pept. Protein Drug Delivery), 247-301). Solubility of a therapeutic mAb is critical for formulating to high concentration often required for adequate dosing. As outlined herein, solubilities of >100 mg/mL may be required to accommodate efficient antibody dosing. For instance, antibody solubility may be not less than about 5 mg/mL in early research phase, in an embodiment not less than about 25 mg/mL in advanced process science stages, or in an embodiment not less than about 100 mg/mL, or in an embodiment not less than about 150 mg/mL. It is obvious to a person skilled in the art that the intrinsic properties of a protein molecule are important the physico-chemical properties of the protein solution, e.g., stability, solubility, viscosity. However, a person skilled in the art will appreciate that a broad variety of excipients exist that may be used as additives to beneficially impact the characteristics of the final protein formulation. These excipients may include: (i) liquid solvents, cosolvents (e.g., alcohols such as ethanol); (ii) buffering agents (e.g., phosphate, acetate, citrate, amino acid buffers); (iii) sugars or sugar alcohols (e.g., sucrose, trehalose, fructose, raffinose, mannitol, sorbitol, dextrans); (iv) surfactants (e.g., polysorbate 20, 40, 60, 80, poloxamers); (v) isotonicity modifiers (e.g., salts such as NaCl, sugars, sugar alcohols); and (vi) others (e.g., preservatives, chelating agents, antioxidants, chelating substances (e.g., EDTA), biodegradable polymers, carrier molecules (e.g., HSA, PEGs).

The methods of the invention encompasse administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The binding proteins of the invention can be incorporated into a pharmaceutical composition suitable for parenteral administration. In an embodiment, the antibody or antibody-portions will be prepared as an injectable solution containing 0.1-250 mg/ml binding protein. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the binding proteins of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, and US2006104968).

The buffer of antibody is either 5.57 mM sodium phosphate monobasic, 8.69 mM sodium phosphate dibasic, 106.69 mM NaCl, 1.07 mM sodium citrate, 6.45 mM citric acid, 66.68 mM mannitol, 0.1% (w/v) Tween, pH 5.2; or 10 mM histidine, 10 mM methionine, 4% mannitol, pH 5.9 using Amicon ultra centrifugal filters. The final concentration of the antibodies is adjusted to 2 mg/mL with the appropriate buffers. The antibody solutions are then filter sterized and 0.25 mL aliquots are prepared under sterile conditions. The aliquots are left at either −80° C., 5° C., 25° C., or 40° C. for 1, 2 or 3 weeks. At the end of the incubation period, the samples are analyzed by size exclusion chromatography and SDS-PAGE.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms provided herein are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a binding protein provided herein is 0.1-20 mg/kg, for example, 1-10 mg/kg. It is to be noted that dosage values may vary with the type and severity of the condition to be alleviated. It is to be further understood that for any particular subject, specific dosage regimens may be adjusted over time according to the individual need and the professional judgment of the person administering or supervising the administration of the compositions, and that dosage ranges set forth herein are exemplary only and are not intended to limit the scope or practice of the claimed composition.

IX. Methods of Treatment Using Tnf Binding Molecules

In one aspect, provided herein are methods of treating a TNF-associated disorder in a subject by administering to the individual in need of such treatment a therapeutically effective amount of a composition comprising a glycoengineered population of TNF binding proteins disclosed herein. Such methods can be used to treat any TNF-associated disorder including, without limitation:

1) Sepsis

Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e.g., Moeller, A., et al. (1990) Cytokine 2:162-169; U.S. Pat. No. 5,231,024 to Moeller et al.; European Patent Publication No. 260 610 B1 by Moeller, A.; Tracey, K. J. and Cerami, A. (1994) Annu. Rev. Med. 45:491-503; Russell, D and Thompson, R. C. (1993) Curr. Opin. Biotech. 4:714-721). Accordingly, a TNF binding proteins of the invention can be used to treat sepsis in any of its clinical settings, including septic shock, endotoxic shock, gram negative sepsis and toxic shock syndrome.

Furthermore, to treat sepsis, a combination of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e.g., PCT Publication No. WO 93/11793) or an antagonist of platelet activating factor (see e.g., European Patent Application Publication No. EP 374 510). Other combination therapies for the treatment of sepsis are discussed further in herein.

Additionally, in certain embodiments, a TNF binding proteins of the invention is administered to a human subject within a subgroup of sepsis patients having a serum or plasma concentration of IL-6 above 500 pg/ml (e.g., above 1000 pg/ml) at the time of treatment (see PCT Publication No. WO 95/20978 by Daum, L., et al.).

2) Autoimmune Diseases

Tumor necrosis factor has been implicated in playing a role in the pathophysiology of a variety of autoimmune diseases. For example, TNF-alpha has been implicated in activating tissue inflammation and causing joint destruction in rheumatoid arthritis (see e.g., Moeller, A., et al. (1990) Cytokine 2:162-169; U.S. Pat. No. 5,231,024 to Moeller et al.; European Patent Publication No. 260 610 B1 by Moeller, A.; Tracey and Cerami, supra; Arend, W. P. and Dayer, J-M. (1995) Arth. Rheum. 38:151-160; Fava, R. A., et al. (1993) Clin. Exp. Immunol. 94:261-266). TNF-alpha also has been implicated in promoting the death of islet cells and in mediating insulin resistance in diabetes (see e.g., Tracey and Cerami, supra; PCT Publication No. WO 94/08609). TNF-alpha also has been implicated in mediating cytotoxicity to oligodendrocytes and induction of inflammatory plaques in multiple sclerosis (see e.g., Tracey and Cerami, supra). Chimeric and humanized murine anti-hTNF-alpha antibodies have undergone clinical testing for treatment of rheumatoid arthritis (see e.g., Elliott, M. J., et al. (1994) Lancet 344:1125-1127; Elliot, M. J., et al. (1994) Lancet 344:1105-1110; Rankin, E. C., et al. (1995) Br. J. Rheumatol. 34:334-342).

Compositions of the invention can be used to treat autoimmune diseases, in particular those associated with inflammation, including rheumatoid arthritis, rheumatoid spondylitis, osteoarthritis and gouty arthritis, allergy, multiple sclerosis, autoimmune diabetes, autoimmune uveitis and nephrotic syndrome. Typically, the combination is administered systemically, although for certain disorders, local administration of the anti-TNF and/or JAK inhibitor at a site of inflammation may be beneficial (e.g., local administration in the joints in rheumatoid arthritis or topical application to diabetic ulcers, alone or in combination with a cyclohexaneylidene derivative as described in PCT Publication No. WO 93/19751). Compositions of the invention also can be administered with one or more additional therapeutic agents useful in the treatment of autoimmune diseases, as discussed further herein.

3) Infectious Diseases

Tumor necrosis factor has been implicated in mediating biological effects observed in a variety of infectious diseases. For example, TNF-alpha has been implicated in mediating brain inflammation and capillary thrombosis and infarction in malaria. TNF-alpha also has been implicated in mediating brain inflammation, inducing breakdown of the blood-brain bather, triggering septic shock syndrome and activating venous infarction in meningitis. TNF-alpha also has been implicated in inducing cachexia, stimulating viral proliferation and mediating central nervous system injury in acquired immune deficiency syndrome (AIDS). Accordingly, the compositions of the invention, can be used in the treatment of infectious diseases, including bacterial meningitis (see e.g., European Patent Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze, E., et al. (1994) Transplantation 58:675-680). Compositions of the invention, also can be used to alleviate symptoms associated with infectious diseases, including fever and myalgias due to infection (such as influenza) and cachexia secondary to infection (e.g., secondary to AIDS or ARC).

4) Transplantation

Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e.g., Eason, J. D., et al. (1995) Transplantation 59:300-305; Suthanthiran, M. and Strom, T. B. (1994) New Engl. J. Med. 331:365-375). Accordingly, compositions of the invention, can be used to inhibit transplant rejection, including rejections of allografts and xenografts and to inhibit GVHD. Although the combination may be used alone, it can be used in combination with one or more other agents that inhibit the immune response against the allograft or inhibit GVHD. For example, in one embodiment, a TNF binding protein is used in combination with OKT3 to inhibit OKT3-induced reactions. In another embodiment, a TNF binding protein is used in combination with one or more antibodies directed at other targets involved in regulating immune responses, such as the cell surface molecules CD25 (interleukin-2 receptor-$\alpha$.), CD11a (LFA-1), CD54 (ICAM-1), CD4, CD45, CD28/CTLA4, CD80 (B7-1) and/or CD86 (B7-2). In yet another embodiment, a TNF binding protein of the invention is used in combination with one or more general immunosuppressive agents, such as cyclosporin A or FK506.

5) Malignancy

Tumor necrosis factor has been implicated in inducing cachexia, stimulating tumor growth, enhancing metastatic potential and mediating cytotoxicity in malignancies. Accordingly, a TNF binding protein of the invention can be used in the treatment of malignancies, to inhibit tumor growth or metastasis and/or to alleviate cachexia secondary to malignancy. The compositions may be administered systemically or locally to the tumor site.

6) Pulmonary Disorders

Tumor necrosis factor has been implicated in the pathophysiology of adult respiratory distress syndrome (ARDS), including stimulating leukocyte-endothelial activation, directing cytotoxicity to pneumocytes and inducing vascular leakage syndrome. Accordingly, a TNF binding protein of the invention, can be used to treat various pulmonary disorders, including adult respiratory distress syndrome (see e.g., PCT Publication No. WO 91/04054), shock lung, chronic pulmonary inflammatory disease, pulmonary sarcoidosis, pulmonary fibrosis and silicosis. The compositions may be administered systemically or locally to the lung surface, for example as an aerosol. A composition of the invention also can be administered with one or more additional therapeutic agents useful in the treatment of pulmonary disorders, as discussed further in herein.

7) Intestinal Disorders

Tumor necrosis factor has been implicated in the pathophysiology of inflammatory bowel disorders (see e.g., Tracy, K. J., et al. (1986) Science 234:470-474; Sun, X-M., et al. (1988) J. Clin. Invest. 81:1328-1331; MacDonald, T. T., et al. (1990) Clin. Exp. Immunol. 81:301-305). Chimeric murine anti-hTNF-alpha antibodies have undergone clinical testing for treatment of Crohn's disease (van Dullemen, H. M., et al. (1995) Gastroenterology 109:129-135). The compositions of the invention, also can be used to treat intestinal disorders, such as idiopathic inflammatory bowel disease, which includes two syndromes, Crohn's disease and ulcerative colitis. A composition of the invention also can be administered with one or more additional therapeutic agents useful in the treatment of intestinal disorders, as discussed further in herein.

8) Cardiac Disorders

The compositions of the invention, also can be used to treat various cardiac disorders, including ischemia of the heart (see e.g., European Patent Application Publication No. EP 453 898) and heart insufficiency (weakness of the heart muscle) (see e.g., PCT Publication No. WO 94/20139).

9) Other Disorders

The compositions of the invention, also can be used to treat various other disorders in which TNF-alpha activity is detrimental. Examples of other diseases and disorders in which TNF-alpha activity has been implicated in the pathophysiology, and thus which can be treated using a TNF binding protein of the invention, include inflammatory bone disorders and bone resorption disease (see e.g., Bertolini, D. R., et al. (1986) Nature 319:516-518; Konig, A., et al. (1988) J. Bone Miner. Res. 3:621-627; Lerner, U. H. and Ohlin, A. (1993) J. Bone Miner. Res. 8:147-155; and Shankar, G. and Stern, P. H. (1993) Bone 14:871-876); hepatitis, including alcoholic hepatitis (see e.g., McClain, C. J. and Cohen, D. A. (1989) Hepatology 9:349-351; Felver, M. E., et al. (1990) Alcohol. Clin. Exp. Res. 14:255-259; and Hansen, J., et al. (1994) Hepatology 20:461-474), viral hepatitis (Sheron, N., et al. (1991) J. Hepatol. 12:241-245; and Hussain, M. J., et al. (1994) J. Clin. Pathol. 47:1112-1115), and fulminant hepatitis; coagulation disturbances (see e.g., van der Poll, T., et al. (1990) N. Engl. J. Med. 322:1622-1627; and van der Poll, T., et al. (1991) Prog. Clin. Biol. Res. 367:55-60); burns (see e.g., Giroir, B. P., et al. (1994) Am. J. Physiol. 267:H118-124; and Liu, X. S., et al. (1994) Burns 20:40-44); reperfusion injury (see e.g., Scales, W. E., et al. (1994) Am. J. Physiol. 267:G1122-1127; Serrick, C., et al. (1994) Transplantation 58:1158-1162; and Yao, Y. M., et al. (1995) Resuscitation 29:157-168); keloid formation (see e.g., McCauley, R. L., et al. (1992) J. Clin. Immunol. 12:300-308), scar tissue formation; pyrexia; periodontal disease; obesity; and radiation toxicity.

In certain embodiments, an compositions of the invention is used for the treatment of a TNF-associated disorder selected from the group consisting of osteoarthritis, rheumatoid arthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis, scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic polyglandular deficiency type I, polyglandular deficiency type II (Schmidt's syndrome), adult (acute) respiratory distress syndrome, alopecia, alopecia greata, seronegative arthropathy, arthropathy, Reiter's disease, psoriatic arthropathy, ulcerative colitic arthropathy, enteropathic synovitis, *Chlamydia*-associated arthropathy, *Yersinia*-associated arthropathy, *Salmonella*-associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free disease, chronic mucocutaneous candidiasis, giant cell arteritis, primary sclerosing hepatitis, cryptogenic autoimmune hepatitis, acquired immunodeficiency syndrome, acquired immunodeficiency related diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, cholestasis, idiosyncratic liver disease, drug-induced hepatitis, non-alcoholic steatohepatitis, allergy, group B streptococci (GBS) infection, mental disorders (e.g., depression and schizophrenia), Th2 Type and Th1 Type mediated diseases, acute and chronic pain (different forms of pain), cancers such as lung, breast, stomach, bladder, colon, pancreas, ovarian, prostate and rectal cancer and hematopoietic malignancies (leukemia and lymphoma), abetalipoproteinemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, atrial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetic arteriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hemophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemochromatosis, hemodialysis, hemolytic uremic syndrome/thrombolytic thrombocytopenic purpura, hemorrhage, hepatitis A, His bundle arrhythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, asthenia, infantile spinal muscular atrophy, inflammation of the aorta, influenza A, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphedema, malaria, malignant lymphoma, malignant histiocytosis, malignant melanoma, meningitis, meningococcemia, metabolic migraine headache, idiopathic migraine headache, mitochondrial multisystem disorder, mixed connective tissue disease, monoclonal gammopathy, multiple myeloma, multiple systems degenerations (Menzel, Dejerine-Thomas, Shy-Drager, and Machado-Joseph), myasthenia gravis, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, neurodegenerative diseases, neurogenic muscular atrophies, neutropenic fever, non-Hodgkin's lymphoma, occlusion of the abdominal aorta and its branches, occlusive arterial disorders, orchitis/epididymitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon, Raynaud's disease, Refsum's disease, regular narrow QRS tachycardia, renovascular hypertension, reperfusion injury, restrictive cardiomyopathy, sarcomas, senile chorea, senile dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, subacute sclerosing panencephalitis, syncope, syphilis of the cardiovascular system, systemic anaphylaxis, systemic inflammatory response syndrome, systemic onset juvenile rheumatoid arthritis, telangiectasia, thromboangiitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, viral-associated hemophagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, alopecia greata, anaphylaxis, anti-phospholipid antibody syndrome, aplastic anemia, arteriosclerosis, atopic eczema, atopic dermatitis, autoimmune dermatitis, autoimmune disorder associated with streptococcus infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (CIS) with risk for multiple sclerosis, childhood onset psychiatric disorder, chronic obstructive pulmonary disease (COPD), dacryocystitis, dermatomyositis, diabetic retinopathy, disk herniation, disk prolapse, drug induced immune hemolytic anemia, endocarditis, endometriosis, endophthalmitis, episcleritis, erythema multiforme, erythema multiforme major, gestational pemphigoid, Guillain-Barre syndrome (GBS), hay fever, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojunctivitis sicca, Kussmaul disease or Kussmaul-Meier disease, Landry's paralysis, Langerhan's cell histiocytosis, livedo reticularis, macular degeneration, microscopic polyangiitis, Morbus Bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, ovarian cancer, pauciarticular JRA, peripheral artery occlusive disease (PAOD), peripheral vascular disease (PVD), peripheral artery disease (PAD), phlebitis, polyarteritis nodosa (or periarteritis nodosa), polychondritis, polymyalgia rheumatica, poliosis, polyarticular JRA, polyendocrine deficiency syndrome, polymyositis, polymyalgia rheumatica (PMR), post-pump syndrome, primary Parkinsonism, prostate and rectal cancer and hematopoietic malignancies (leukemia and lymphoma), prostatitis, pure red cell aplasia, primary adrenal insufficiency, recurrent neuromyelitis optica, restenosis, rheumatic heart disease, SAPHO (synovitis, acne, pustulosis, hyperostosis, and osteitis), secondary amyloidosis, shock lung, scleritis, sciatica, secondary adrenal insufficiency, silicone associated connective tissue disease, Sneddon-Wilkinson dermatosis, spondylitis ankylosans, Stevens-Johnson syndrome (SJS), systemic inflammatory response syndrome, temporal arteritis, toxoplasmic retinitis, toxic epidermal necrolysis, transverse myelitis, TRAPS (tumor-necrosis factor receptor type 1 (TNFR)-associated periodic syndrome), type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), and wet macular degeneration. In a particular embodiment, the TNF-associated disease or disorder is rheumatoid arthritis.

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the packaging vectors, cell lines and/or methods of the

Example 1

Figure 2A:
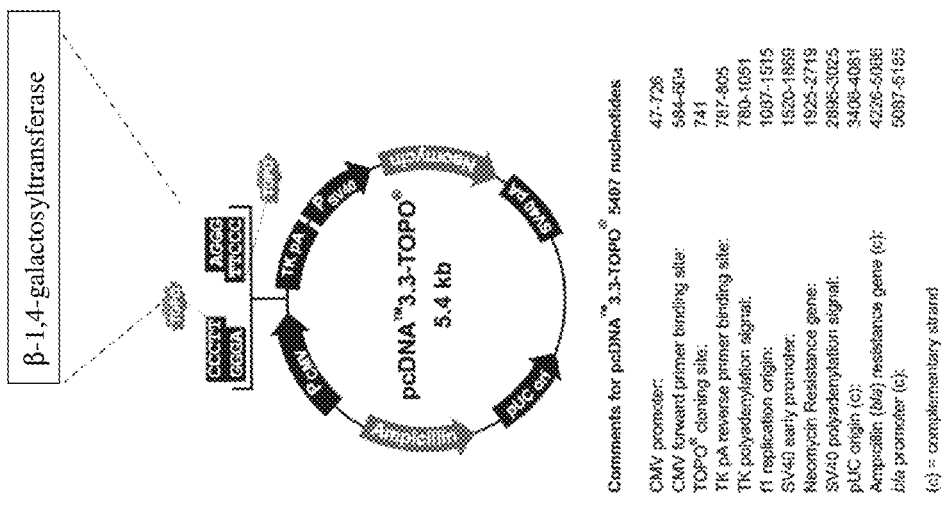
FIG. 2A shows the cloning of mouse beta1-4 galactosyltransferase into the mammalian expression vector, pCDN3.3.
Figure 2B:
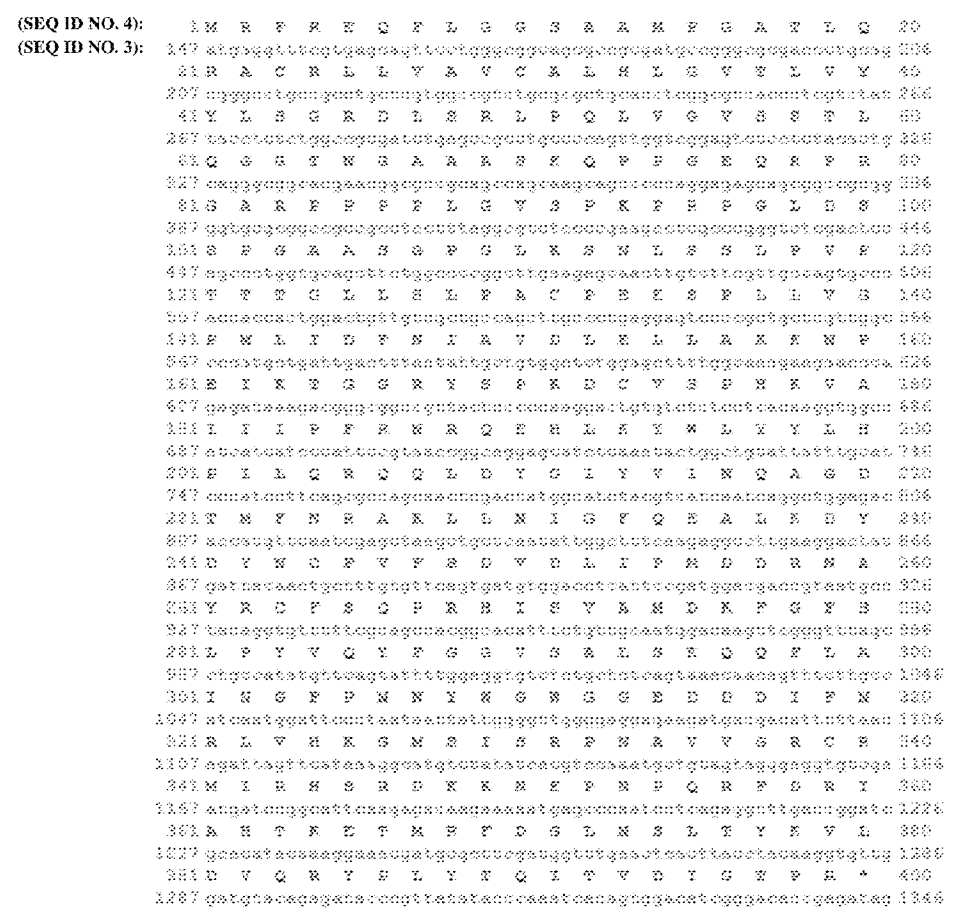

Generation of Monoclonal Antibody-Producing Cho Cells Overexpressing β1, 4 Galactosyl-Transferase A mouse galactosyltransferase β1, 4 (Genbank accession number: D00314) was amplified by PCR and cloned downstream of CMV promoter of the pcDNA™3.3 TOPO® Mammalian Expression Vector (Invitrogen Life Sciences, Catalog Number: K8300-01) as shown in FIG. 2A. The nucleic acid and corresponding amino acid sequence of mouse galactosyltransferase β1, 4 is shown in FIG. 2B.

Adalimumab-producing CHO cells were electroporated with the mouse galactosyltransferase β1, 4 expression vector. After 48 hours of culture, G418 (Geneticin®, Life Technologies Catalog Number 10131035) was added to the cell media at a final concentration of 500 μg/ml and the cells were cultured an additional 2-3 weeks. Media was changed once every other day. Stable neomycin resistant transformants were isolated and expanded in culture for 1-3 passages prior to cryopreservation. Two exemplary cell lines, designated GALTR-11 and Gal88-D2E7 were analyzed further.

Example 2

Generation of Monoclonal Antibody-Producing CHO Cells Having a Beta-Galactosidase Knock Down A knock out in one of the alleles of the beta galactosidase gene (*Cricetulus griseus* Glb1 (Gene ID: 100767446); mRNA sequence: NCBI Reference Sequence: XM_007630176.1; genomic sequence NW_003613697.1 from 2278553 to 2336708) of the adalimumab-producing DHFR-deficient CHO cell line was generated using zinc finger nuclease following procedures that are well known in the art (Santiago et al., Proc. Natl. Acad. Sci. USA. 2008; 105(15):5809-14; Remy et al., Transgenic Res. 2010; 19(3): 363-71; Zhang et al., Advances in Biochemical Engineering/Biotechnology Volume 131, 2013, pp 63-87; U.S. Pat. No. 8,313,925). One exemplary cell line, designated ZFN-B1 was analyzed further.

Example 3

Generation of DVD-Ig-Producing Cho Cells Overexpressing β1, 4 Galactosyltransferase IL17×TNF DVD-Ig-producing CHO cells are electroporated with the mouse galactosyltransferase β1, 4 expression vector and G418 (Geneticin®, Life Technologies Catalog Number 10131035) is added to the cell media 48 hours after the transfection at a final concentration of 500 μg/ml for 2-3 weeks. Media is changed once every other day. Stable neomycin resistant transformants are isolated and cultured for 1-3 passages prior to cryopreservation.

Example 4A

Culture of CHO Cells Producing a High Gal/Low Man Fc Containing Binding Protein This exemplary protocol is described for the production of High Gal/Low Man adalimumab but it is generally applicable to the culture of High Gal/Low Man CHO cells expressing any Fc containing binding protein including, but not limited to, DVD-Ig. High Gal/Low Man CHO cells can be either overexpressing galactosyltransferase β1, 4, as described in Example 1, or have a knockout of an allele of the endogenous beta galactosidase gene as described in Example 2.

Growth and production media for the culture of a High Gal/Low Man adalimumab-producing CHO cell line were prepared using a proprietary Life Technologies GIBCO chemically defined media, GIA-1. Basal production and feed media were supplemented with 50 μM Manganese (II) Chloride (Sigma M1787—100 mL; 1.0 M±0.1 M) and 30 mM D(+)Galactose (Sigma G5388—1 kg) (see published U.S. Patent Application No. 2012/0276631 and U.S. Provisional Application 61/886,855). All media were filtered through Corning 0.5 L or 1 L filter systems 0.22 μm Poly (Ether Sulfone) (PES) and stored at 4° C. until use.

The High Gal/Low Man adalimumab-producing CHO cell line was adapted to chemically defined media for 7 (2 to 3 day each) passages in a combination of 250 mL and 500 mL Corning vented non-baffled shake flasks before freezing.

Upon thaw, for the batch shake flask study, cells were expanded for 3 to 5 passages (2 to 3 days each) in a combination of 250 mL and 500 mL Corning vented non-baffled shake flasks. Production cultures were initiated in duplicate 500 mL Corning vented non-baffled shake flasks (200 mL working volume) at an initial viable cell density (VCD) of approximately $0.5 \times 10^6$ cells/mL. Cultures were maintained on orbital shakers at 110 revolutions per minute (RPM) in a dry incubator at 35° C. and 5% $CO_2$. The shake flask study was run in an extended batch mode by feeding with a glucose solution (1.25% (v/v) of 40% solution) when the media glucose concentration fell below 3 g/L.

For the fed-batch bioreactor study, cells were expanded for 8 passages (2 to 3 days each) in Corning vented non-baffled shake flasks maintained on orbital shakers at 110 RPM and in 20 L cell bags (3 L to 10 L working volume) maintained at 20-25 RPM, 7.5° angle, and 0.25 SLPM airflow in a dry incubator at 35° C. and 5% $CO_2$. Production cultures were initiated in duplicate 3 L bioreactors (1.5 L working volume) at 35° C., 30% dissolved oxygen, 200 RPM, pH ramp from 7.1 to 6.9 over 3 days, and pH setpoint of 6.9 thereafter. A fixed split ratio of cells to media of 1:5 was utilized to initiate the production stage cultures. In the fed-batch mode, a chemically-defined feed from Life Technologies GIBCO, JCL-5 (proprietary formulation), was added as follows: 3% (v/v)—day 3, 5%—day 4, 7%—day 5, 10%—day 6, and 10%—day 7. Additional glucose (1.25% (v/v) of 40% solution) was fed when the media glucose concentration fell below 3 g/L.

For all studies with CHO cell lines, samples were collected daily and measured for cell density and viability using a Cedex cell counter. Retention samples for titer analysis via Poros A method were collected by centrifugation at 12,000 RPM for 5 min when the culture viability began declining. The cultures were harvested by collecting 125 mL aliquots and centrifuging at 3,000 RPM for 30 min when culture viability was near or below 50%. All supernatants were stored at −80° C. until analysis.

High Gal/Low Man adalimumab produced by the ZFN-B1 CHO cell (as described in Example 2) is referred to herein as ZFN-B1. High Gal/Low Man adalimumab produced by the GALTR-11 and Gal88-D2E7 CHO cell clones that overexpress β-1, 4 galactosyltransferase (as described in Example 1) are referred to herein as GALTR-11 and Gal88-D2E7, respectively. A High Gal/Low Man anti-TNF×IL17

DVD-Ig (ABT-122) produced by the cell line of Example 3 is referred to herein as Gal79-DVD-Ig.

Example 4B

Production of Highly Sialylated Glycoforms

To prepare approximately 40 mg of GALTR-11 for in-vitro sialylation, the buffer was changed to 35 mM tris acetate, pH 7.4 through dialysis and the concentration adjusted to approximately 5 mg/mL. In vitro sialylation was accomplished by incubating GALTR-11 with activated sialic acid, or more specifically, activated CMP-N-acetyl neuraminic acid (CMP-NANA) and a specific enzyme, α-2,6 sialyltransferase that attaches the sialic acid (NANA) on to the penultimate galactose residue in an α-2,6 linkage. The CMP-NANA was added in a 1:2 CMP-NANA:GALTR-11 ratio and the enzyme was added in a 1:10 enzyme: GALTR-11 ratio, or 4 mg of enzyme to approximately 40 mg of antibody. The volume of the reaction mix was brought up to 15 mL and incubated overnight at 37° C. with gentle shaking.

The level of incorporated sialic acid was quantified by weak ion exchange chromatography using a Shimadzu HPLC equipped with an analytical ProPac® WCX-10 column (4×250 mm). Sample was loaded at 94% mobile phase A(10 mM sodium phosphate, pH 7.5) and 6% buffer B (10 mM sodium phosphate, 500 mM sodium chloride, pH 5.5) and then eluted by the gradient and conditions shown in Table 1 to obtain the glycoengineered adalimumab composition referred to herein as SA-D2E7.

TABLE 1

WCX-10 Chromatography Conditions

| Item | Description/Operating Conditions | |
|---|---|---|
| Mobile phase A | 10 mM sodium phosphate, pH 7.5 | |
| Mobile phase B | 10 mM sodium phosphate/500 mM sodium chloride, pH 5.5 | |
| Gradient | Binary Gradient | |
| | Time (minute) | Mobile Phase B % |
| | 0.5 | 6 |
| | 20 | 16 |
| | 22 | 100 |
| | 26 | 100 |
| | 28 | 6 |
| | 34 | 6 |
| | 35 | 0 (stop) |
| Flow rate | 1.0 mL/min. | |
| Detector wavelength | 280 nm | |
| Autosampler temperature | Nominal 4° C. | |
| Column oven temperature | ambient | |
| Sample load | Up to 100 µL/100 µg | |
| Run time | 35.0 minutes | |

Chromatograms of the SA-D2E7 composition are shown in FIG. 7C. Sialylated GALTR-11 was be separated from the rest of the antibodies containing other glycoforms (i.e., high mannose, G0F, etc.) since sialic acids impart a negative charge to antibodies due to the loss of a proton by the carboxylic group at physiological pH. The other glycoforms are neutral and eluted from the column in the same peak while sialylated GALTR-11 eluted earlier. Sialylated GALTR-11 will elute from an anion exchange column at different retention times depending on the level of sialic acids it contains. Up to four sialic acids can be added to each D2E7 antibody; two for each Fc biantennary glycan. Only the peaks containing three and four sialic acids were collected to ensure relatively pure fractions of SA-D2E7 (containing near 100% of G2S1F and G2S2F type glycans).

The weak ion exchange chromatography method used to collect SA-D2E7 was a modification of the analytical method described above. A GE AKTA Avant system was used with a preparative ProPac® WCX-10 column (22×250 mm) at a flow rate of 25 mL/min. The initial gradient was also stretched out longer, to increase the separation between the early eluting peaks.

Example 5

Analysis of Glycoengineered Adalimumab

The glycan profiles of the ZFN-B1, GALTR-11, Gal88-D2E7, SA-D2E7 and Gal79-DVD were determined.

For all studies, the harvest samples were protein A purified using standard methods (Pure 1A® Kit, Sigma Aldrich, St. Louis, Mo.) and prepared for the oligosaccharide assay using the following procedures.

As a first step in the process of identifying and quantifying the oligosaccharides, total N-glycans were released from protein A-purified hypergalactosylated adalimumab by enzymatic digestion with N-glycanase. Once the glycans were released, the free reducing end of each glycan was labeled by reductive amination with a fluorescent tag, 2-aminobenzamide (2-AB). The resulting labeled glycans were separated by normal-phase HPLC (NP-HPLC) in acetonitrile: 50 mM ammonium formate, pH 4.4, and detected by a fluorescence detector. Quantitation was based on the relative area percent of detected sugars. The results of the analysis for non-hyperglycosylated adalimumab and the hyperglycosylated Adalimumab ZFN-B1, GALTR-11 and Gal88-D2E7 variants are shown in FIG. 2C.

N-deglycosylation of the antibody samples may also be carried out according to the manufacturer's procedure using a Prozyme® N-deglycosylation kit (San Leandro, Calif., USA). Briefly, 300 µg of dried antibody sample are recovered in 135 µL of a 10-mM aqueous Tris-HCl buffer pH 8.0, and 4.5 µL of a 10% (v/v) beta-mercaptoethanol aqueous solution is added to reduce the antibody disulfide bridges. The N-deglycosylation is carried out by the addition of 7.5 mU of peptidyl-N-glycosidase (PNGase F) followed by an overnight incubation at 37 C. At this stage, many N-glycans are released as glycosylamines before slowly hydrolyzing into reducing glycans. The full regeneration of reducing glycans is performed by adding to PNGase F-digested antibody samples glacial acetic acid at a final concentration of 5% (v/v) followed by a one hour incubation at room temperature. The freshly regenerated reducing N-glycan mix is purified by a solid phase extraction (SPE) onto a 50-mg Hypersep Hypercarb® porous graphitized carbon (PGC) column (Thermofischer Scientific, Bremen, Germany) (Packer et al., 1998). The PGC SPE column is sequentially washed with 1 mL methanol and 2×1 mL of a 0.1% (v/v) aqueous trifluoroacetic acid (TFA). The oligosaccharides are dissolved in 200 µL of a 0.1% (v/v) aqueous TFA, applied to the column and washed with 2×1 mL of a 0.1% (v/v) aqueous TFA. The elution of the glycans is performed by applying 2×400 µL of a 25% (v/v) aqueous acetonitrile containing 0.1% (v/v) TFA and the eluate is vacuum-dried.

The PGC-purified glycans are reductively aminated with 2-aminobenzamide (2-AB) by recovering dried glycans by 10 µL of a 33% (v/v) acetic acid in DMSO containing 0.35 M 2-AB and 1 M sodium cyanoborohydride and the reaction is kept at 37 C for 16 hours. The 2-AB-labeled N-glycans are purified onto a 50-mg Oasis® polymeric HLB SPE column, used in the hydrophilic interaction chromatography (HILIC) mode (Waters, Milford, Mass., USA). The HILIC SPE column is sequentially wetted with 1 mL of a 20% (v/v) aqueous acetonitrile and equilibrated with 2×1 mL of acetonitrile, the 2-AB derivatives dissolved in acetonitrile are then loaded onto the SPE column. After washing the column with 2×1 mL of acetonitrile, the elution of the 2-AB derivatives is next performed by applying 2×500 µL of a 20% (v/v) aqueous acetonitrile. The 1-mL eluate is vacuum-concentrated to 50 µL.

The purified 2-AB derivatives are finally profiled by normal-phase high-performance liquid chromatography (NP-HPLC) using a 150×4.6 mm ID TSK-gel amide-80 HILIC HPLC column (TOSOH Bioscience, King of Prussia, Pa., USA) with 3 µm packing particles (Guile et al., 1996). The mobile phase is composed of a mixture of a 50-mM ammonium formate aqueous solution adjusted at pH 4.4 (A) and acetonitrile (B). The operating flow rate and temperature are respectively 1 mL/min and 30 C. 5 µL of the purified 2-AB derivatives are 40-fold diluted using a 80% (v/v) aqueous acetonitrile, and 50 µL of the freshly shaken organic mixture is injected into the HILIC column, and equilibrated with 80% (v/v) B. Once sample injected, the separation of the N-glycans is performed as follows: from 80% to 70% (v/v) B in 15 min; from 70% to 55% (v/v) B in 150 min; from 55% to 10% (v/v) B in 5 min; 10% (v/v) B during 10 min; from 10% to 80% (v/v) in 1 min; 80% (v/v) B during 45 minutes (reequilibration). The detection of the fluorescent derivatives is performed by fluorescence detection (FD) with an excitation wavelength of 330 nm and an emission wavelength of 420 nm.

Figure 2D:
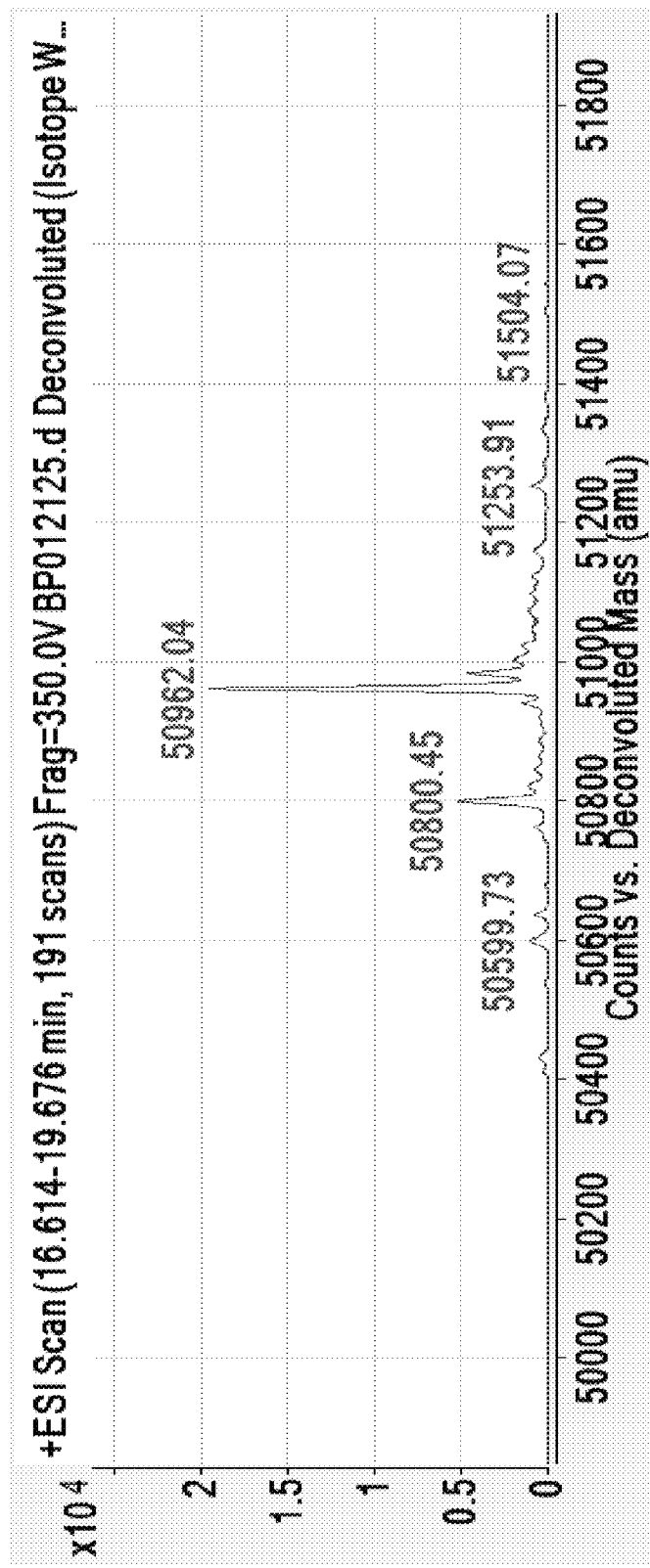
FIG. 2D shows a mass spectrometry (MALDI-TOF) analysis of the glycoengineered Galtr-11 adalimumab preparation in FIG. 2C. Prominent peaks indicate the presence of the G1F (50,800 Da) and G2F (50,962 Da) glycoforms.
Figure 2E:
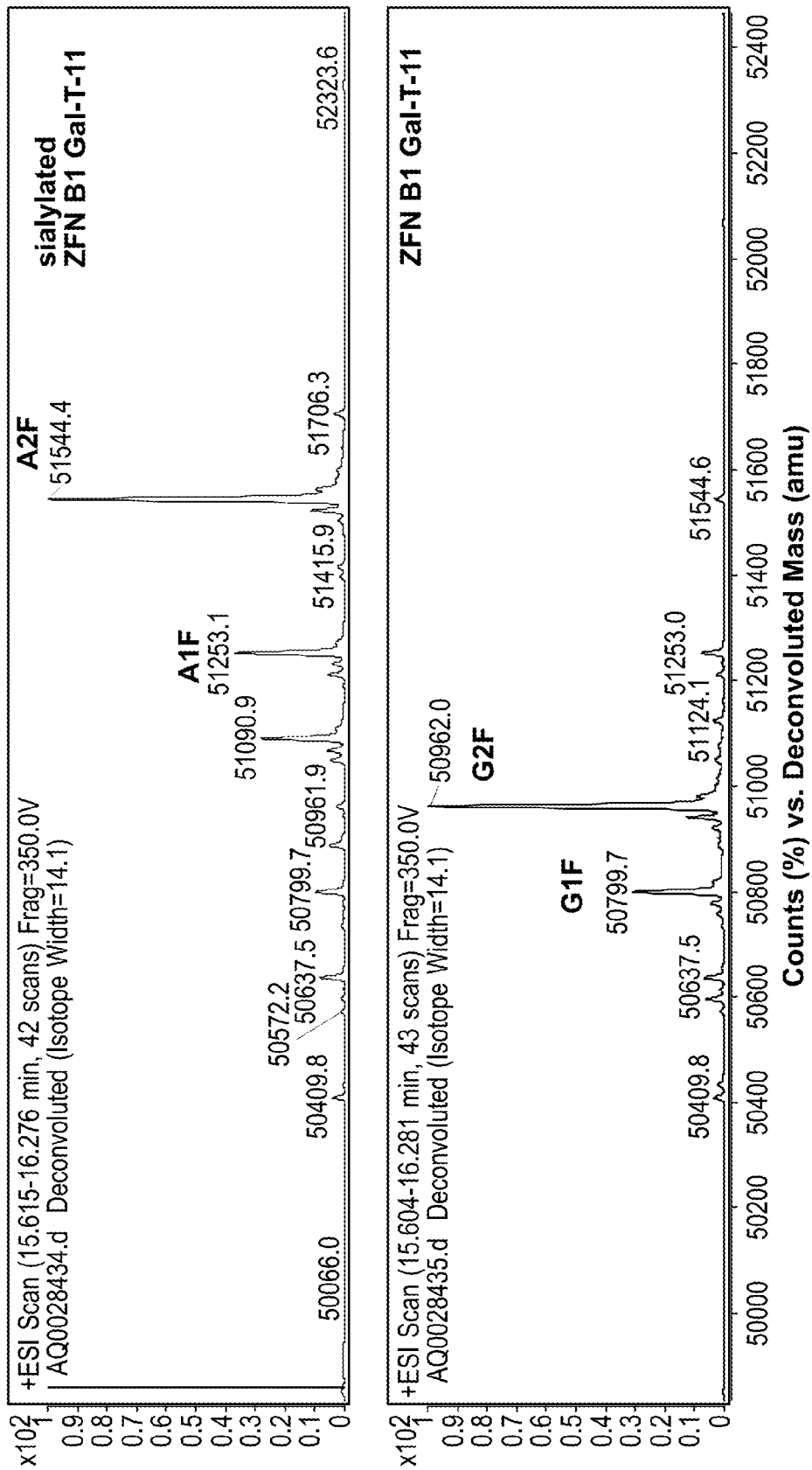
FIG. 2E shows a mass spectrometry (MALDI-TOF) analysis of the glycoengineered SA-D2E7 adalimumab preparation of FIG. 2C before (bottom panel) and after (top panel) treatment with sialyltransferase. Prominent peaks indicate the presence of G1F (50,800 Da), G2F (50,962 Da), G2S1F (A1F; 51,253 Da), and G2S2F (51,544 Da) glycoforms.

MALDI-TOF mass spectroscopy may also be performed to confirm the identity of the apparent hypergalactosylated species. FIG. 2D shows that the major glycans present in a High Gal/Low Man adalimumab preparation (ZFN-B1) are G1F and G2F. FIG. 2E shows the major glycans present in the High Gal/Low Man adalimumab preparation (SA-D2E7) prior to and following treatment with sialyltransferase.

Example 6

TNFα Binding and Internalization of Glycoengineered Adalimumab

Isolation of Monocytes, Culture and Stimulation:

Peripheral blood mononuclear cells (PBMC) were isolated from leukopack of healthy donors by density gradient centrifugation over Ficoll-Paque (GE Health Sciences). Monocytes were isolated by magnetic sorting using CD14 microbeads (Miltenyi Biotec). The purity of the resulting monocytes, as assessed by flow cytometric analysis, was typically greater than 98%. Monocytes were cultured in RPMI1640 medium (Cellgro) supplemented 2 mM L-glutamine, 100 ng/ml of recombinant human GM-CSF (Abbvie) and 5 ng/ml of human IL-4 (Peprotech), 100 µg/ml penicillin, and streptomycin, and 10% fetal bovine serum at a density of 1×10$^6$ cells/ml at 37° C. with 5% CO2 for 5 days.

Figure 3A:
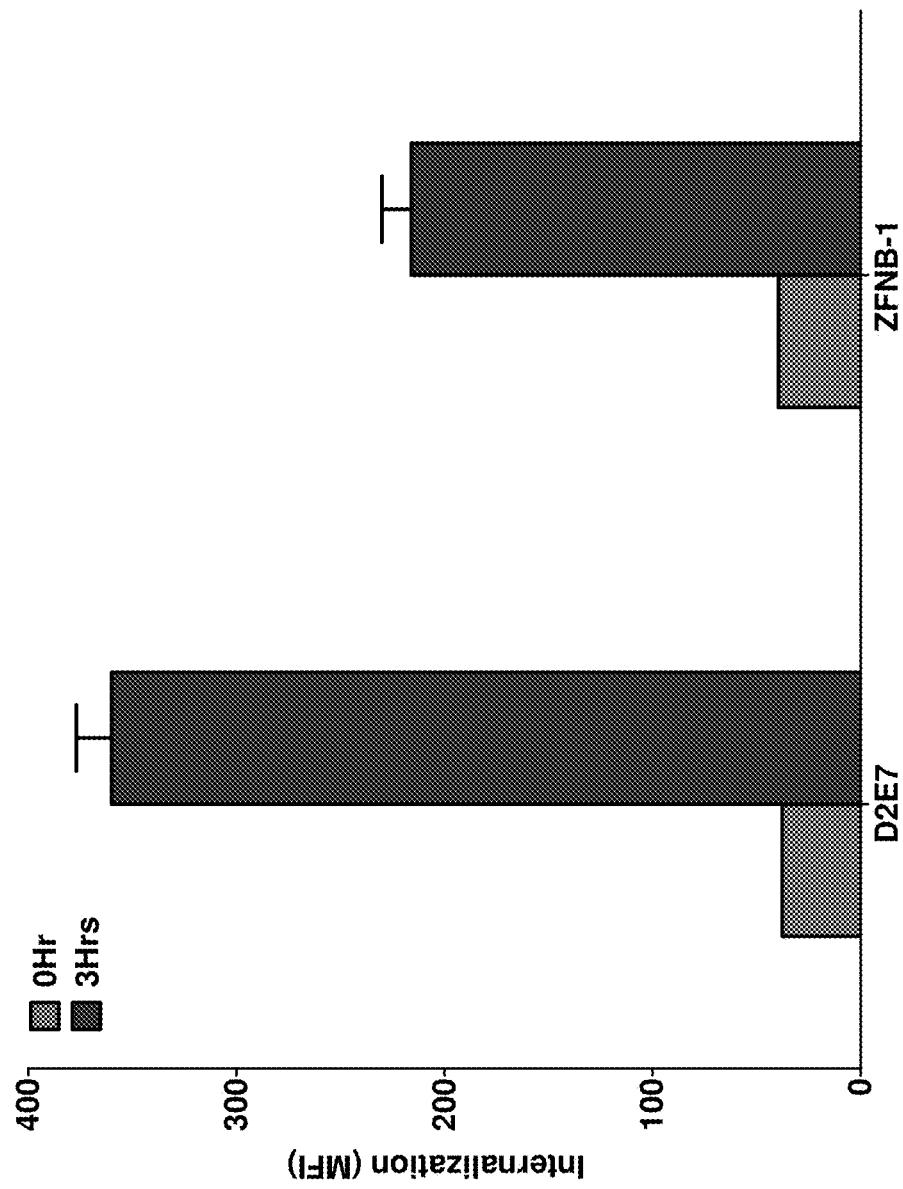
FIG. 3A shows the pinocytosis by human dendritic cells of non-glycoengineered adalimumab (D2E7/Humira®) and glycoengineered adalimumab (ZFN-B1) produced in a CHO cell line with a knockout of one of the alleles of the beta galactosidase gene.
Figure 3B:
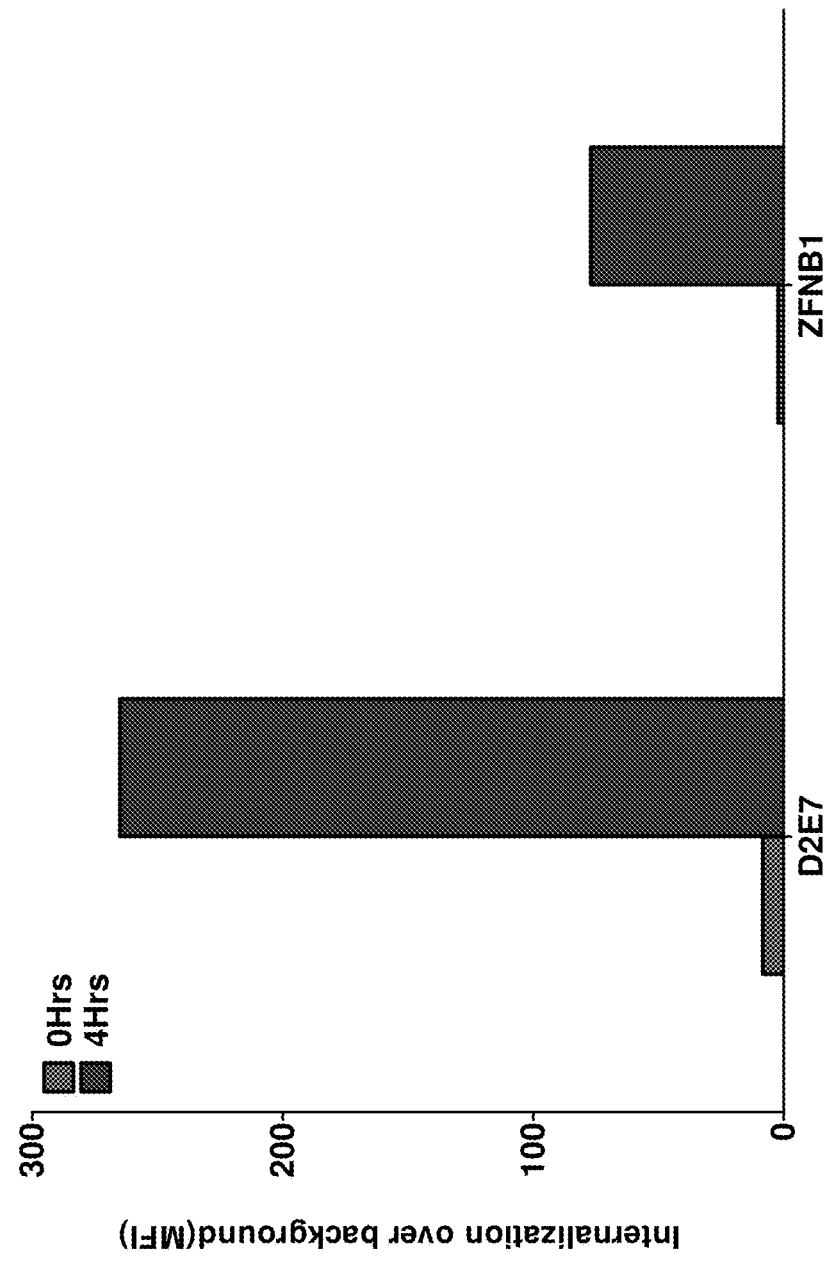
FIG. 3B shows the internalization of transmembrane TNFα induced in dendritic cells by non-glycoengineered adalimumab (D2E7/Humira®) and glycoengineered adalimumab (ZFN-B1) produced in a CHO cell line with a knockout of one of the alleles of the beta galactosidase gene.
Figure 3C:
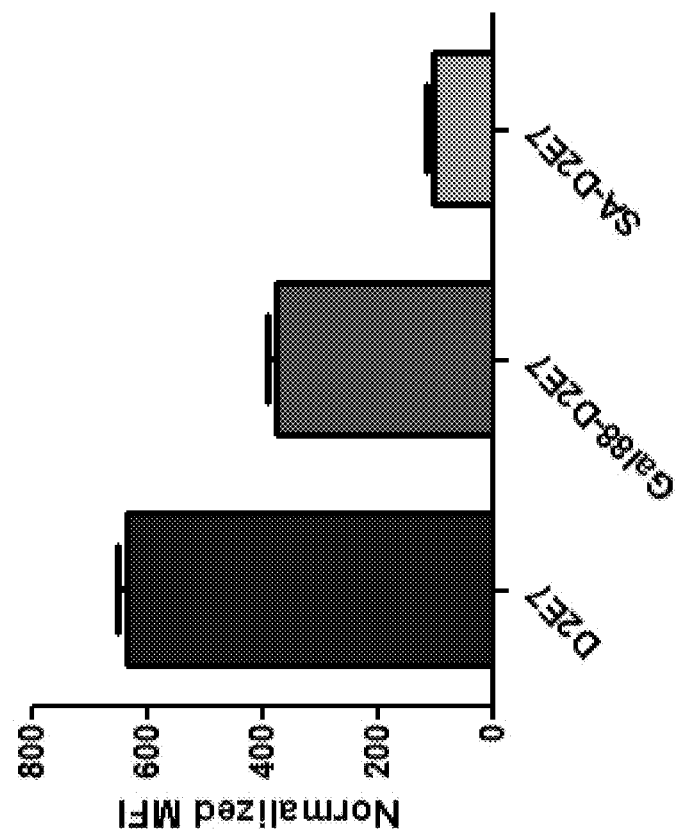
FIG. 3C shows the pinocytosis by human dendritic cells of non-glycoengineered adalimumab (D2E7/Humira®) and glycoengineered adalimumab (Gal88-D2E7 and SA-D2E7).

To test the surface TNFalpha expression, PBMCs or monocytes were stimulated with ultra-low (0.025 ng/ml), low (0.25 ng/ml) or high (250 ng/ml) of LPS (from *Salmonella typhimurium*, Sigma-Aldrich) for one hour.
Dendritic Cell Differentiation and Stimulation Dendritic cells were generated by culturing monocytes in RPMI1640 medium supplemented with 100 ng/ml of recombinant human GM-CSF (Abbvie) and 5 ng/ml of human IL-4 (Peprotech) for 4 days. To investigate the TNFalpha production, DCs were stimulated with 1 mg/ml LPS (from *Salmonella typhimurium*, Sigma-Aldrich) for 1hour.
Staining Cells and Flow Cytometric Analysis LPS stimulated PBCs, monocyte or DCs were blocked with human IgG and stained with pH$^{Rodo}$ red labeled D2E7 on ice, then incubated at 37° C. As a negative control an isotype matched control antibody (AB446) was used. All the antibodies were conjugated with A488 using antibody labeling kit (Invitrogen) according to manufacturer's protocol. Monocytes and T cells were gated based on the expression of CD14 (Biolegend) and CD3 (eBioscience) respectively. Samples were analyzed on a Becton Dickinson Fortessa® flow cytometer, and analysis was performed using Flowjo® software (TreeStar Inc., Ashland, Oreg., USA).
Internalization Assay To investigate the internalization of surface TNF bound adalimumab antibodies, monocytes were stimulated with LPS for 4, 7, 9 or 24 hours in the presence of Alexa 488 conjugated AB436 antibodies. Cells were permeabilized and nucleus was stained with DAPI. The images were acquired using confocal microscope (Zeiss). To study the internalization of anti-TNF adalimumab antibodies by dendritic cells, the monocyte derived DCs were stimulated with LPS for 4 hours in the presence of anti-TNF adalimumab or matched isotype control antibodies. The anti-TNFalpha specific adalimumab antibodies and control antibodies were conjugated with pH sensitive dye pH$^{Rodo}$ Red (Invitrogen) according to manufacturer's protocol. The cells were analyzed by fluorescent microscope and FACS. Where indicated, the surface of the cells was stained with A488-conjugated anti-HLA-A,B,C (W6/32, Biolegend) antibodies and the nucleus was stained with Nuce® blue (Invitrogen). To study the internalization kinetics of anti-TNFalpha adalimumab antibodies by membrane TNF on DCs, cells were either left in un-stimulated or stimulated with LPS for 1 hour or 24 hours. The surface TNFalpha was stained with pH$^{Rodo}$ Red conjugated anti-TNFalpha antibody (AB441). The stained cells were cultured in RPMI medium for the indicated time and the internalization was assessed as an increase in fluorescence using BD Fortessa flow cytometer (see FIGS. 3A-3C). The results indicate that that the glycoengineered Adalimumab preparations of the invention exhibit pronounced decrease immunogenicity as a result of their reduced internalization and antigenic presentation by dendritic cells.

Example 7

Pharmacokinetic Studies

Non-hypergalactosylated adalimumab (D2E7) and hypergalactosylated adalimumab (ZFN-B1) monoclonal antibodies were administered to CD-1 or BALB/C mice by slow intravenous bolus dose injection at a 5 mg/kg dose. Blood samples were collected from each mouse at 1, 24 and 96 hours and 7, 10, 14 and 21 days post dose. Blood samples were collected from each rat at 0.25, 4, and 24 hours and 2, 3, 7, 10, 14, 21 and 28 days post dose. All samples were stored at −80° C. until analysis.

Figure 4:
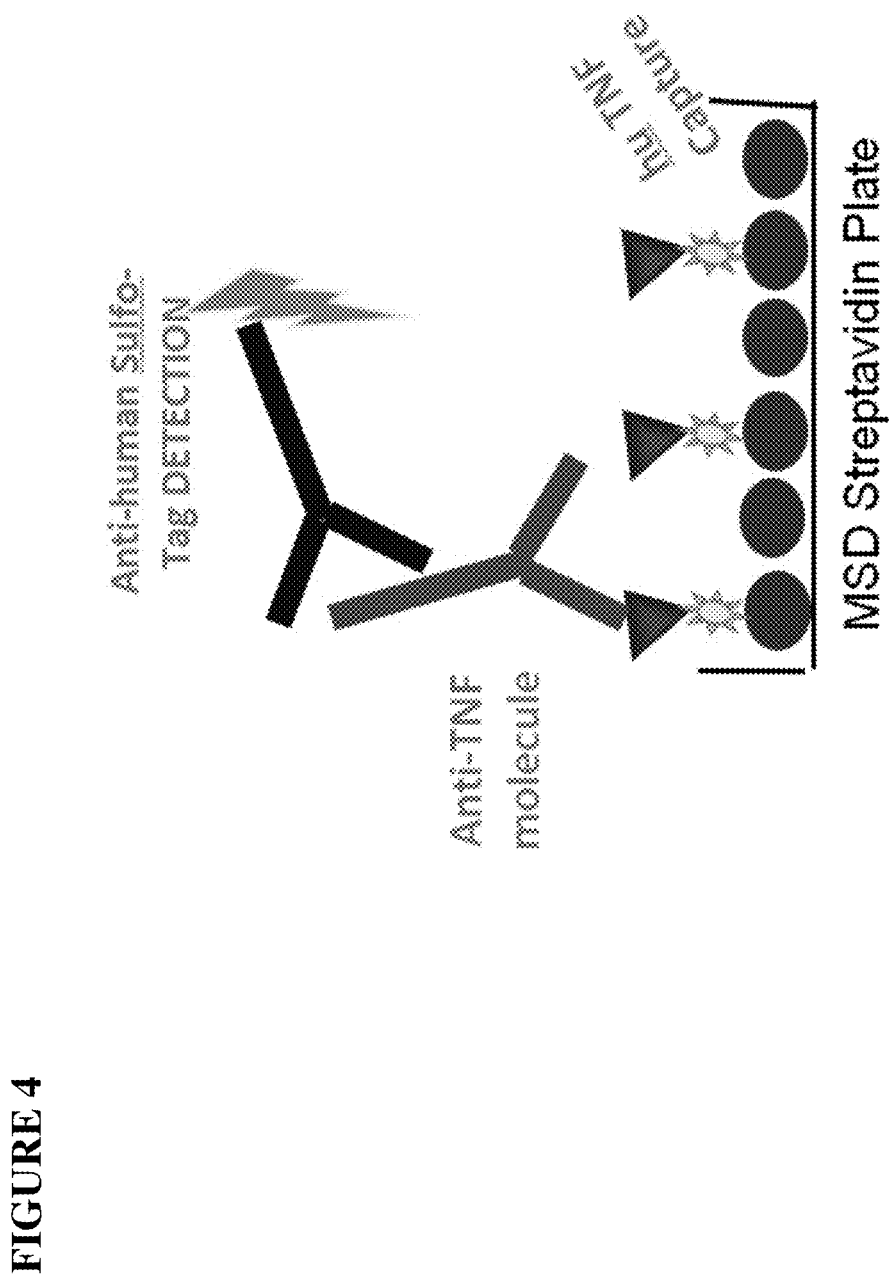
FIG. 4 is a schematic of the anti-TNFα capture assay employed for Drug Metabolism and Pharmacokinetics (DMPK) Bioanalysis of the glycoengineered compositions of the invention.

Serum samples were analyzed using an anti-TNF capture assay depicted in FIG. 4 in which a biotinylated humanTNFα was used for capture and a labeled anti-human Sulfo-Tag for detection. The assay was carried out in 1% final serum concentration. The lower limit of quantitation (LLOQ) was 0.004 µg/mL. The linear range: 15-0.004 µg/mL. The low control was 0.1 µg/mL.

Standard curve fitting and data evaluation was performed using XLfit4 software with a four-parameter logistic fit. Plates passed when at least 2/3 of the QC's were within 30% of the expected values. Pharmacokinetic parameters for each animal were calculated using WinNonlin® software Version 5.0.1 (Pharsight Corporation, Mountain View, Calif.) by non-compartmental analysis using linear trapezoidal fit (NCA Models #201 for IV dosing). For calculations in WinNonlin, the time of dosing was defined as Day 0 Time 0 hr.

Figure 5A:
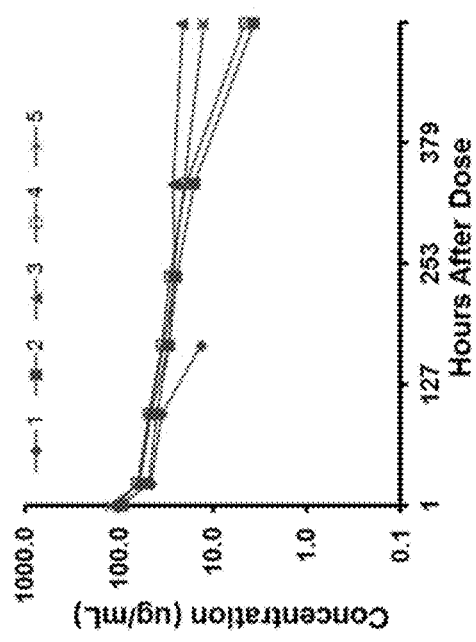
FIG. 5A shows the pharmacokinetic (PK) profile of a glycoengineered (hypergalactosylated and hypomannosylated) preparation of anti-TNFα mAb (ZFN-B-1; lot 2168407) Serum Concentrations after 5 mg/kg IV Dosing in CD-1 Mice (W14-0201).
Figure 5B:
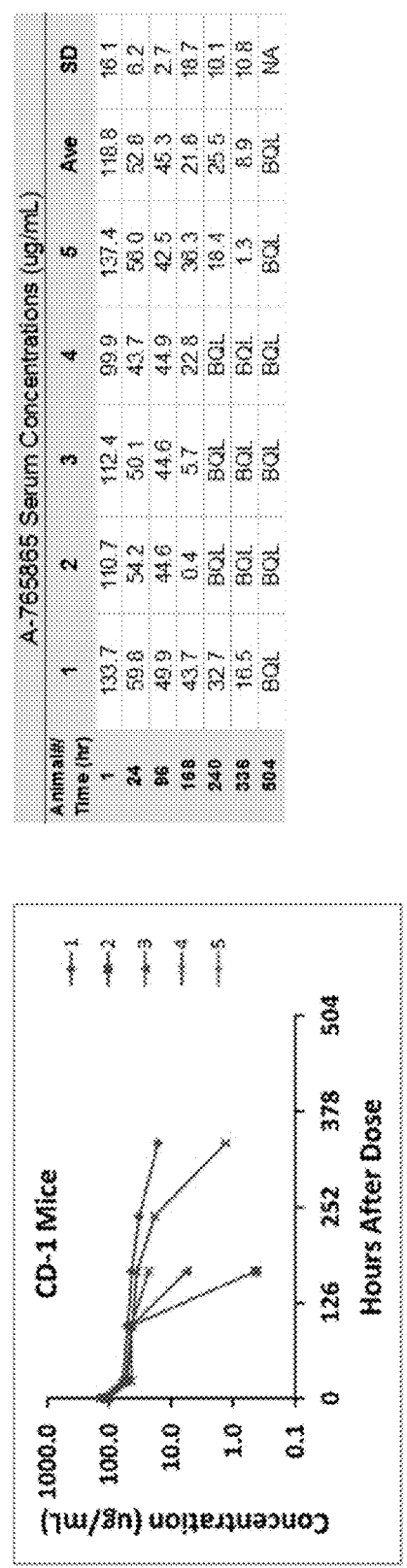
FIG. 5B shows the pharmacokinetic (PK) profile of a non-glycoengineered preparation of anti-TNFα mAb D2E7 (HUMIRA®; lot 2158962) Serum Concentrations after 5 mg/kg IV dosing in CD-1 Mice (W14-0203).
Figure 6:
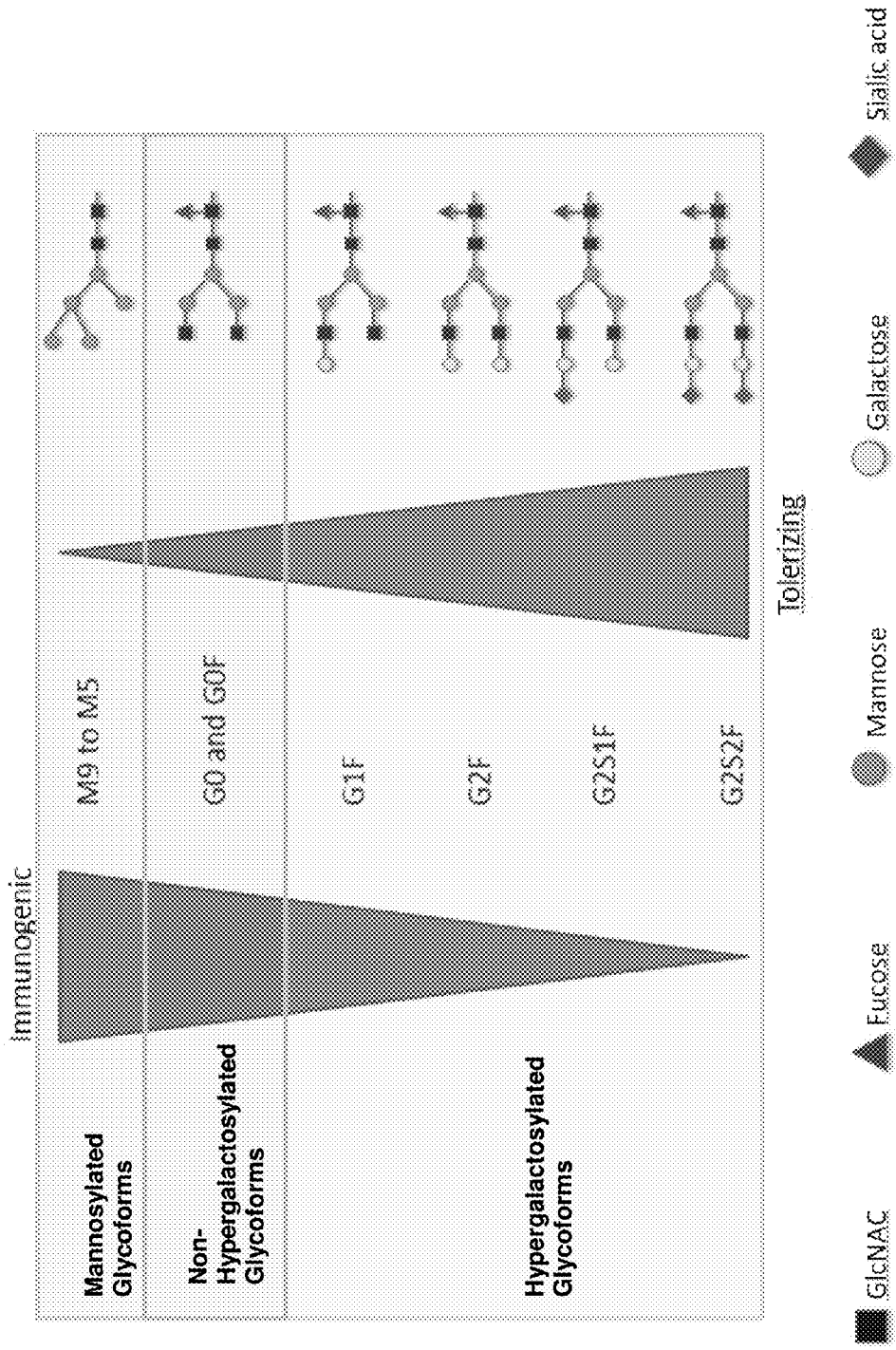
FIG. 6 is a schematic depicting exemplary naturally-occurring N-glycan glycoforms. Mammalian cells have a more diverse range of modifications than any of the other organisms. Certain motifs extending the N-glycan arms (lactosamine chains, terminal GalNAc, terminal sialylation, fucosylation) are also found in mammalian 0-glycans.

The serum concentrations as a function of time are shown in FIG. 5A (ZFN-B1) and FIG. 5B (D2E7). The pharmacokinetic parameters for High Gal ZFN-B1 administered mice #3 and 5 are depicted in FIG. 5C. The result show that 4 of 5 animals administered anti-TNF hypergalactosylated ZFN-B1 monoclonal antibody had measurable antibody levels out to 21 days (FIG. 5A). The High Gal ZFN-B1 administered mouse #3 displayed a long half-life and low CL (24.5 days and 0.14 mL/h/kg). In contrast, all the animals administered the anti-TNF D2E7 monoclonal antibody displayed probable anti-drug antibodies (ADA). The results suggest that anti-drug antibodies decrease as a function of the galactosylation of the administered recombinant Fc binding protein (see FIG. 6).

We claim:

1. A composition comprising a population of Fc domain-containing binding proteins wherein 0.1 to 3% of the Fc domain-containing binding proteins in the population comprise M3-M9 glycoforms and wherein the Fc domain-containing binding proteins comprise the polypeptide sequence of adalimumab.

2. The composition of claim 1, wherein 0.1-2% of the Fc domain-containing binding proteins in the population comprise M3-M9 glycoforms.

3. The composition of claim 1, wherein 0.1-3% of the Fc domain-containing binding proteins in the population comprise M5-M7 glycoforms.

4. The composition of claim 1, wherein the level of M3-M9 glycoforms is determined using a 2-AB labeling method.

5. The composition of claim 4, wherein the 2-AB labeling method employs a fluorophore selected from the group consisting of a 2-AB (2-aminobenzamide) and a 2-AA (anthranilic acid or 2-aminobenzoic acid).

6. The composition of claim 1, wherein the composition is produced in a cultured mammalian host cell line.

7. The composition of claim 6, wherein the cultured mammalian host cell line is selected from the group consisting of a CHO cell line, a HEK 293 cell line, a NS0 myeloma cell line, a COS cell line and a SP2 cell line.

8. The composition of claim 6, wherein the cultured mammalian host cell line is a CHO cell line.

9. A pharmaceutical composition comprising the population of Fc domain-containing binding proteins of claim 1, and a pharmaceutically acceptable carrier.

10. The pharmaceutical composition of claim 9, wherein the population of Fc domain-containing binding proteins is formulated for administration at a dosage of about 0.1-20 mg/kg.

11. The pharmaceutical composition of claim 9, wherein the pharmaceutically acceptable carrier comprises one or more excipient selected from the group consisting of a buffering agent, a surfactant and a polyol, or a combination thereof.

12. The pharmaceutical composition of claim 11, wherein the buffering agent is an amino acid.

13. The pharmaceutical composition of claim 12, wherein the amino acid is histidine.

14. The pharmaceutical composition of claim 11, wherein the surfactant is polysorbate 80.

15. The pharmaceutical composition of claim 11, wherein the polyol is mannitol.

16. The pharmaceutical composition of claim 9, wherein the pharmaceutical composition is in a syringe.

17. A composition comprising a population of Fc domain-containing binding proteins wherein 0.1 to 3% of the Fc domain-containing binding proteins in the population comprise M5-M9 glycoforms and wherein the Fc domain-containing binding proteins comprise the polypeptide sequence of adalimumab.

18. The composition of claim 17, wherein 0.1-2% of the Fc domain-containing binding proteins in the population comprise M5-M9 glycoforms.

19. A pharmaceutical composition comprising the population of Fc domain-containing binding proteins of claim 17, and a pharmaceutically acceptable carrier.

20. The pharmaceutical composition of claim 19, wherein the population of Fc domain-containing binding proteins is formulated for administration at a dosage of about 0.1-20 mg/kg.

21. The pharmaceutical composition of claim 19, wherein the pharmaceutically acceptable carrier comprises one or more excipient selected from the group consisting of a buffering agent, a surfactant and a polyol, or a combination thereof.

22. The pharmaceutical composition of claim 21, wherein the buffering agent is an amino acid.

23. The pharmaceutical composition of claim 22, wherein the amino acid is histidine.

24. The pharmaceutical composition of claim 21, wherein the surfactant is polysorbate 80.

25. The pharmaceutical composition of claim 21, wherein the polyol is mannitol.

26. The composition of claim 8, wherein the CHO cell line is a glycoengineered CHO cell line.

27. The composition of claim 17, wherein the composition is produced in a cultured mammalian host cell line.

28. The composition of claim 27, wherein the cultured mammalian host cell line is selected from the group consisting of a CHO cell line, a HEK 293 cell line, a NS0 myeloma cell line, a COS cell line and a SP2 cell line.

29. The composition of claim 27, wherein the cultured mammalian host cell line is a CHO cell line.

30. The composition of claim 29, wherein the CHO cell line is a glycoengineered CHO cell line.

* * * * *